United States Patent
Wong et al.

(10) Patent No.: US 10,183,027 B2
(45) Date of Patent: Jan. 22, 2019

(54) LANTHANIDE TOOLBOX FOR MULTI-MODAL, NON-INVASIVE TUMOR SPECIFIC THERANOSTIC PRODRUGS

(71) Applicant: Hong Kong Baptist University, Hong Kong (HK)

(72) Inventors: Ka Leung Wong, Hong Kong (HK); Hongguang Li, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/709,942

(22) Filed: Sep. 20, 2017

(65) Prior Publication Data
US 2018/0078564 A1    Mar. 22, 2018

Related U.S. Application Data

(60) Provisional application No. 62/397,360, filed on Sep. 21, 2016.

(51) Int. Cl.
*C07F 5/00* (2006.01)
*A61K 31/555* (2006.01)
*A61K 47/64* (2017.01)

(52) U.S. Cl.
CPC ............ *A61K 31/555* (2013.01); *A61K 47/64* (2017.08); *C07F 5/003* (2013.01)

(58) Field of Classification Search
CPC .......... C07F 5/003; C07F 5/00; A61K 31/555; A61K 47/64
See application file for complete search history.

(56) References Cited

U.S. PATENT DOCUMENTS

| | | | | |
|---|---|---|---|---|
| 4,599,352 A | * | 7/1986 | Narayanan ........... | C07F 15/0093 514/492 |
| 4,675,336 A | * | 6/1987 | Bitha .................. | C07F 15/0093 514/492 |
| 8,357,678 B2 | * | 1/2013 | Mei ..................... | C07F 15/0053 514/185 |
| 2012/0220922 A1 | * | 8/2012 | Yuste ................. | C07F 15/0053 604/20 |
| 2017/0342090 A1 | * | 11/2017 | Wong ................. | C12Q 1/527 |

FOREIGN PATENT DOCUMENTS

| | | |
|---|---|---|
| WO | 2006/120444 A1 | 11/2006 |
| WO | 2008/007089 A1 | 1/2008 |
| WO | 2009-010580 | 1/2009 |
| WO | 2010/084090 A1 | 7/2010 |

OTHER PUBLICATIONS

Goodman & Gilman's: The Pharmacological Basis of Therapeutics 853-908 (L.L. Brunton et al., eds., 11th ed., 2008).*
H. Li et al., 53 Chemical Communications, 7084-7087 (2017).*
H. Li et al., 51 Chemical Communication, 14022-14025 (2015).*
J.S. Butler et al., 17 Current Opinion in Chemical Biology, 175-188 (2013).*
S. Thota et al., 23 Chinese Chemical Letters, 466-469 (2012).*
L. Liu et al., Scientific Reports, 1-11 (2015).*
M. Piccart et al., 12 Annals of Oncology, 1195-1203 (2001).*
P.J. O'Dwyer et al., Clinical Status of Cisplatin, Carboplatin, and Other Platinum-Based Antitumor Drugs (1999).*
E. Wong et al., 99 Chemical Reviews, 2451-2466 (1999).*
C. Cheng et al., 47 Journal of the Chinese Chemical Society (Taipei), 213-220 (2000).*
M.J. Cleare et al., 2 Bioinorganic Chemistry, 187-210 (1973).*
T. A. Connors et al., 5 Chem.-Biol. Interactions, 415-424 (1972).*
N. Grover et al., 114 Journal of the American Chemical Society, 3390-3393 (1992).*
N. Grover et al., 33 Inorganic Chemistry, 3544-3548 (1994).*
X. Wang et al., 42 Chemical Society Reviews, 202-224 (2013).*
International Search Report and Written Opinion of PCT application No. PCT/CN2017/102813 issued from the International Search Authority dated Dec. 26, 2017.
Hongguang Li et al. "Real-time in-situ monitoring via europium emission of the photo-release of antitumor cisplatin from a Eu-Pt complex", ChemComm, Sep. 25, 2015, pp. 14022-14025, vol. 51 No. 74, Jornal of the Royal Society of Chemistry 2015.

* cited by examiner

*Primary Examiner* — Alexander R Pagano
(74) *Attorney, Agent, or Firm* — Spruson & Ferguson (Hong Kong) Limited

(57) ABSTRACT

The present disclosure relates to theranostic prodrugs with responsive signals in-vitro or in-vivo and uses thereof. It also relates to synthesized europium complexes for evaluating the binding with integrin $\alpha v \beta 3$.

13 Claims, 43 Drawing Sheets
(13 of 43 Drawing Sheet(s) Filed in Color)
Specification includes a Sequence Listing.

Plan A Fluorescence imaging

Note : $R_n$ represents all variation of R ($R_1$-$R_8$) group in the structures.
  $P_n$ Wherein $P_n$ is an cancer targeting vector SEQ ID NO: 1-5 or a biotin derivative
  $R_1$ = H or $P_n$
  $R_2$ = H or Me
  $R_3$, $R_4$, $R_5$ = H, OMe, $NMe_2$ or $CF_3$
  $R_6$, $R_7$, $R_8$ = O⁻ or $P_n$
  Ln = Eu or or Gd or Yb or other lanthanide elements

Plan B. Optical and MR Dual imaging

Ln$_1$ = Eu(or Yb) and Ln$_2$ = Gd

Hybrid Eu(or Yb):Gd = 50 : 50 or

Dimeric Ln$_1$ = Eu(or Yb) and Ln$_2$ = Gd

Note :
- $R_1$ = H or $P_n$
- $R_2$ = H or $P_n$
- $R_3$, $R_4$, $R_5$ = H, OMe, NMe$_2$ or CF$_3$
- $R_6$, $R_7$, $R_8$ = O$^-$ or $P_n$
- Ln$_1$ = Eu or Yb
- Ln$_2$ = Gd

SEQUENCE LISTING

<160> NUMBER OF SEQ ID NOS: 5

<210> SEQ ID NO 1
<211> LENGTH: 15
<212> TYPE: PRT
<213> ORGANISM: Artificial Sequence

```
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: DISULFID
<222> LOCATION: (2)..(10)
<223> OTHER INFORMATION: the side chain of C in positions two and ten
      are covalently bonded via a disulfide bond
<220> FEATURE:
<221> NAME/KEY: MISC_FEATURE
<222> LOCATION: (10)..(10)
<223> OTHER INFORMATION: C in position two is a D-amino acid
<220> FEATURE:
<221> NAME/KEY: MISC_FEATURE
<222> LOCATION: (11)..(11)
<223> OTHER INFORMATION: Xaa in position one is 6-aminocaproic acid
<220> FEATURE:
<221> NAME/KEY: MISC_FEATURE
<222> LOCATION: (12)..(12)
<223> OTHER INFORMATION: R in position twelve is a D-amino acid
<220> FEATURE:
<221> NAME/KEY: MISC_FEATURE
<222> LOCATION: (14)..(14)
<223> OTHER INFORMATION: R in position fourteen is a D-amino acid

<400> SEQUENCE: 1

Xaa Cys Gly Arg Leu Lys Glu Arg Arg Cys Xaa Arg Arg Arg Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: MISC_FEATURE
<222> LOCATION: (10)..(10)
<223> OTHER INFORMATION: C in position ten is a D-amino acid
<220> FEATURE:
<221> NAME/KEY: MISC_FEATURE
<222> LOCATION: (11)..(11)
<223> OTHER INFORMATION: Xaa in position eleven is 6-aminocaproic acid
<220> FEATURE:
<221> NAME/KEY: MISC_FEATURE
<222> LOCATION: (12)..(12)
<223> OTHER INFORMATION: R in position eleven is is a D-amino acid
<220> FEATURE:
<221> NAME/KEY: MISC_FEATURE
<222> LOCATION: (14)..(14)
<223> OTHER INFORMATION: R in position fourteen is is a D-amino acid

<400> SEQUENCE: 2
```

```
Xaa Cys Gln Arg Gly Gly Arg Lys His Cys Xaa Arg Arg Arg Lys
1               5                   10                  15
```

<210> SEQ ID NO 3
<211> LENGTH: 14
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: DISULFID
<222> LOCATION: (2)..(9)
<223> OTHER INFORMATION: The side chain of C in position two taken
      together with the side chain of C in position nine form a
      disulfide bond
<220> FEATURE:
<221> NAME/KEY: MISC_FEATURE
<222> LOCATION: (9)..(9)
<223> OTHER INFORMATION: C in position nine is a D-amino acid
<220> FEATURE:
<221> NAME/KEY: MISC_FEATURE
<222> LOCATION: (10)..(10)
<223> OTHER INFORMATION: Xaa in position ten is 6-aminocaproic acid
<220> FEATURE:
<221> NAME/KEY: MISC_FEATURE
<222> LOCATION: (11)..(11)
<223> OTHER INFORMATION: R in position eleven is a D-amino acid
<220> FEATURE:
<221> NAME/KEY: MISC_FEATURE
<222> LOCATION: (13)..(13)
<223> OTHER INFORMATION: R in position thirteen is a D-amino acid

<400> SEQUENCE: 3

```
Xaa Cys Met Lys Lys His Lys Arg Cys Xaa Arg Arg Arg Lys
1               5                   10
```

<210> SEQ ID NO 4
<211> LENGTH: 13
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: DISULFID
<222> LOCATION: (2)..(8)
<223> OTHER INFORMATION: The side chain of C in position two taken
      together with the side chain of C in position eight form a
      disulfide bond

```
<220> FEATURE:
<221> NAME/KEY: MISC_FEATURE
<222> LOCATION: (8)..(8)
<223> OTHER INFORMATION: C in position eight is a D-amino acid
<220> FEATURE:
<221> NAME/KEY: MISC_FEATURE
<222> LOCATION: (9)..(9)
<223> OTHER INFORMATION: Xaa in position nine is 6-aminocaproic acid
<220> FEATURE:
<221> NAME/KEY: MISC_FEATURE
<222> LOCATION: (10)..(10)
<223> OTHER INFORMATION: R in position twelve is a D-amino acid
<220> FEATURE:
<221> NAME/KEY: MISC_FEATURE
<222> LOCATION: (12)..(12)
<223> OTHER INFORMATION: R in position twelve is a D-amino acid

<400> SEQUENCE: 4

Xaa Cys Phe Glu Glu Phe Gly Cys Xaa Arg Arg Arg Lys
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (10)..(10)
<223> OTHER INFORMATION: C in position ten is a D-amino acid
<220> FEATURE:
<221> NAME/KEY: MISC_FEATURE
<222> LOCATION: (11)..(11)
<223> OTHER INFORMATION: Xaa in position eleven is 6-aminocaproic acid
<220> FEATURE:
<221> NAME/KEY: MISC_FEATURE
<222> LOCATION: (12)..(12)
<223> OTHER INFORMATION: R in position twelve is a D-amino acid
<220> FEATURE:
<221> NAME/KEY: MISC_FEATURE
<222> LOCATION: (14)..(14)
<223> OTHER INFORMATION: R in position fourteen is a D-amino acid

<400> SEQUENCE: 5

Xaa Cys Gln Glu Gly Arg Met Gly Phe Cys Xaa Arg Arg Arg Lys
1               5                   10                  15
```

LANTHANIDE TOOLBOX FOR MULTI-MODAL, NON-INVASIVE TUMOR SPECIFIC THERANOSTIC PRODRUGS

CROSS-REFERENCE TO RELATED APPLICATIONS

This application claims priority from U.S. Provisional Patent Application Ser. No. 62/397,360 filed on Sep. 21, 2016, the disclosure of which is hereby incorporated by reference.

FIELD OF THE INVENTION

The present disclosure relates to theranostic prodrugs with responsive signals in-vitro or in-vivo. More particularly, it relates to tumor targeting and non-tumor targeting prodrug lanthanide (such as europium/ytterbium/gadolinium, etc)-d-transition metal (such as ruthenium/platinum, etc) complexes for evaluating the binding with tumor cell membrane bound receptors for specific cancers, such as the integrin αvβ3 for bladder cancer.

BACKGROUND OF THE INVENTION

Highly cytotoxic platinum (II)/(IV) coordination complexes, like cisplatin and its derivatives (carboplatin/oxaliplatin), are well-known potent anticancer agents. Pharmacologically inactive forms of these compounds, otherwise known as prodrugs, have been developed to optimize the drug delivery process, e.g. tumor selectivity, water solubility and cell permeability, before subsequent activation at the target sites. Despite the clinical success of several prodrugs, it remains an unprecedented challenge to achieve the desired pharmacokinetics, with minimal adverse side effects, since they are non-specifically distributed throughout the body. The major drawback of prodrugs, according to the literature, is linked to difficulties in tracing their activities in-vitro or in-vivo. Intriguingly, the recent advent of theranostic nanomedicine, an emerging paradigm of combining diagnostic and therapeutic entities into one, creates a new research landscape and provides a promising solution to the prodrug conundrum.

Theranostic technology affords simultaneous imaging diagnosis and targeted therapy of diseases. Theranostic nanoagents of diagnostic capability and therapeutic efficacy can be, for instance, used in pathological mechanistic studies and can guide pre-/post-treatment assessment due to their responsive signaling capability, e.g. magnetic resonance and fluorescence in-vitro or in-vivo studies. Biodistribution information can be obtained and photocontrolled drug release/photodynamic therapy manipulated. Borrowing the concept from the nano-counterparts, it is an objective of the present disclosure to provide additional theranostic molecular prodrugs with improved therapeutic and/or diagnostic properties.

SUMMARY OF THE INVENTION

Provided herein are biocompatible lanthanide complexes or materials which can selectively differentiate cancer cells and whose delivery can be visualized using a non-toxic excitation wavelength in which release of the cytotoxic d-transition metal complexes (such as cisplatin, ruthenium polypyridine complexes, etc) is triggered selectively upon reaching the overexpressed cancer specific membrane receptor.

In certain embodiments, provided herein is a compound comprising a chemical structure of formula (I):

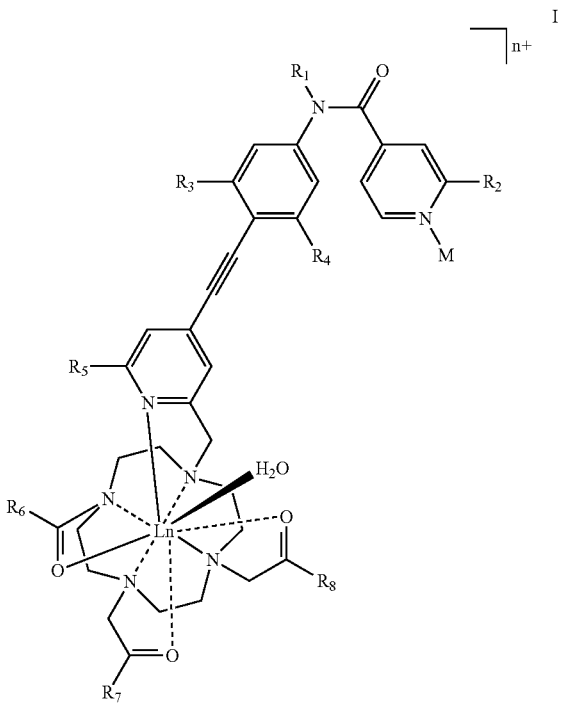

wherein Ln is a lanthanide metal;
$R_1$ is independently hydrogen, $P_n$,

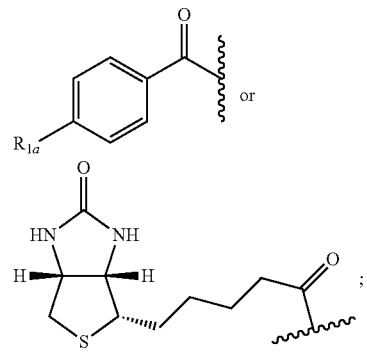

$R_{1a}$ is hydrogen or $P_n$;
$R_2$ is hydrogen or alkyl;
each of $R_3$, $R_4$ and $R_5$ is independently hydrogen, OMe, $NMe_2$, or $CF_3$;
each of $R_6$, $R_7$ and $R_8$ is independently $O^-$, $P_n$, or

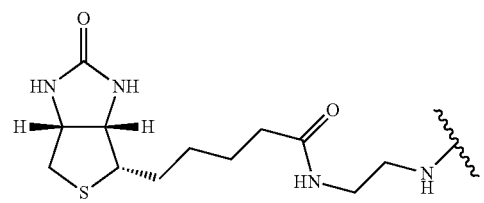 [SMILES: *NCCNC(=O)CCCC[C@@H]1SC[C@@H]2NC(=O)N[C@@H]21]

$P_n$ is a polypeptide represented by SEQ ID NO: 1, 2, 3, 4, or 5;

M represents a moiety selected from the group consisting of:

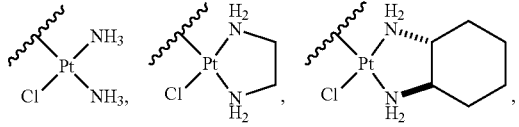

and

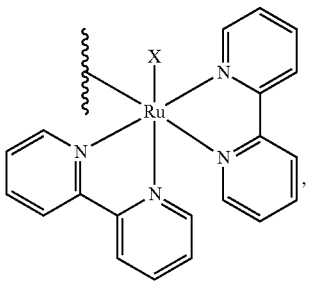

wherein X is Cl or OH; and n+ represents the net charge of the compound and is +1, +2, +3, or +4; with the proviso that if M is

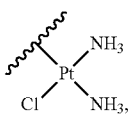

then $R_2$ is alkyl or at least one of $R_1$, $R_{1a}$, $R_6$, $R_7$, and $R_8$, is $P_n$.

In certain embodiments, provided herein is a compound comprising the chemical structure of formula I, wherein $R_1$ is $P_n$ and $R_6$, $R_7$ and $R_8$ are O⁻; $R_1$ is H, $R_6$ and $R_7$ are O⁻, and $R_8$ is $P_n$; or $R_1$ is H, $R_6$ and $R_8$ are O⁻, and $R_7$ is $P_n$; or $R_1$ is H and $R_6$, $R_7$ and $R_8$ are O⁻.

In certain embodiments, provided herein is a compound comprising the chemical structure of formula I, wherein $R_2$ is methyl or at least one of $R_1$, $R_6$, $R_7$, or $R_8$ is $P_n$.

In certain embodiments, provided herein is a compound comprising the chemical structure of formula I, wherein the lanthanide metal is Eu, Gd, or Yb.

In certain embodiments, provided herein is a compound comprising the chemical structure of formula I, wherein $R_3$, $R_4$, and $R_5$ are hydrogen.

In certain embodiments, provided herein is a compound comprising the chemical structure of formula I, wherein the compound comprises a formula selected from the group consisting of:

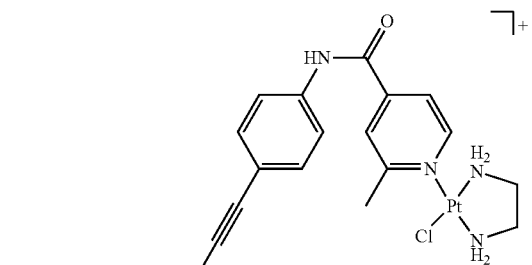

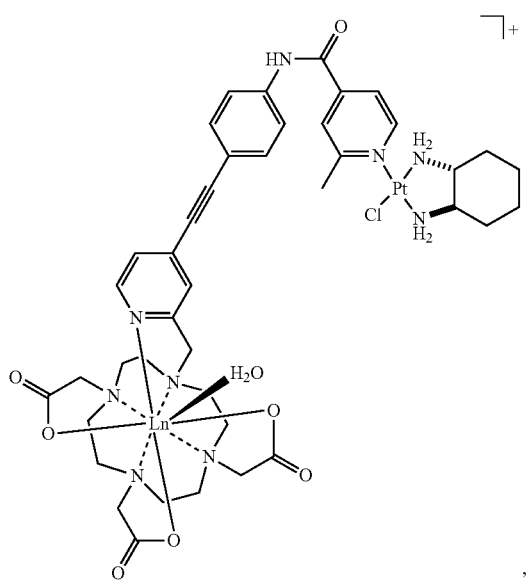

5
-continued
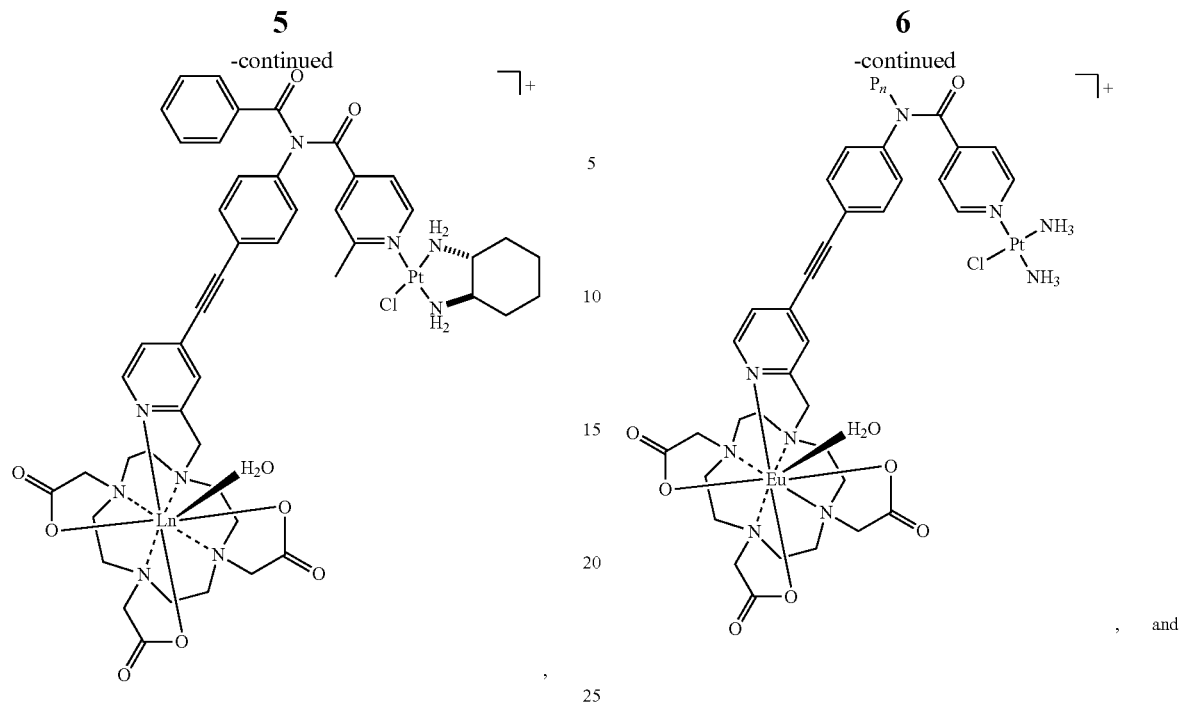
6
-continued
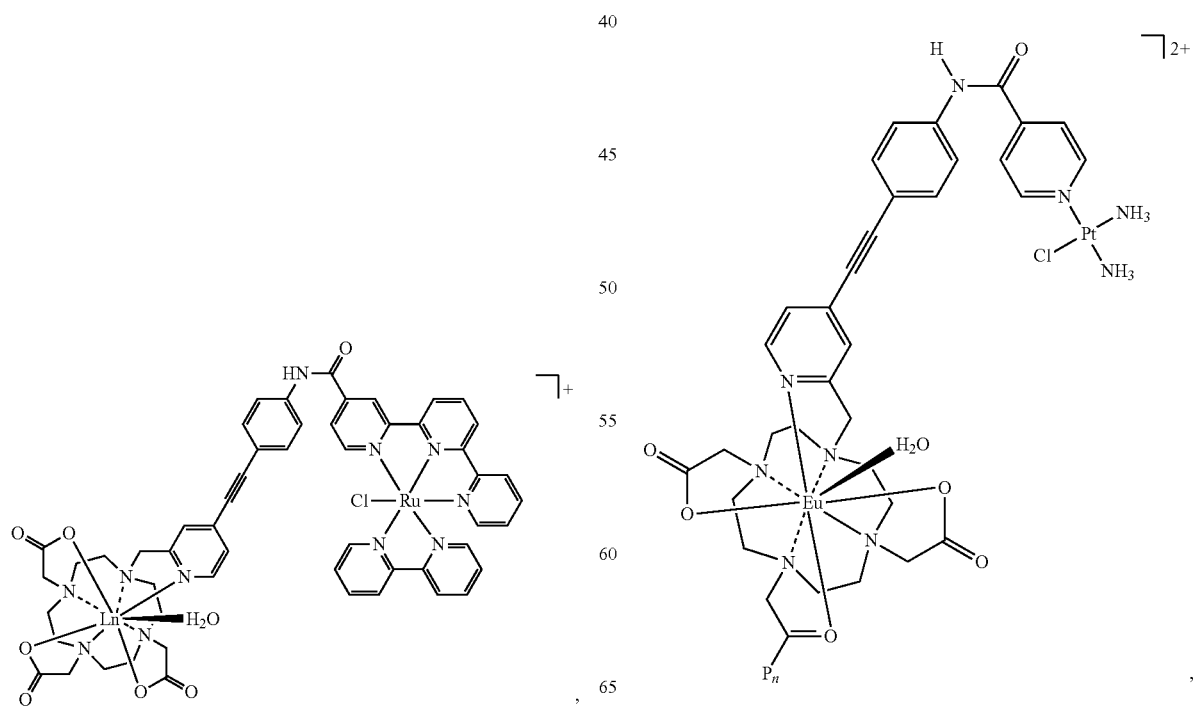
, and
wherein $P_n$ a polypeptide represented by SEQ ID NO: 1.

In certain embodiments, provided herein is a compound comprising a chemical structure of formula (II):

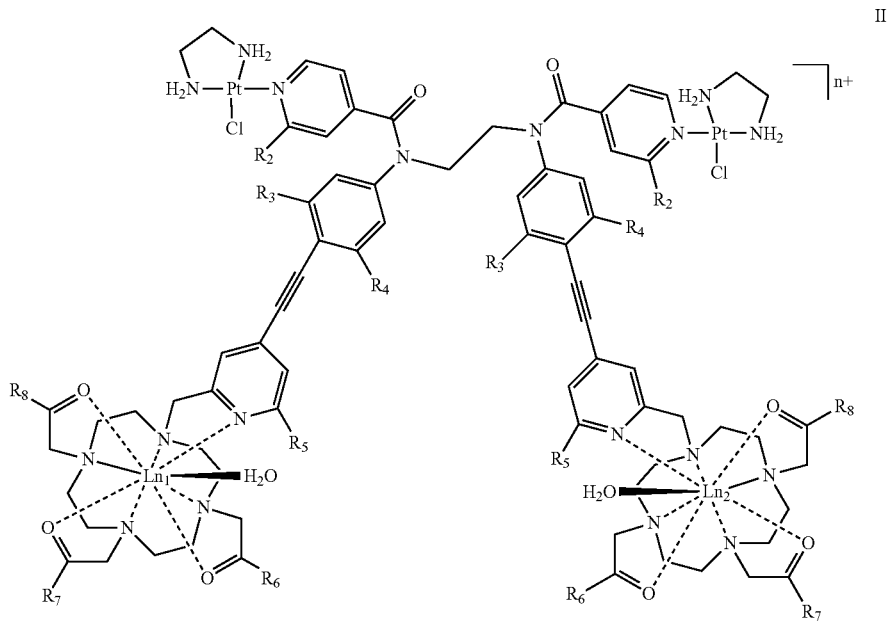

wherein, Ln$_1$ is Eu or Yb;

Ln$_2$ is Gd;

each instance of R$_2$ is independently hydrogen or alkyl;

each instance of R$_3$, R$_4$, and R$_5$ is independently H, OMe, NMe$_2$ or CF$_3$;

each instance of R$_6$, R$_7$, and R$_8$ is independently O$^-$ or P$_n$;

each instance of P$_n$ is a polypeptide is independently represented by SEQ ID NO: 1, 2, 3, 4, or 5; and n+ represents the net charge of the compound and is +2, +3, +4, or +5.

In certain embodiments, provided herein is a compound comprising the chemical structure of formula II, wherein R$_2$ is methyl, R$_3$, R$_4$, and R$_5$ are hydrogen; R$_6$, R$_7$, and R$_8$ are O$^-$; R$_2$ is methyl, R$_3$, R$_4$, and R$_5$ are hydrogen, R$_6$ and R$_7$ are O$^-$, and R$_5$ is P$_n$; or R$_2$ is methyl, R$_3$, R$_4$, and R$_5$ are hydrogen, R$_6$ and R$_5$ are O$^-$, and R$_7$ is P$_n$.

In certain embodiments, provided herein is a pharmaceutical composition comprising a compound of comprising the chemical formula I and at least one pharmaceutically acceptable excipient.

In certain embodiments, the pharmaceutical composition comprises a mixture of

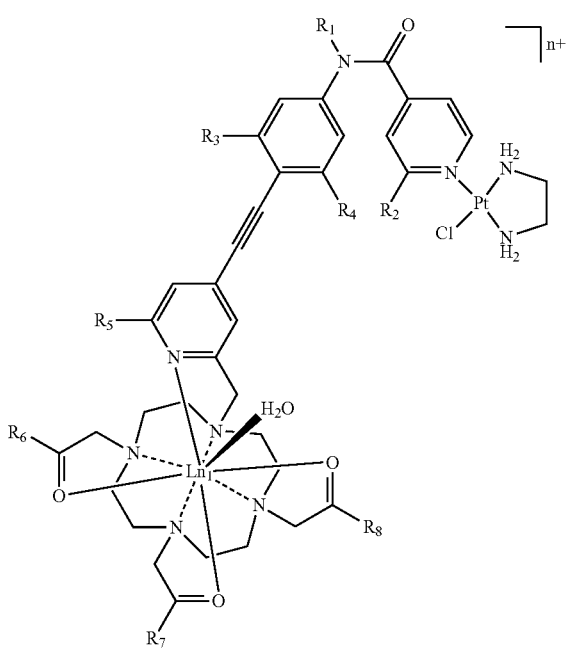

and

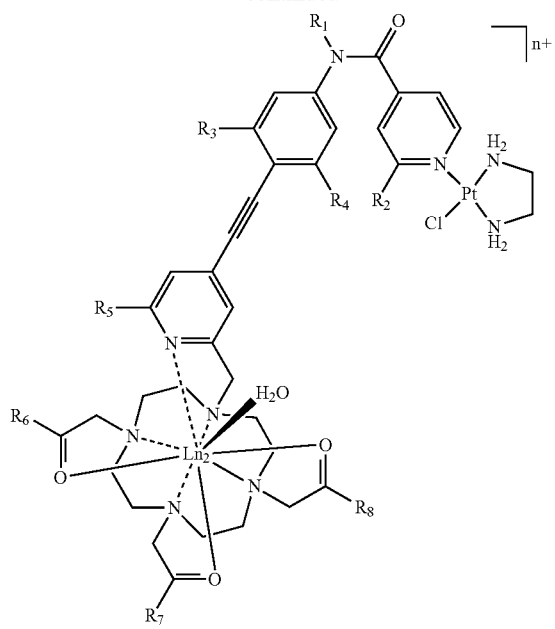

wherein Ln₁ is Eu or Yb; and Ln₂ is Gd.

In certain embodiments, provided herein is a method of treating, imaging, or imaging and treating cancer in a patient in need thereof; comprising the step of administering an effective amount of a compound of comprising the chemical formula I to the patient.

In certain embodiments, the cancer is bladder cancer, cervical cancer skin cancer, oral cancer, or prostate cancer.

In certain embodiments, the compound is selected from the group consisting of:

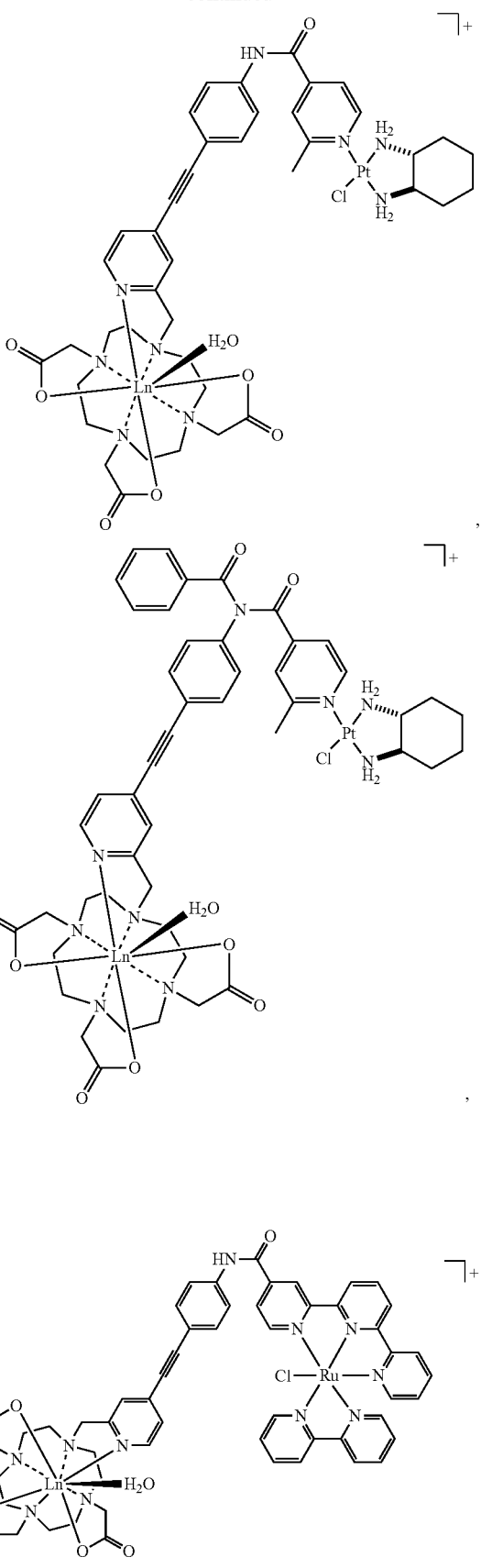

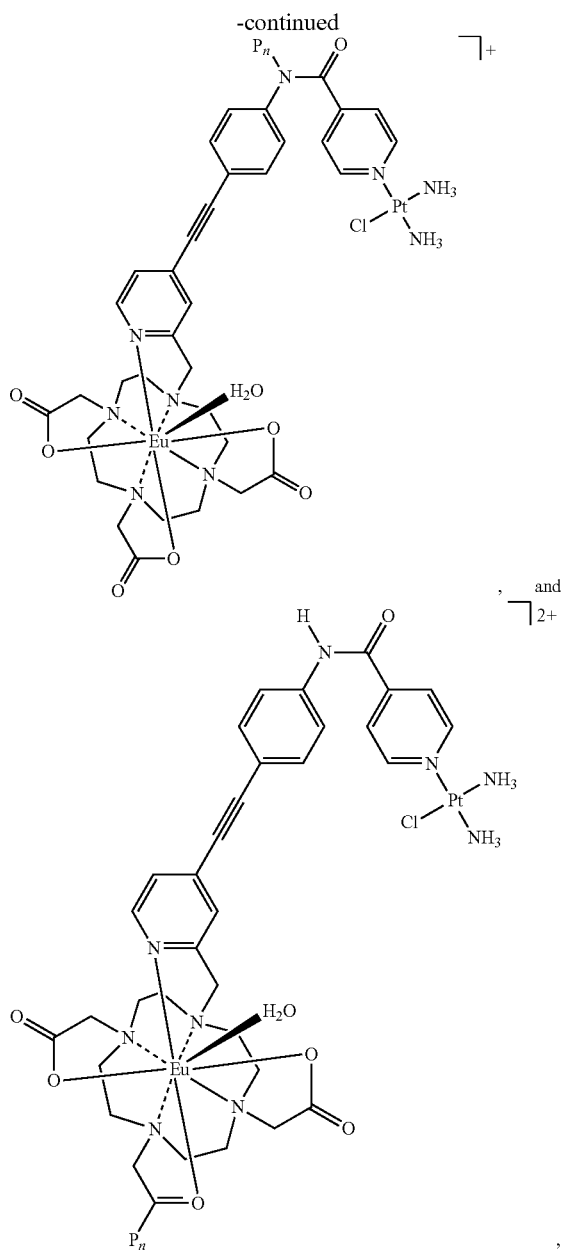

, and wherein $P_n$ a polypeptide represented by SEQ ID NO: 1.

The compounds disclosed herein are ionic species, which exist together with one or more counter-anions. The net charge of the compounds described herein and the counter-anions is zero. Any counter-anion can be used. Suitable examples, of counter-anions include, but are not limited to halides (such as chloride, bromide, and iodide), nitrate, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. In certain embodiments, the counter-anion is chloride, bromide, phosphate, acetate, sulfate, or a combination thereof.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The patent or application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, in which.

DETAILED DESCRIPTION OF THE INVENTION

The present disclosure is not to be limited in scope by any of the specific embodiments described herein. The following embodiments are presented for exemplification only.

The present disclosure relates, in part, to bladder cancer-specific prodrug agents and synthesized europium complexes for evaluating the binding with the integrin αvβ3.

The inventors have spent more than ten years investigating and exploring different ways to provide higher imaging quality for biomedical use with lanthanide-based coordination complexes/materials. These include NIR (up-conversion/multi-photon) excitation and the structure-localization relationship in vitro or in vivo.

Recently, the inventors have reported a 'proof-of-concept' study using a platinum-europium complex (PtEuL) which holds great promise as a controlled delivery vehicle of cisplatin. It shows real-time, responsive photo-triggered off-on switching behaviour, and lanthanide-based long-lived fingerprint emission triggered once cisplatin is photodissociated. The inventors report on the 'proof-of-concept' study is presented under the section titled Further Embodiments in this disclosure and is incorporated in its entirety herein.

However, the inventors' previous work still has room for improvement. For instance, the dark cytotoxicity of PtEuL in cancer cells is still rather high and without cancer cell selectivity; moreover, the UV excitation may not be penetrative enough for the intended in vivo studies. Near infrared (NIR) excitation light (800-1000 nm, i.e. American national standard—980 nm excitation with < than 0.73 W cm$^{-1}$ cw laser beam with 30-50 mm tissue penetration) makes it more effective in applications for the bioimaging and photodissociation of anticancer drugs. Developing a dual-imaging cisplatin carrying molecular cargo capable of performing simultaneous NIR-optical imaging, i.e. synergetic sensitive and high temporal-spatial resolution, does help scientists to study the real-time biodistribution and pharmacokinetics in situ more comprehensively and conveniently, in addition to aiding the evaluation of prodrug performance without autofluorescence interference and the need for additional control experiments.

Figure 1:
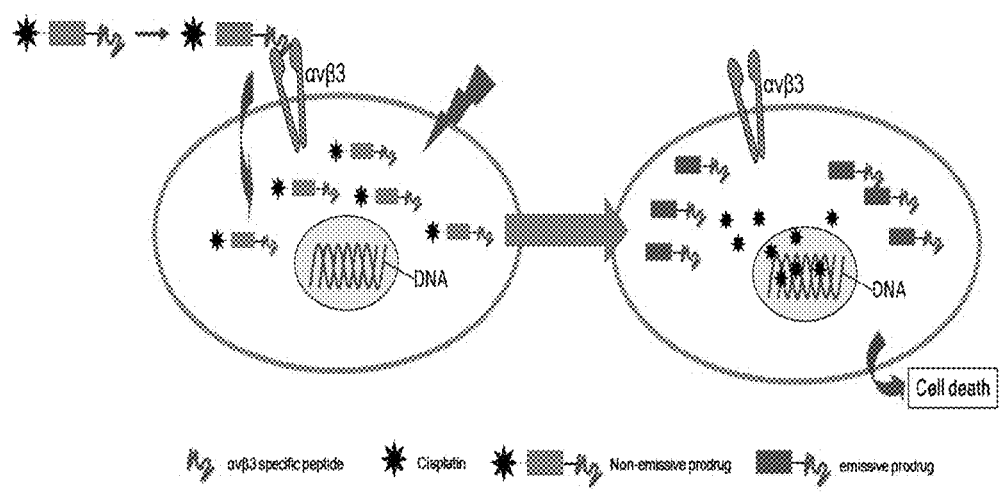
FIG. 1 shows the development of multi-modal water-soluble, lanthanide (europium/ytterbium/gadolinium)-based prodrug for optical/MRI imaging and inhibition of bladder cancer.
Figure 2:
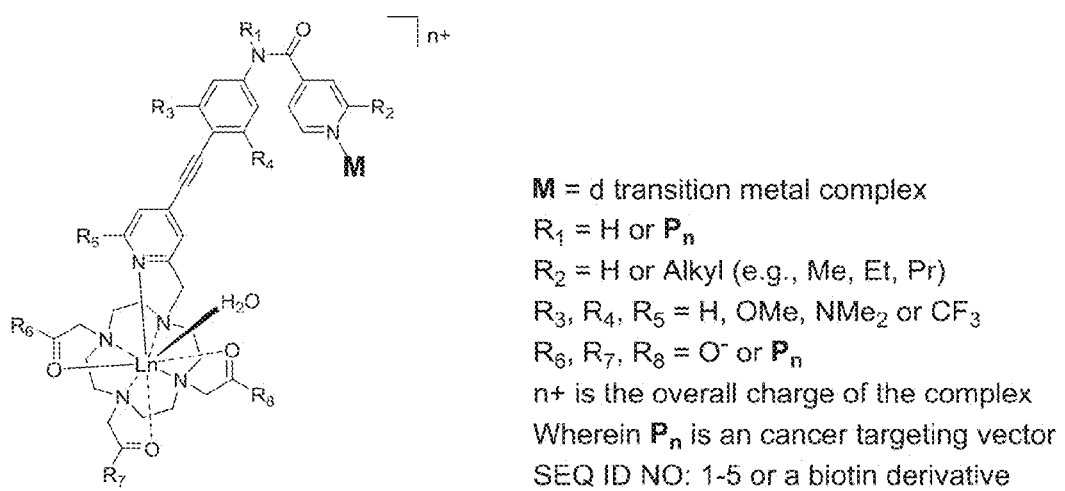
FIG. 2 shows an embodiment of the complexes described herein.

In the present invention, three different synthetic approaches develop practical multimodal theranostic prodrugs (FIG. 1). The cell-permeable and water-soluble cyclen-based europium complexes are to be bioconjugated with a photo/enzymatic dissociable moiety and cancer-specific vector (peptide); Pt(II)/Ru(II) based active drug will be synthesized and evaluated comprehensively in-vitro and in-vivo. For cancer selection, future studies of photoactivatable prodrug will focus on skin/oral/prostate/bladder cancer. The inventors would like to trace the integrin αvβ3 isoform in bladder cancer, thereby developing bladder cancer-specific prodrug agents in the longer term. Bladder cancer has been chosen as it is a high-risk cancer that spreads to other parts of the urinary tract and therefore it has great potential in becoming a candidate for early-stage treatment.

The first aspect of the present invention, there is provided a compound for theranostic prodrugs comprising lanthanide-based complexes with a formulation of (I)

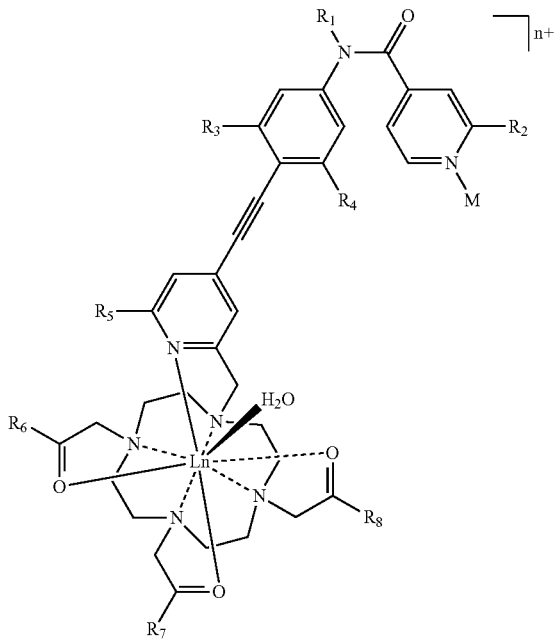

(FIG. 2)

Ln = Eu, Gd, Yb or other lanthanide elements
M = d transition metal complex
R$_1$ = H or P$_n$
R$_2$ = H or Alkyl (e.g., Me Et, Pr)
R$_3$, R$_4$, R$_5$ = H, OMe, NMe$_2$ or CF$_3$
R$_6$, R$_7$, R$_8$ = O$^-$ or P$_n$
n+ is the overall charge of the complex
Wherein P$_n$ is an cancer targeting vector
SEQ ID NO: 1-5 or a biotin derivative wherein Ln is Eu, Gd, Yb, or other lanthanide element;

wherein $P_n$ is a cancer targeting vector such as integrin αvβ3 isoform specific peptides comprising wherein $P_n$ (where n=1-6)=$P_1$: -Ahx-cGRLKEKKc-RrRk (SEQ ID NO:1); $P_2$: -Ahx-cQKGGRKHc-RrRk (SEQ ID NO:1); $P_3$: -Ahx-cM-KKHGKRc-RrRk (SEQ ID NO:3); $P_4$: -Ahx-cFDDFGc-RrRk (SEQ ID NO:4); $P_5$: -Ahx-cQDGRMGFc-RrRk (SEQ ID NO:5); $P_6$: biotin derivative, such as:

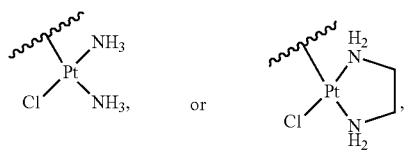

and

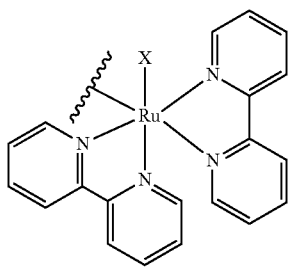

;

wherein $R_n$ (where n=1 to 8), and wherein d transition metal complex M=

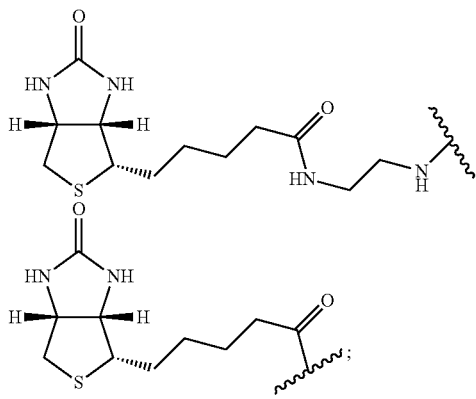

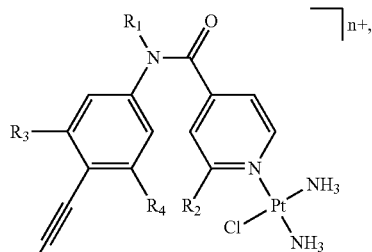

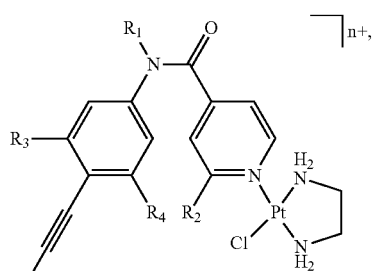

Pt—Ln—$L_1$—$R_n$

Pt—Ln—$L_2$—$R_n$ wherein X=Cl or OH.

In a first embodiment of the first aspect of the present invention, there is provided a compound for theranostic prodrugs comprising lanthanide-based complexes with a formulation of (I) wherein said lanthanide-based complexes further comprising a formulation of -continued

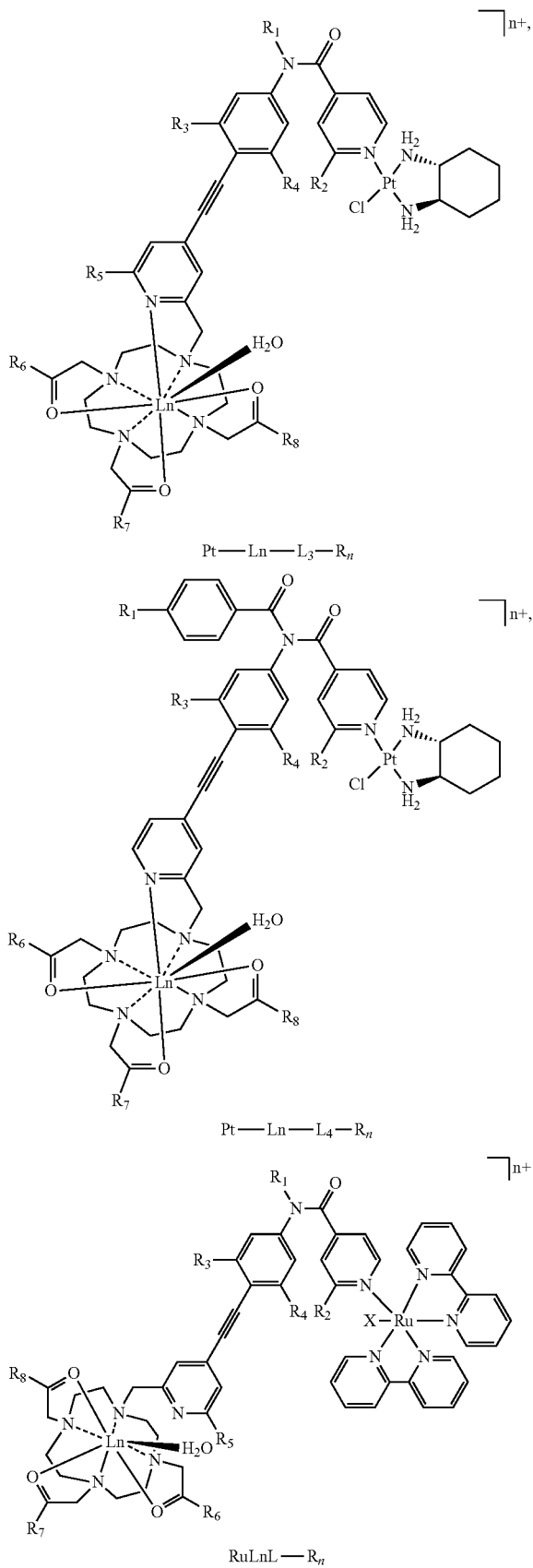

Pt—Ln—L$_3$—R$_n$

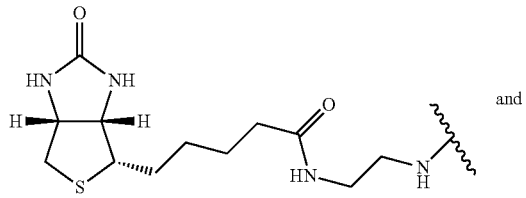

Pt—Ln—L$_4$—R$_n$

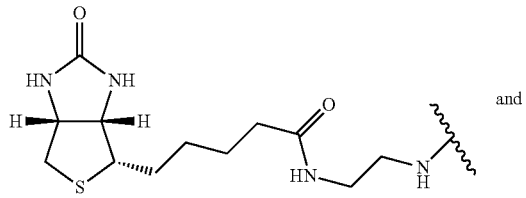

RuLnL—R$_n$

Wherein L1 refer to the complexes have similar ligand in the lanthanide part and the ligands of platinum part are NH$_3$, NH$_3$ and Cl); wherein L$_2$ refer to the ligands of platinum part contain a ethylenediamine ligand and a Cl ligand; wherein L$_3$ refer to the ligands of platinum part contain a (1R,2R)-cyclohexane-1,2-diamine ligand and a Cl ligand; wherein L$_4$ is a variation of L$_3$ which similar pt part but the lanthanide part contain a benzamide substituent.

wherein Ln=Eu or Gd or Yb or other lanthanide elements; wherein R$_1$=H or P$_n$;

wherein R$_2$=H or P$_n$; wherein R$_3$, R$_4$, R$_5$=H, OMe, NMe$_2$ or CF$_3$; wherein R$_6$, R$_7$, R$_8$=O$^-$ or P$_n$; wherein m+ is the overall charge of the complexes; wherein Ln=Eu or Gd or Yb or other lanthanide elements and wherein P$_n$ is an cancer targeting vector such as integrinαvβ3 isoform specific peptides comprising wherein P$_n$ (wheren=1-6), (P$_1$: -Ahx-cGRLKEKKc-RrRk; P$_2$: -Ahx-cQKGGRKHc-RrRk; P$_3$: -Ahx-cMKKHGKRc-RrRk; P$_4$: -Ahx-cFDDFGc-RrRk; P$_5$: -Ahx-cQDGRMGFc-RrRk; P$_6$: biotin derivative, such as:

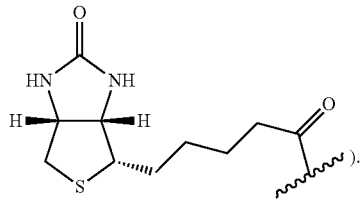

In a second embodiment of the first aspect of the present invention, there is provided a compound for theranostic prodrugs comprising lanthanide-based complexes with a formulation of (I) wherein said lanthanide-based complexes comprising a formulation of 21 22

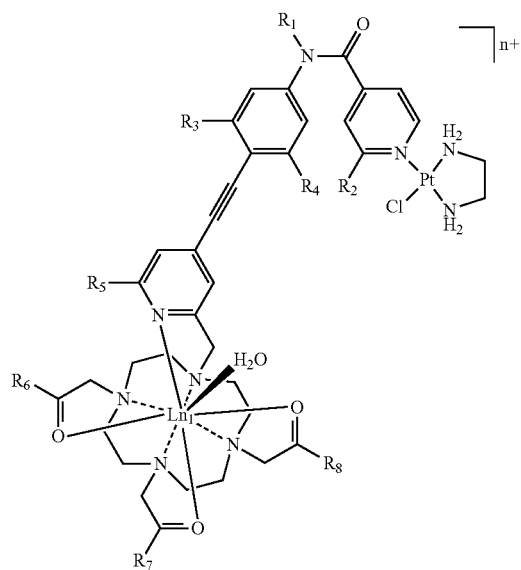
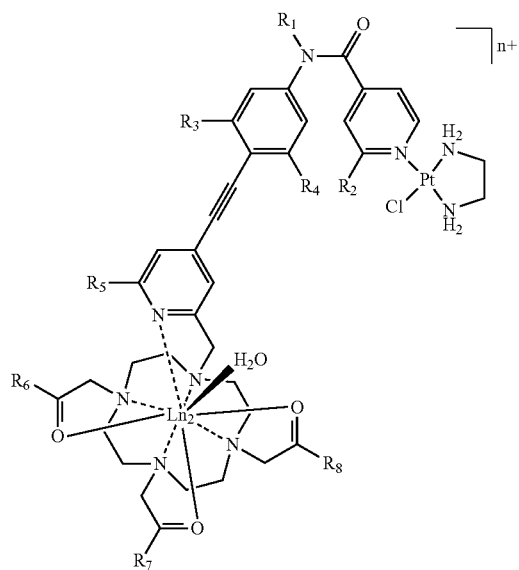

Ln₁ = Eu(or Yb) and Ln₂ = Gd
Hybrid Eu(or Yb):Gd = 50:50

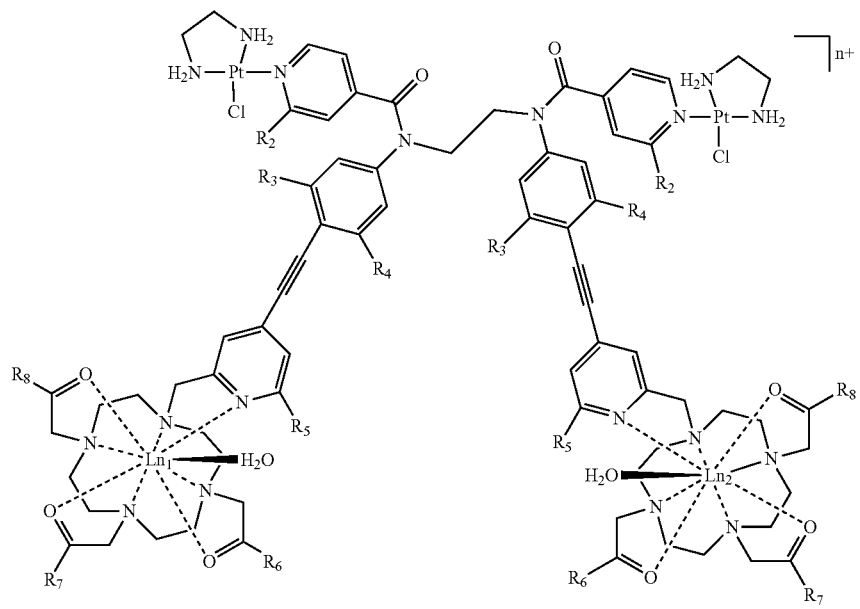

Dimetric Ln₁ = Eu(or Yb) and Ln₂ = Gd wherein $R_1$=H or $P_n$; wherein $R_2$=H or $P_n$; wherein $R_3$, $R_4$, $R_5$=H, OMe, NMe$_2$ or CF$_3$; wherein $R_6$, $R_7$, $R_8$=O⁻ or $P_n$; wherein m+ is the overall charge of the complexes; wherein Ln=Eu or Gd or Yb or other lanthanide elements and wherein $P_n$ is an cancer targeting vector such as integrinαvβ3 isoform specific peptides comprising wherein $P_n$ (n=1-6), ($P_1$: -Ahx-cGRLKEKKc-RrRk (SEQ ID NO:1); $P_2$: -Ahx-cQKGGRKHc-RrRk (SEQ ID NO:2); $P_3$: -Ahx-cMKKHGKRc-RrRk (SEQ ID NO:3); $P_4$: -Ahx-cFDDFGc-RrRk (SEQ ID NO:4); $P_5$: -Ahx-cQDGRMGFc-RrRk (SEQ ID NO:5); $P_6$: such as:

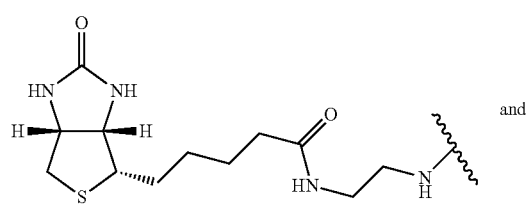

and

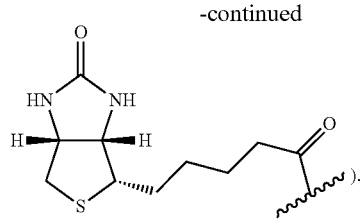
In a third embodiment of the first aspect of the present invention, there is provided a compound for theranostic prodrugs comprising lanthanide-based complexes with a formulation of (I) wherein said lanthanide-based complexes comprising a formulation of
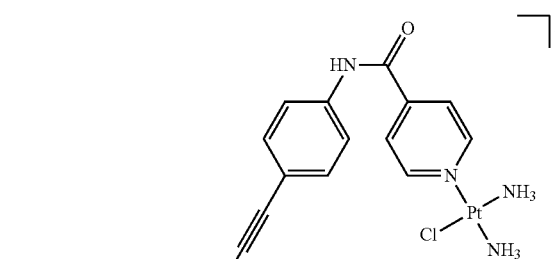
PtLnL
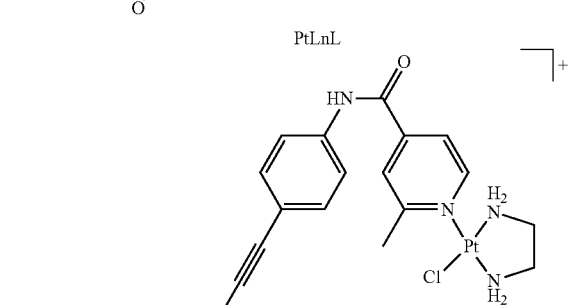
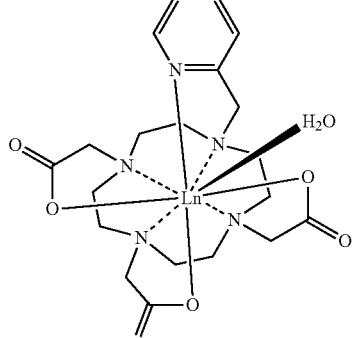
Pt—Ln—L$_2$
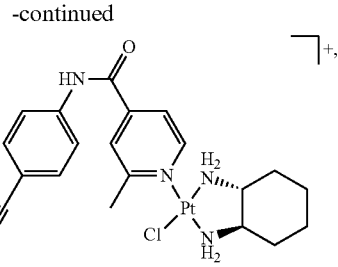
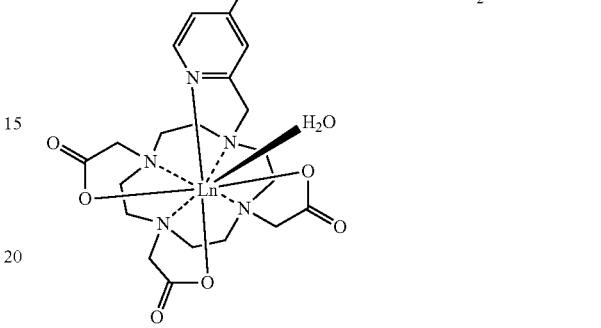
Pt—Ln—L$_3$
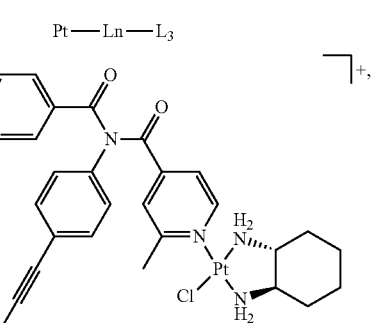
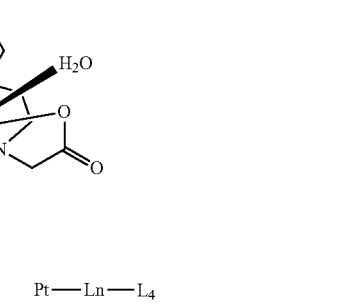
Pt—Ln—L$_4$
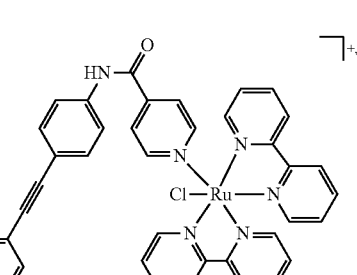
RuLnL -continued

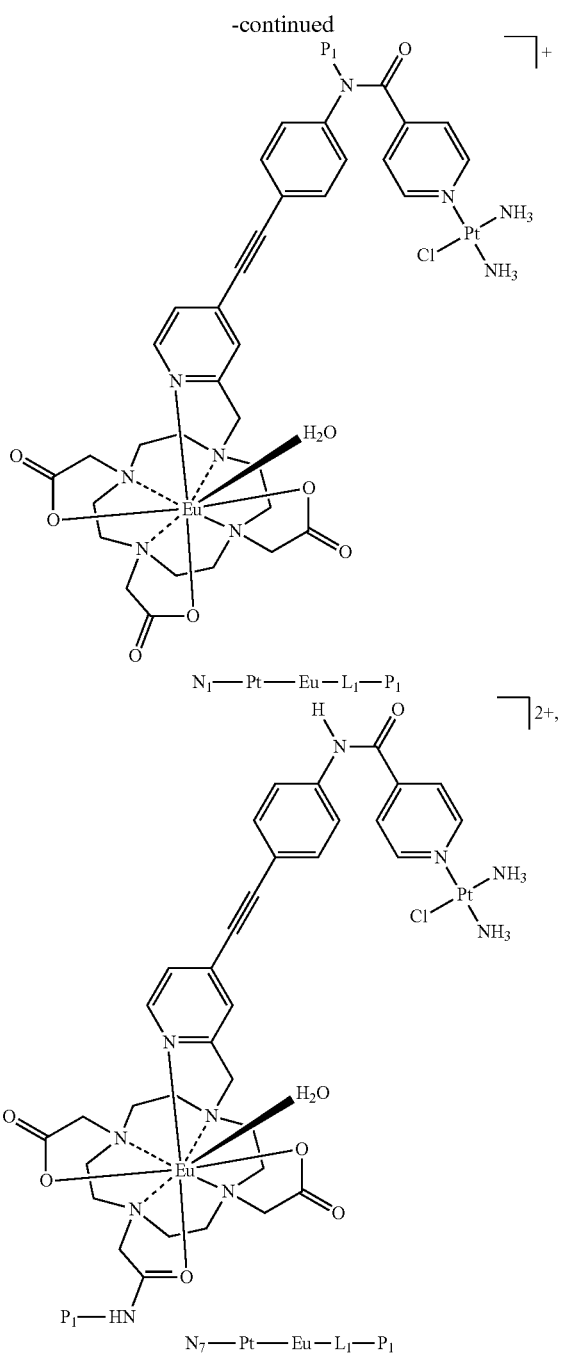

$N_1$—Pt—Eu—$L_1$—$P_1$ wherein Ln is Eum Gd, Yb, or other lathanide elements. N refer to N side of the cyclen macmrocyclic ligand; and N7 refer to N7 side of the cyclen.

In a second aspect of the present disclosure, there is provided a compound with a formulation of (I) wherein said compound is a fluorescence imaging or MRI or photo-dissociable theranostic prodrug.

In a third aspect of the present disclosure, there is provided a compound with a formulation of (I) wherein said compound is a fluorescence imaging and MRI and photo-dissociable theranostic prodrug.

In a fourth aspect of the present disclosure, there is provided a compound with a formulation of (I) wherein said compound is a theranostic prodrug for treating bladder cancer or cervical cancer.

In a fifth aspect of the present disclosure, there is provided a use of the compound with a formulation of (I) for treating bladder cancer or cervical cancer.

In a first embodiment of the fifth aspect of the present disclosure, there is provided a use of the compound with a formulation of (I) wherein the compound is administered via intravenous injection.

In a sixth aspect of the present disclosure, there is provided a use of the compound with a formulation of (I) for imaging bladder cancer or cervical cancer.

In a first embodiment of the sixth aspect of the present disclosure, there is provided a use of the compound with a formulation of (I) wherein the compound is administered via intravenous injection.

In a seventh aspect of the present disclosure, there is provided a use of the compound with a formulation of (I) for treating superficial malignancy comprising skin cancer, oral cancer and prostate cancer.

In a first embodiment of the seventh aspect of the present disclosure, there is provided a use of the compound with a formulation of (I) wherein the compound is administered via intravenous injection.

In an eighth aspect of the present disclosure, there is provided a use of the compound with a formulation of (I) for imaging superficial malignancy comprising skin cancer, oral cancer and prostate cancer.

In a first embodiment of the eighth aspect of the present disclosure, there is provided a use of the compound with a formulation of (I) wherein the compound is administered via intravenous injection.

In a ninth aspect of the present disclosure, there is provided a compound comprising a chemical structure of formula (I):

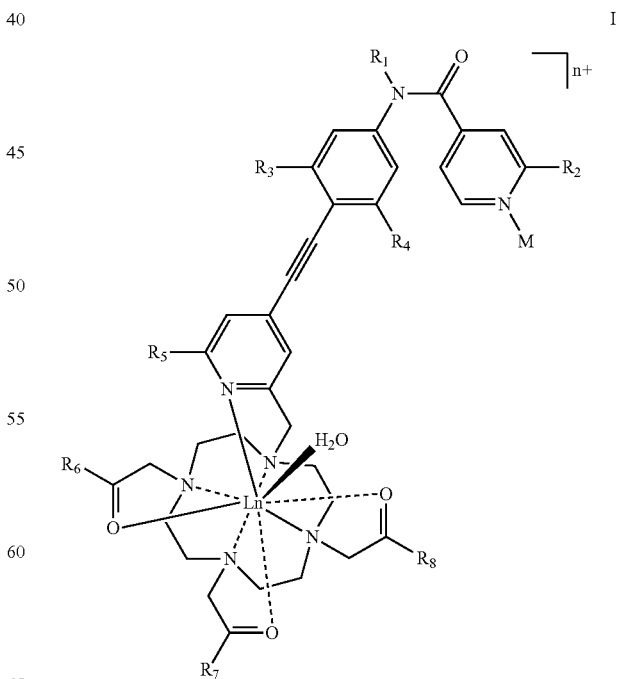

I wherein Ln is a lanthanide metal;

$R_1$ is independently hydrogen, $P_n$,

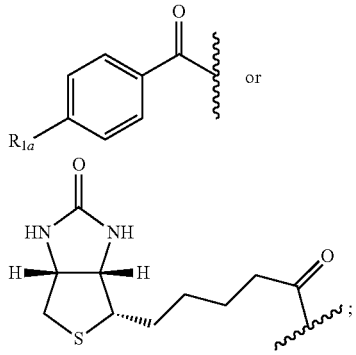

$R_{1a}$ is hydrogen or $P_n$;

$R_2$ is hydrogen or alkyl;

each of $R_3$, $R_4$ and $R_5$ is independently hydrogen, OMe, NMe$_2$, or CF$_3$;

each of $R_6$, $R_7$ and $R_8$ is independently O$^-$, $P_n$, or

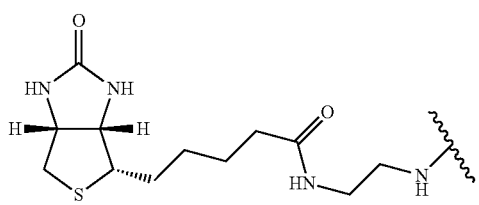 [SMILES: *NCCNC(=O)CCCC[C@@H]1SC[C@@H]2NC(=O)N[C@@H]21]

$P_n$ is a polypeptide represented by SEQ ID NO: 1, 2, 3, 4, or 5;

M represents a moiety selected from the group consisting of:

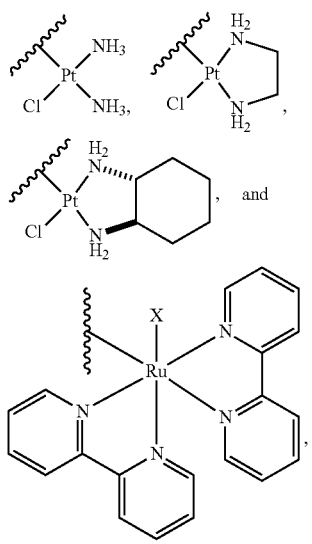

wherein X is Cl or OH; and n+ represents the net charge of the compound and is +1, +2, +3, or +4; with the proviso that if M is

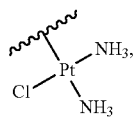

then $R_2$ is alkyl or at least one of $R_1$, $R_{1a}$, $R_6$, $R_7$, and $R_8$, is $P_n$.

In a first embodiment of the ninth aspect, provided is a compound, wherein the compound comprising a chemical structure of formula (I) does not have the formula Ia:

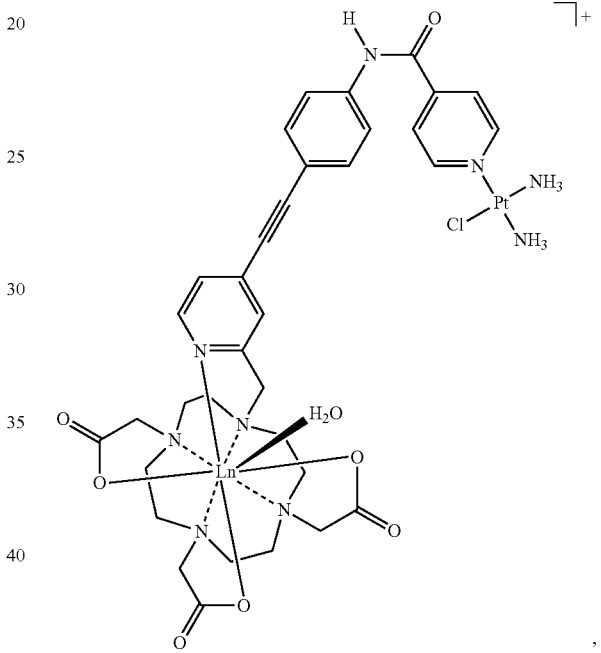

Ia wherein Ln is a lanthanide metal. In certain embodiments Ln is Eu or Gd.

In a second embodiment of the ninth aspect, there is provided a compound, wherein $R_1$ is $P_n$ and $R_6$, $R_7$ and $R_8$ are O$^-$; $R_1$ is H, $R_6$ and $R_7$ are O$^-$, and $R_8$ is $P_n$; or $R_1$ is H, $R_6$ and $R_1$ are O$^-$, and $R_7$ is $P_n$; or $R_1$ is H and $R_6$, $R_7$ and $R_8$ are O$^-$.

In a third embodiment of the ninth aspect, there is provided a compound, wherein $R_2$ is methyl or at least one of $R_1$, $R_6$, $R_7$, or $R_8$ is $P_n$.

In a fourth embodiment of the ninth aspect, there is provided a compound, wherein the lanthanide metal is Eu, Gd, or Yb.

In a fifth embodiment of the ninth aspect, there is provided a compound, wherein $R_3$, $R_4$, and $R_5$ are hydrogen.

In a sixth embodiment of the ninth aspect, there is provided a compound, wherein the compound comprises a formula selected from the group consisting of:

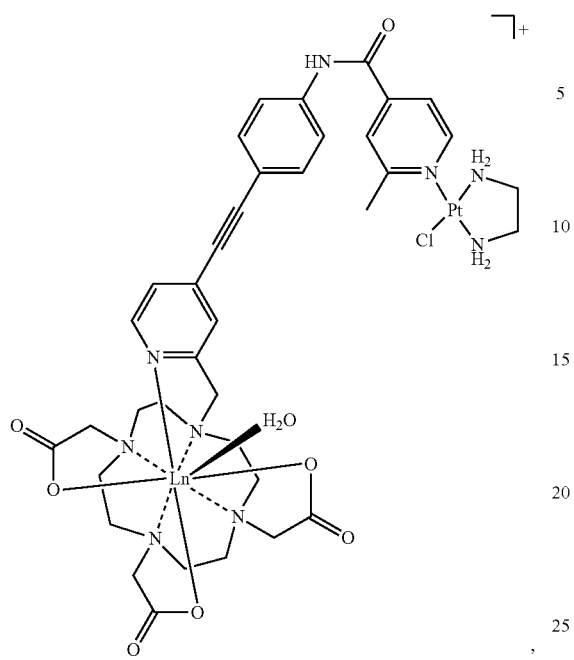
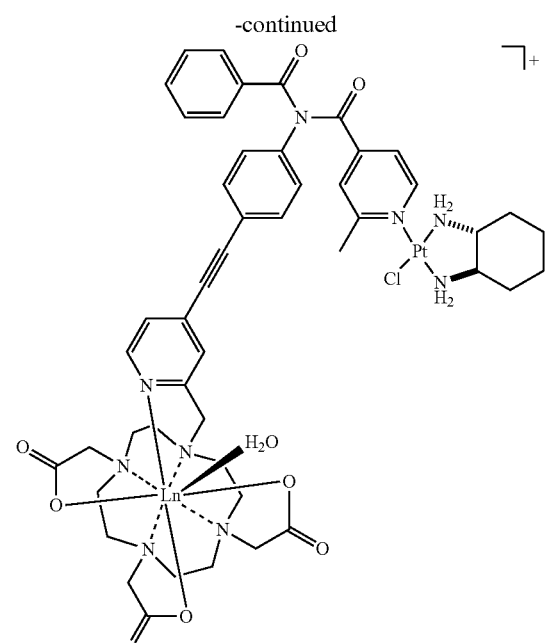
-continued
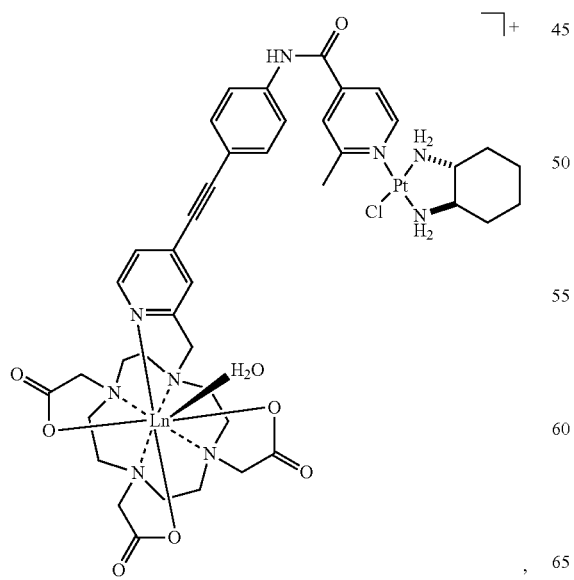
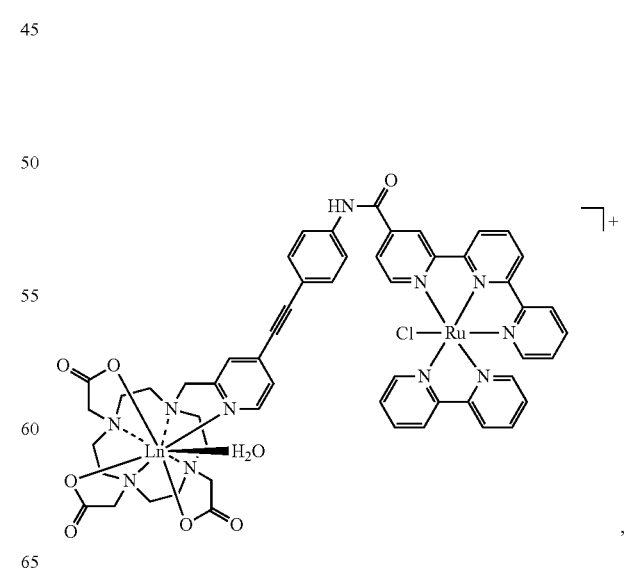

31
-continued
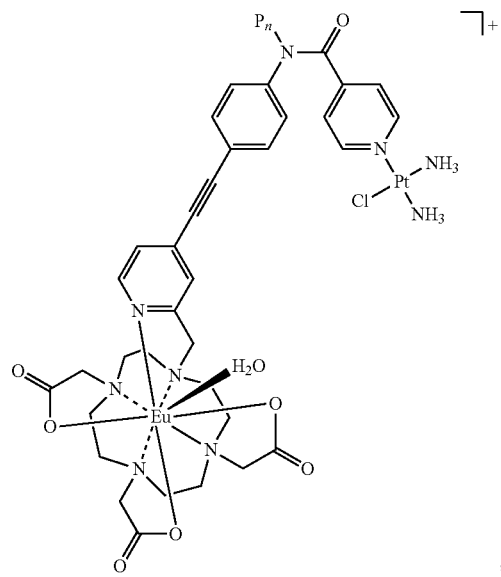
, and
32
-continued
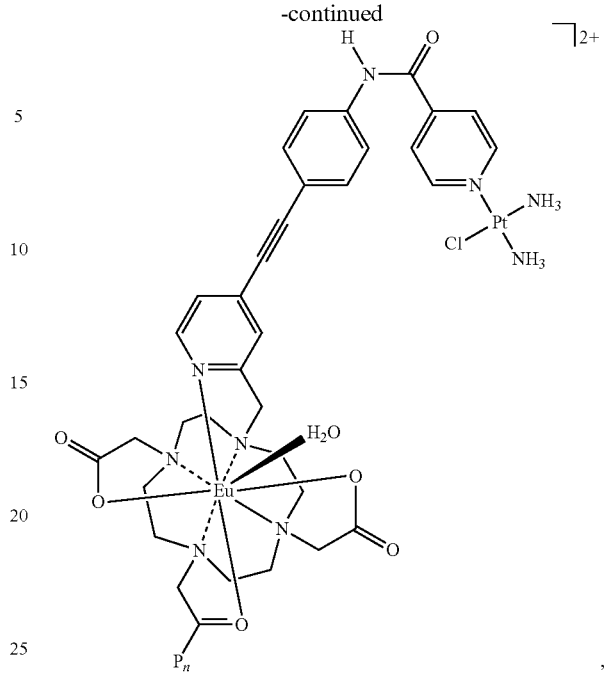
wherein $P_n$ a polypeptide represented by SEQ ID NO: 1.
In a tenth aspect of the present disclosure, there is provided a compound comprising a chemical structure of formula (II):
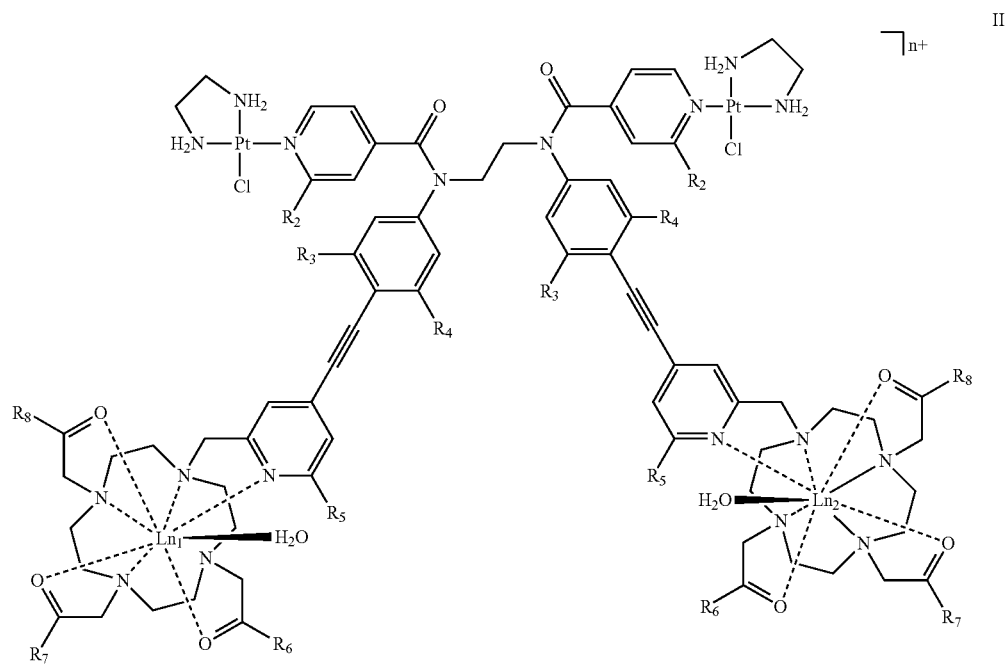

wherein, $Ln_1$ is Eu or Yb;

$Ln_2$ is Gd;

each instance of $R_2$ is independently hydrogen or alkyl;

each instance of $R_3$, $R_4$, and $R_5$ is independently H, OMe, $NMe_2$ or $CF_3$;

each instance of $R_6$, $R_7$, and $R_8$ is independently $O^-$ or $P_n$;

each instance of $P_n$ is a polypeptide is independently represented by SEQ ID NO: 1, 2, 3, 4, or 5; and n+ represents the net charge of the compound and is +2, +3, +4, or +5.

In a first embodiment of the tenth aspect, there is provided a compound, wherein $R_2$ is methyl, $R_3$, $R_4$, and $R_5$ are hydrogen; $R_6$, $R_7$, and $R_8$ are $O^-$; $R_2$ is methyl, $R_3$, $R_4$, and $R_5$ are hydrogen, $R_6$ and $R_7$ are $O^-$, and $R_8$ is $P_n$; or $R_2$ is methyl, $R_3$, $R_4$, and $R_5$ are hydrogen, $R_6$ and $R_8$ are $O^-$, and $R_7$ is $P_n$.

In an eleventh aspect of the present disclosure, there is provided a pharmaceutical composition comprising a compound of claim 1 and at least one pharmaceutically acceptable excipient.

In a first embodiment of the eleventh aspect, there is provided a pharmaceutical composition comprising a mixture of

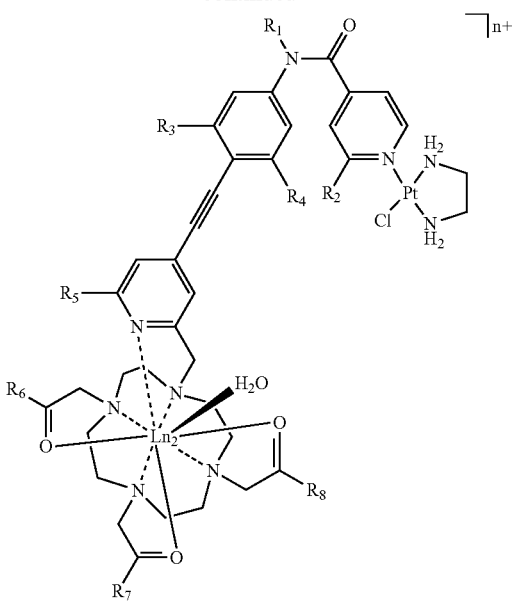

wherein $Ln_1$ is Eu or Yb; and $Ln_2$ is Gd.

In a twelfth aspect of the present disclosure, there is provided a method of treating, imaging, or imaging and treating cancer in a patient in need thereof, comprising the step of administering an effective amount of a compound of claim 1 to the patient.

In a first embodiment of the twelfth aspect, there is provided a method, wherein the cancer is bladder cancer, cervical cancer skin cancer, oral cancer, or prostate cancer.

In a second embodiment of the twelfth aspect, there is provided a method, wherein the compound is selected from the group consisting of:

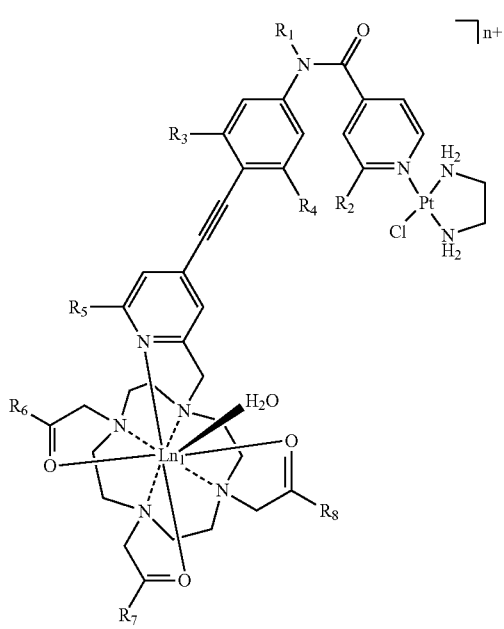

and

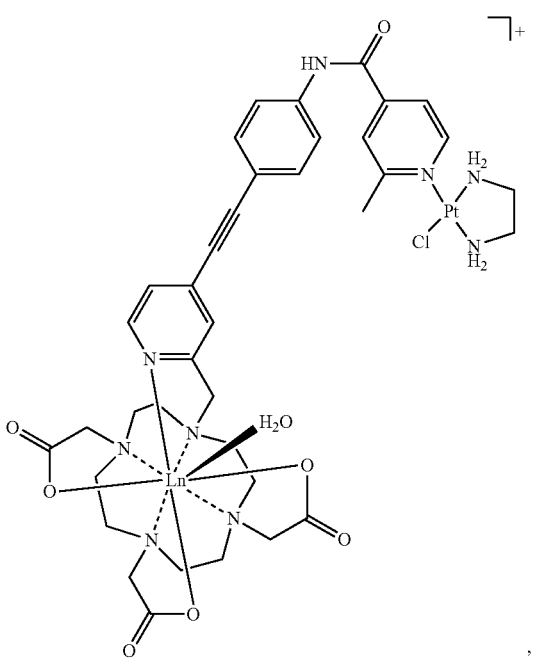

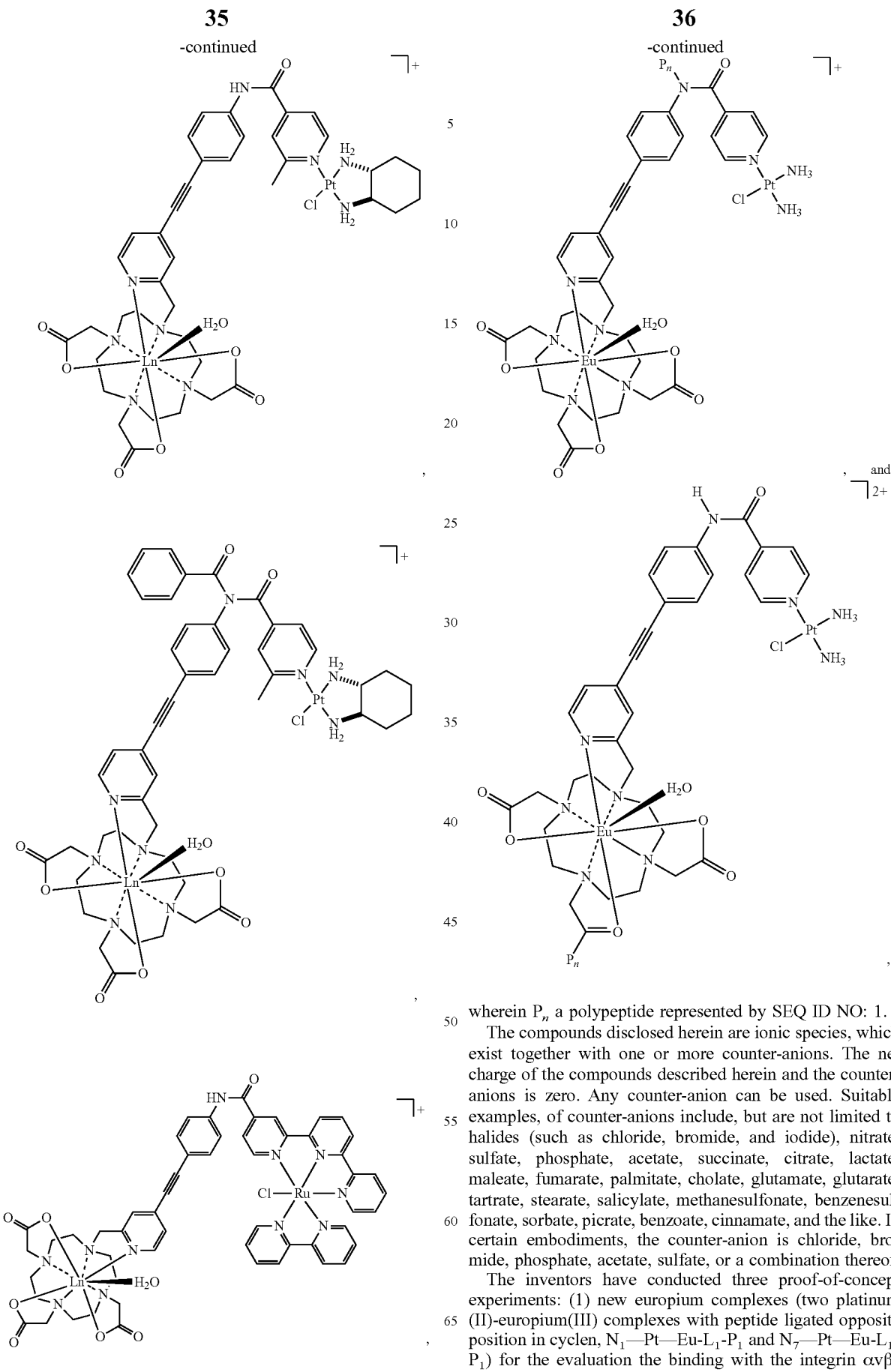

wherein $P_n$ a polypeptide represented by SEQ ID NO: 1.

The compounds disclosed herein are ionic species, which exist together with one or more counter-anions. The net charge of the compounds described herein and the counter-anions is zero. Any counter-anion can be used. Suitable examples, of counter-anions include, but are not limited to halides (such as chloride, bromide, and iodide), nitrate, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. In certain embodiments, the counter-anion is chloride, bromide, phosphate, acetate, sulfate, or a combination thereof.

The inventors have conducted three proof-of-concept experiments: (1) new europium complexes (two platinum (II)-europium(III) complexes with peptide ligated opposite position in cyclen, $N_1$—Pt—Eu-$L_1$-$P_1$ and $N_7$—Pt—Eu-$L_1$-$P_1$) for the evaluation the binding with the integrin $\alpha v \beta_3$ isoform have been synthesized. The design of each complex has been selected following molecular docking experiments. (2) The selectivity towards bladder cancer was confirmed by MTT assays and preliminary in-vitro imaging studies. (3) The photo-induced quantitative delivery assays have been undertaken comparing light dosed-emission intensity with -cisplatin content establishing the linearity of this relationship.

In the long term, the inventors envisage incorporation of these photodissociation prodrugs, capable of imaging uses, with different vectors to help enhance their target specificity. It is proposed to systematically develop several lanthanide complexes as responsive biomedical probes for targeting and monitoring of the disease and, in addition, delivering the anticancer prodrugs in vitro, in situ and in vivo as a result of the combination of biochemical, molecular and structural chemistry approaches. Further transformation with multimodal (magnetic and optical) capacity can be easily achieved, by introduction of gadolinium (e.g. for MRI contrast imaging work) as a hybrid/dimeric complex.

Figure 3:
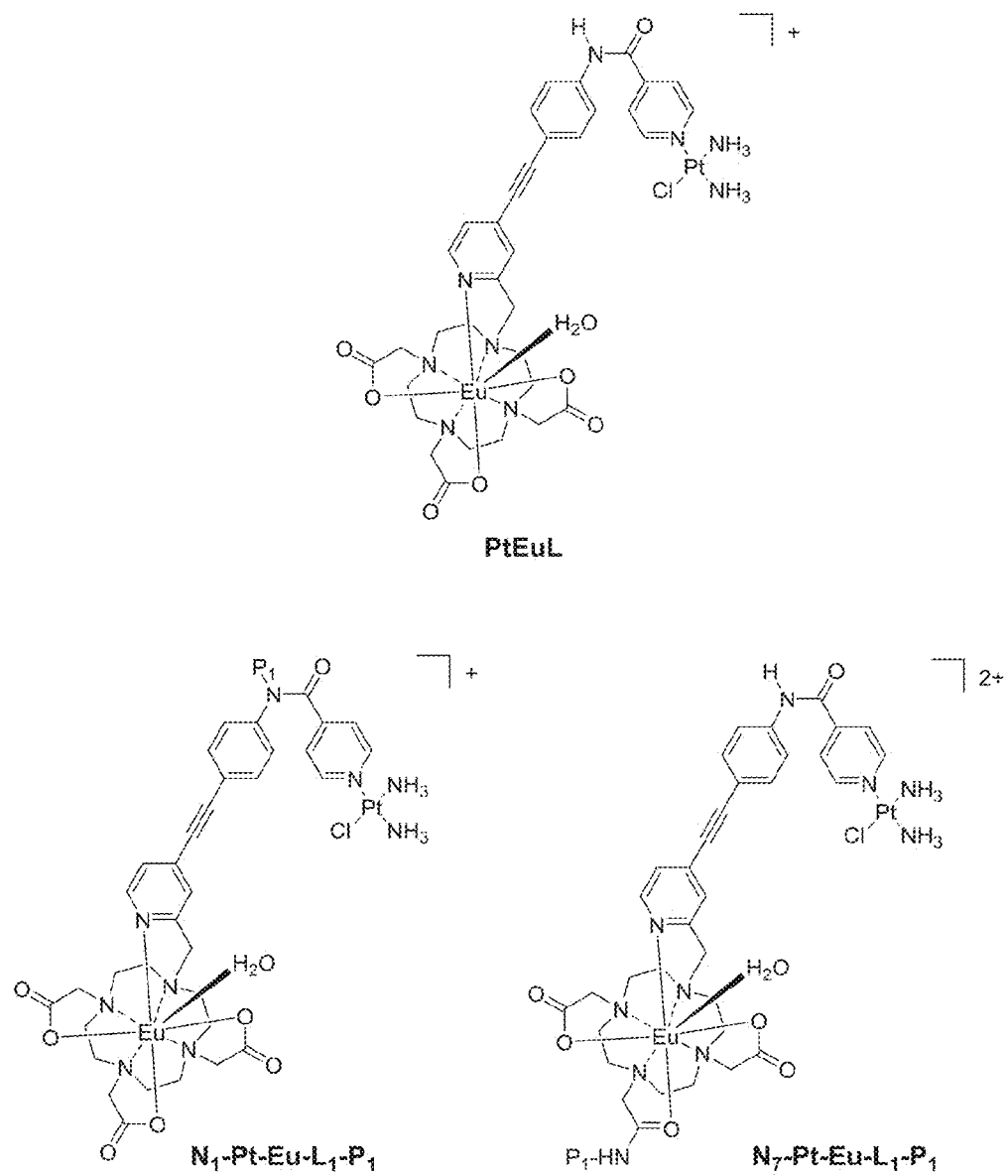
FIG. 3 shows chemical structures of prodrugs PtEuL, $N_1$—Pt-En-$L_1$-$P_1$ and $N_7$—Pt—Eu-$L_1$-$P_1$.
Figure 4:
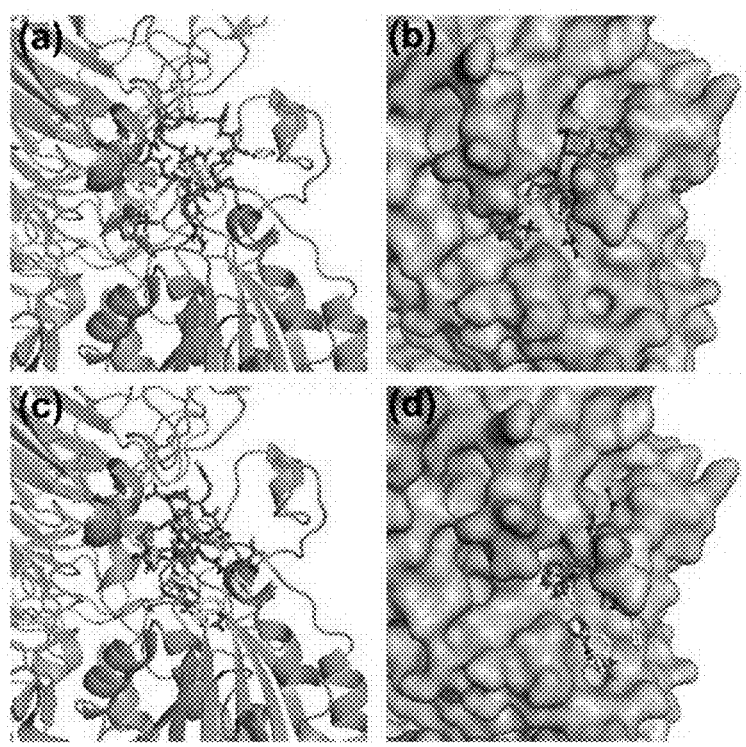
FIG. 4 shows preliminary data of molecular docking of $N_1$—Pt—Eu-$L_1$-$P_1$ (a and b) and $N_7$—Pt—Eu-$L_1$-$P_1$ with αvβ3 intergrin protein (c and d).
Figure 5A:
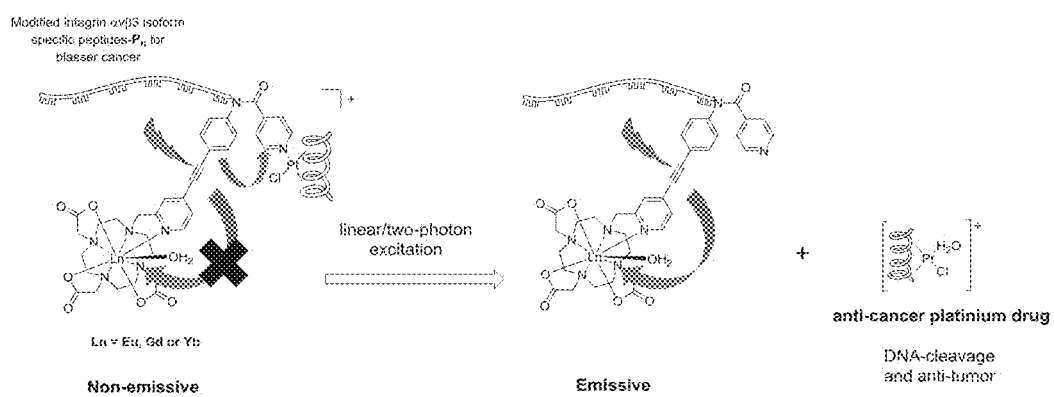
FIG. 5A shows the development of the dual probe for optical imaging and functionalization for a specific anticancer effect, via bioconjugation with known functional groups (for photodissociation) and peptides with other anti-cancer Pt moieties. ($P_n$=$P_1$: -Ahx-cGRLKEKKc-RrRk (SEQ ID NO:1); $P_2$: -Ahx-cQKGGRKHc-RrRk (SEQ ID NO:2); $P_3$: -Ahx-cMKKHGKRc-RrRk (SEQ ID NO:3); $P_4$: -Ahx-cFDDFGc-RrRk (SEQ ID NO:4); and $P_5$: -Ahx-cQDGRMGFc-RrRk (SEQ ID NO:5))
Figure 5B:
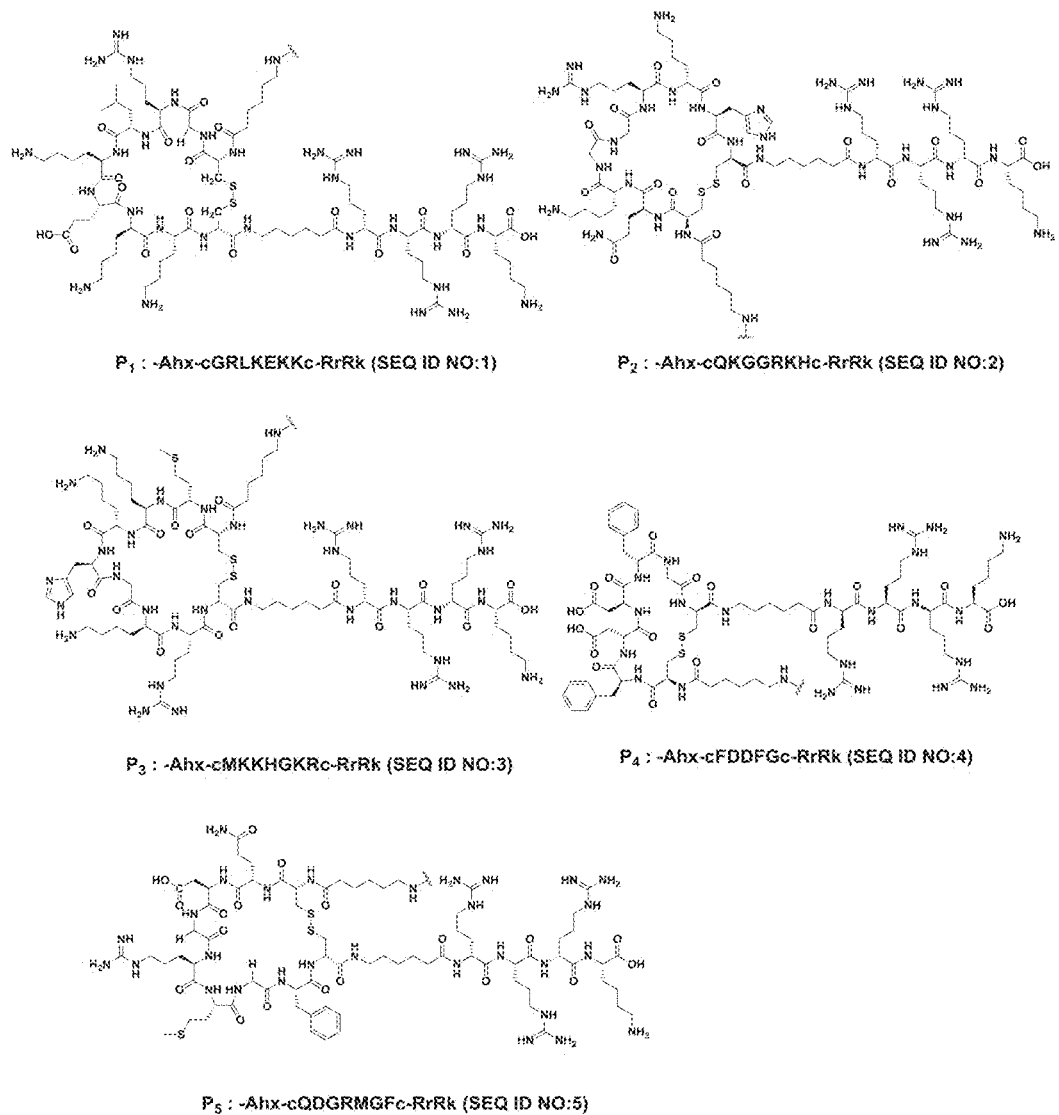
FIG. 5B shows the peptide structures for αvβ3 isoform. ($P_1$: -Ahx-cGRLKEKKc-RrRk (SEQ ID NO:1); $P_2$: -Ahx-cQKGGRKHc-RrRk (SEQ ID NO:2); $P_3$: -Ahx-cMKKHG- KRc-RrRk (SEQ ID NO:3); P$_4$: -Ahx-cFDDFGc-RrRk (SEQ ID NO:4); and P$_5$: -Ahx-cQDGRMGFc-RrRk (SEQ ID NO:5))

Three key 'proof-of-concept' studies have been undertaken done in support of the present invention:
1. Prof-of-concept study I: Real-time in situ monitoring via europium emission of the photo-release of antitumor cisplatin from a Eu—Pt complex
2. Prof-of-concept study II: Real-time Multi-Modal Monitoring of Drug Delivery by MRI and Fluorescence Imaging
3. Prof-of-concept study III: bladder cancer targeted prodrugs. Two new europium complexes have been synthesized ($N_1$—Pt—Eu-$L_1$-$P_1$ and $N_7$—Pt—Eu-$L_1$-$P_1$) for evaluating the binding with the integrin αvβ3 (FIG. 3); The design of each complex has been optimized following molecular docking simulations (FIG. 4).

Lanthanide Complexes/Materials with Peptide Chemistry for Imaging and Inhibition of Cancer Cyclin(s) and Plk1, involved in many key steps throughout mitosis, is found to be of great importance in cancer treatment since its activity appears to be limited to mitosis in proliferating cells. However, the lack of selective small-molecule inhibitors of the kinase remains a major obstacle to further elucidate its precise function. For instance, using anticancer agents that target microtubules may engender various adverse effects partially because of the diverse functions of microtubules in the cell. To date, only a few small molecules can show good specificity to Cyclin A/D/Plk1 for imaging and inhibition. The inventors have developed numerous lanthanide complexes/materials coupled with peptide chemistry to achieve the goal—imaging and targeted anti-tumor activity.

Development of Lanthanide-Based Photoactivated Cancer Therapy

Several novel organelle-specific markers (for lysosome, mitochondria, Golgi apparatus) have been synthesized. These complexes could simultaneously trigger the generation of singlet oxygen in vitro and give luminescent images of the organelles upon irradiation by visible/NIR excitation. Such behavior affords the highly sought-after goal of gaining spatial control using dual laser excitations to damage selected cell compartments/components.

Proof of Concept—NIR Sensitive Prodrug: Real-Time In Situ Monitoring Via Europium Emission of the Photo-Release of Antitumor Cisplatin from a Eu—Pt Complex The inventors have developed multi-modal lanthanide-based prodrugs for, e.g., NIR biological optical imaging—that bind strongly with a target integrin αvβ3 isoform; NIR excitation triggers the dissociation of cisplatin quantitatively.

i) Synthesis of the Bladder Cancer Specific Prodrug

The platinum complexes can be designed to target receptors expressed on cancer cells. For example, the integrin αvβ3 isoform can be targeted for the treatment of cancer, e.g., bladder cancer cell. The integrin αvβ3 isoform specific peptide ($P_1$—Ahx-cQDGRMGFc-RrRk) was conjugated to PtEuL (FIG. 3). The molecular docking stimulation studies of the two water soluble europium complexes ($N_1$—Pt—Eu-$L_1$-$P_1$ and $N_7$—Pt—Eu-$L_1$-$P_1$) with integrin αvβ3 isoform were carried out and showed that $N_1$—Pt—Eu-$L_1$-$P_1$ had better binding potential with integrin αvβ3 isoform protein than $N_7$—Pt—Eu-$L_1$-$P_1$. ($N_1$—Pt—Eu-$L_1$-$P_1$: ΔG=−11.2 kcal/mol$^{-1}$; $N_7$—Pt—Eu-$L_1$-$P_1$: ΔG−8.0 kcal/mol$^{-1}$) (FIG. 3).

The compounds disclosed herein can be used for cancer therapy and their emission profile can be used to understand the pharamacokinetics of cisplatin (or other anti-cancer Pt moieties), such as their fate inside the cancer cells (such as the amount of dosage that will trigger apoptosis or necrosis). This is divided into three parts:

a). dual probes were developed for optical imaging and functionalized with metal complexes, having specific anti-cancer effects, and cancer targeting peptides (FIGS. 5A-5B, 6A-6B and 7A-7B) and, in parallel;

b). the in vitro anticancer effects via optical imaging and other typical LC-MS and proteomics mass spectroscopy protocols were evaluated. The synthetic protocols, such as cyclen-lanthanide complexes synthesis, peptide conjugation, and imaging are well-established in the inventors' laboratory. Ten cancer/normal cell lines were used to evaluate the pharmacological properties of the compounds. The cancer cell lines included T24, 5637, 22RV1, HeLa, SK-N-SH, A549, A2780, and C666-1 and normal cell lines included MRC-5 and WRPY-1;

c). pharmacokinetics and bio-distribution of the complexes were studied in vivo (with anticancer effects).

Synthesis of "Smart" Maltimodal Theranostic Prodrugs that can Selectively Differentiate Tumor Cells for Effective Drug Release and are Available for In Vitro or In Vivo Imaging and Photodissociation.

There are three major problems associated with commercial anti-cancer drugs/prodrugs: (i) the toxicity of the inactive form; (ii) the recognition of cancer cells; and (iii) the monitoring of their effectiveness. The lanthanide complexes described herein are able to identify cancer cells through conjugation with particular peptides that specifically bind with proteins (sometimes overexpressed) on the surface of the cancer cells; photo-release the drug (e.g., cisplatin) and display two-photon induced NIR emission properties, which enables real-time drug delivery monitoring and whole-body imaging to examine pharmacokinetic effectiveness of the compounds described herein.

General Synthetic Route to Theranostic Compounds

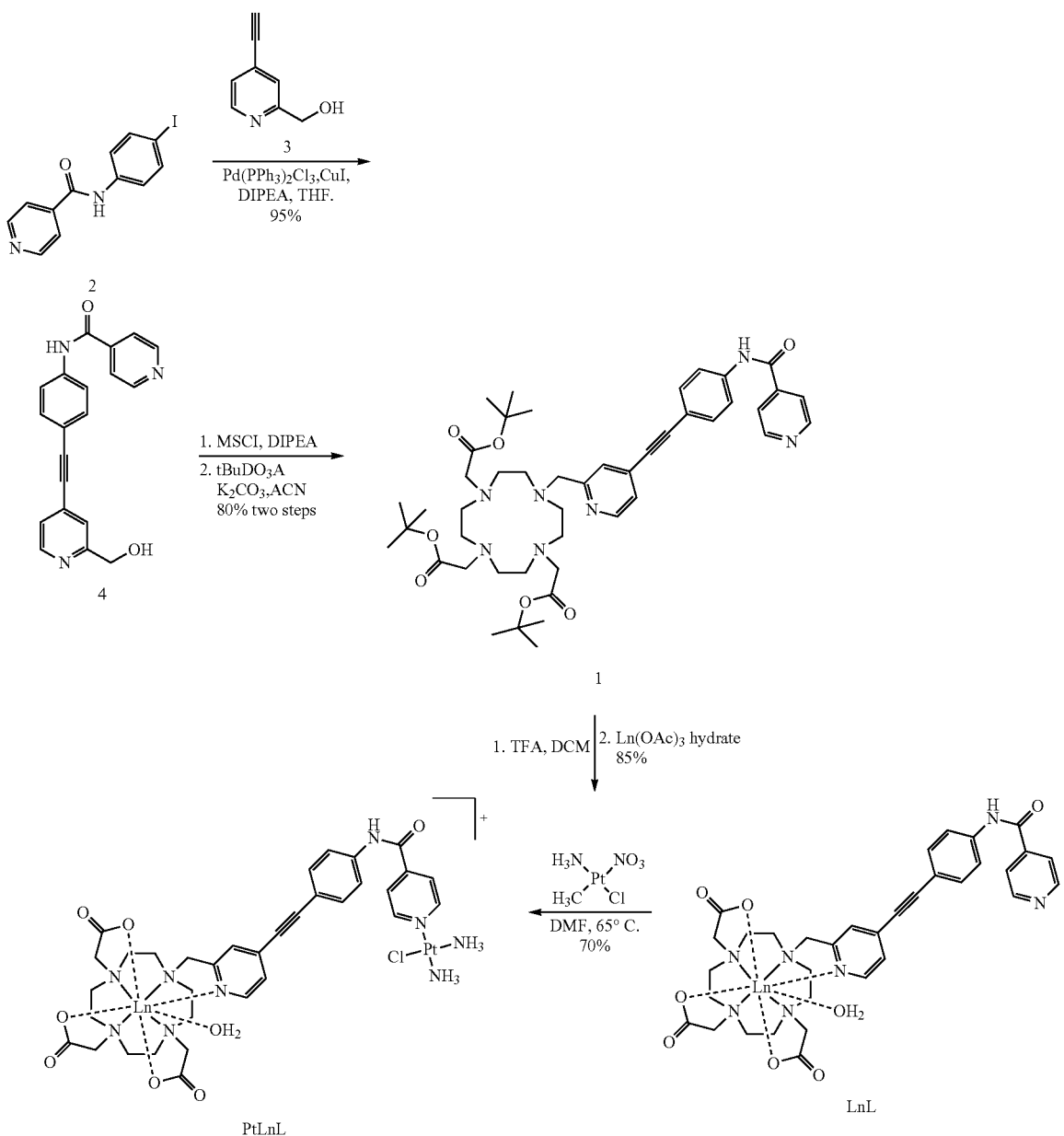

Synthesis of Compound 2.

Isonicyltrinic acid (2.0 g, 16.2 mmol) was added into the solution of DMAP (5.9 g, 48.6 mmol) in dry DCM (200 mL), followed by EDCI (4.6 g, 24.3 mmol), after stirring about 10 min, 4-iodoaniline (3.9 g, 17.8 mmol) was added. The resulting solution was stirred for 12 h at rt under protection of $N_2$ gas. After that the solvent was concentrated to 100 ml, white solids were collected as the product compound 3 (1.2 g, mmol 89/). $^1$H NMR (DMSO-d$_6$, 400 MHz) ☐☐☐10.6 (s, 1H), 8.78 (d, J=2 Hz, 2H), 7.84 (d, J=2 Hz, 2H), 7.72 (d, J=4 Hz, 2H), 7.62 (d, J=4 Hz, 2H); $^{13}$C NMR (DMSO-d$_6$, 100 MHz) ☐ 164.1, 150.3, 141.7, 138.5, 137.4, 122.6, 121.6, 88.1.

Synthesis of Compound 3.

Ethynyltrimethylsilane (2.7 ml, 20.74 mmol) was added into the solution of (4-bromopyridin-2-yl)methanol (3.0 g, 20.74 mmol), Pd(PPh$_3$)$_2$Cl$_2$ (112 mg, 0.16 mmol), Cu (60 mg, 0.32 mmol) and DIPEA (5 mL) in freshly distilled THF (50 mL), the resulting mixture was stirred at 45° C. for 6 h under protection of $N_2$ gas. Silica gel flash column chromatography (Hex/EA 2:1) of the concentrated residue gave a pale yellowed oil. The oil like compound was dissolved in MeOH, K$_2$CO$_3$ was added, and the resulting solution was stirred for 1 h at rt. The solid was filtered out, the filtrate was concentrated. Silica gel flash column chromatography (Hex/EA=1:1) of the residue gave a white solid (2.20 g, 16.56 mmol, 80% of the two steps) as the product. Melting point 69-70° C.; $^1$H NMR (CDCl$_3$, 400 MHz): δ 8.54 (d, J=2 Hz, 1H), 7.37 (s, 1H), 7.28 (d, J=2 Hz, 1H), 4.76 (s, 2H), 3.60 (br, 1H), 3.32 (s, 1H); $^{13}$C NMR (CDCl$_3$, 100 MHz): δ 59.4, 148.3, 131.2, 124.8, 123.0, 822, 80.8, 63.9.

Synthesis of Compound 4.

Compound 3 (0.23 g, 1.72 mmol) was added into the solution of compound 2 (0.84 g, 2.58 mmol), Pd(PPh$_3$)$_2$Cl$_2$ (36 mg, 0.052 mmol), CuI (20 mg, 0.104 mmol and DIPEA (5 mL) in freshly distilled THF (50 mL), the resulting mixture was stirred at 45° C. for 6 h under protection of N$_2$ gas. Silica gel flash column chromatography (DCM/MeOH 30:1) of the concentrated residue gave a pale yellow solid (0.54 g, 1.63 mmol, 95%) as the product. Melting point: 202-203° C.; $^1$H NMR (DMSO-d$_6$, 400 MHz): δ 10.73 (s, 1H), 8.80 (dd, J=4 Hz, 8 Hz, 2H), 8.52 (d, J=2 Hz, 1H), 7.89 (d, J=4 Hz, 2H), 7.86 (d, J=2 Hz, 2H), 7.64 (d, J=6 Hz, 2H), 7.54 (d, J=2 Hz, 1H), 7.37 (dd, J=4 Hz, 8 Hz 1H), 5.53 (t, J=6 Hz, 1H), 4.58 (d, J=4 Hz, 211H); $^{13}$C NMR (DMSO-d$_6$, 100 MHz): δ 164.4, 162.6, 150.3, 149.0, 141.7, 139.8, 132.5, 130.7, 123.2, 121.6, 121.5, 120.3, 116.5, 93.4, 86.8, 64.0. HRMS m/z calcd. for C$_{20}$H$_{16}$N$_3$O$_2$ [M+H]$^+$ 330.1243, found 330.1239.

Synthesis of Compound 1.

To a stirred solution of compound 4 (300 mg, 0.91 mmol) in anhydrous DCM (150 mL) was added DIPEA (1.59 mL, 9.11 mmol) and methanesulfonyl chloride (0.22 mL, 2.73 mmol). The resulting mixture was stirred at rt for 3 hours. The resulting solution was then washed with saturated NaHCO$_3$ solution, saturated NH$_4$Cl solution and saturated NaCl solution. The organic layer was dried with anhydrous Na$_2$SO$_4$, concentrated to give a pale yellowed solid which was directly used in the next step without any more purification. The pale yellowed solid was dissolved in dry MeCN (50 mL). Tri-tert-butyl 2,2',2''-(1,4,7,10-tetraazacyclododecane-1,4,7-triyl)triacetate (tBuDO$_3$A, 0.50 g, 0.61 mmol) and anhydrous K$_2$CO$_3$ (1.26 g, 9.1 mmol) were added. The resulting mixture was stirred at 50° C. for 12 hours under N$_2$ gas. The solids were filtered off and the filtrate was concentrated. Silica gel flesh column chromatography (CH$_2$Cl$_2$: MeOH=20:1) of the residue gave a pale yellow solid (378 mg, 0.46 mmol, 75%) as the product. Melting point: 170-172° C.; $^1$H NMR (CDCl$_3$, 400 MHz): δ 10.64 (s, 1H), 8.75 (d, J=4 Hz, 2H), 8.22 (d, J=4 Hz, 4H), 8.17 (d, J=4 Hz, 2H), 7.48 (d, J=6 Hz, 2H), 7.31 (s, 1H), 7.24 (d, J=4 Hz, 1H), 3.17-2.15 (m, 32H), 1.50 (s, 27H); $^{13}$C NMR (CDCl$_3$, 100 MHz): δ 172.4, 164.5, 158.3, 150.0, 148.5, 141.3, 140.1, 132.7, 132.1, 125.0, 123.8, 122.4, 121.3, 116.6, 95.5, 85.5, 82.0, 58.5, 56.1, 55.2, 54.2, 50.0, 42.5, 27.8, 27.7; HRMS m/z calcd. for C$_{46}$H$_{46}$N$_7$O$_7$ [M+H]$^+$ 826.4867, found 826.4860.

Synthesis of Complexes LnL (Ln=Eu and Gd).

To a solution of compound 1 (100 mg, 0.12 mmol) in DCM (2 mL) was added Trifluoroacetic acid (2 mL). The resulting solution was stirred 24 hours at rt. The solvent was removed under vacuum, the residue was dissolved in 1 mL of methanol. The solution was added into 50 mL of cool ethyl ether. The yellow solid was collected and then dissolved in MeOH/H$_2$O (V:V=1:1), Europium(II) nitrate pentahydrate (54 mg, 0.13 mmol) was added. The resulting solution was maintained in a pH range 6.0-6.5 with NaOH solution (0.4 M) and stirred at rt for 24 hours. The solvents were removed under vacuum, the residue was dissolved in 1 mL of methanol and dropped into ethyl ether (50 mL). The precipitate was filtered and washed with diethyl ether, dried under vacuum at rt. EuL was obtained as a white solid (94 mg, 0.11 mmol, yield=95%). HRMS (+ESI) m/z calcd. for C$_{34}$H$_{37}$EuN$_7$O$_7$ [M+H]$^+$ 808.1967, found 808.1941, for C$_{34}$H$_{36}$EuN$_7$NaO$_7$ [M+Na]$^+$ 830.1786, found 830.1641.

dL can be obtained with a similar procedure showed above. GdL (95 mg, 0.11 mmol, yield=95%). HRMS (+ESI) m/z calcd. for C$_{34}$H$_{37}$GdN$_7$O$_7$[M+H]$^+$ 813.1995, found 813.2005, for C$_{34}$H$_{36}$GdN$_7$NaO$_7$ [M+Na]$^+$ 835.1815, found 835.1915.

Synthesis of PtLnL (Ln=Eu, Gd)

cis-[Pt(NH$_3$)$_2$Cl(DMF)](NO$_3$) was prepared as Peter J. Sadler et al. described previously.[S2] EuL or GdL in anhydrous DMF (1 mL) was added to the cis-[Pt(NH$_3$)$_2$Cl (DMF)](NO$_3$) solution and stirred at 65° C. in the dark for 16 hours. The solvent was removed under vacuum. The residue was dissolved in 3 ml of MeOH, followed with the filtration. The yellowed unreacted cisplatin was filtrated off. The filtrate was added into 50 mL of Et$_2$O, the formed precipitate was collected and re-dissolved in 3 mL of MeOH, the solution was added into 50 mL of Et$_2$O, the precipitate was collected and dried under vacuum at rt. The pale-yellowed solid was afforded as the final product.

The preparation of other theranostic compounds as described herein is well within the skill in the art and can be prepared by the appropriate of the synthetic modification of the synthetic protocols described herein.

Yield and Observed High Resolution Mass Spectra of PtEuL

PtEuL 0.040 g, yield=72%; HRMS (+ESI) m/z calcd. for C$_{34}$H$_{42}$ClEuN$_9$O$_7$Pt [M-NO$_3$]$^+$ 1071.1756, found 1071.1743, for C$_{34}$H$_{43}$ClEuN$_9$O$_8$Pt [M-NO$_3$-Cl+OH]$^+$ 1053.2095, found 1053.1546.

Yield and Observed High Resolution Mass Spectra of PtGdL

PtGdL 0.040 g, yield=70%; HRMS (+ESI) m/z calcd. for C$_{34}$H$_{42}$ClGdN$_9$O$_7$Pt [M-NO$_3$]$^+$ 1076.1784, found 1076.1821, for C$_{34}$H$_{43}$ClGdN$_9$O$_8$Pt [M-NO$_3$—Cl+OH]$^+$ 1058.2123, found 1058.1654.

1.1 Modification of the Prodrug with Low Dark Cytotoxicity and High Stability in the Inactive Form The prodrug PtEuL still has much room for improvement, such as dark cytotoxicity and stability of its inactive form. The compounds disclosed herein overcome these issues as follows.

Figure 6A:
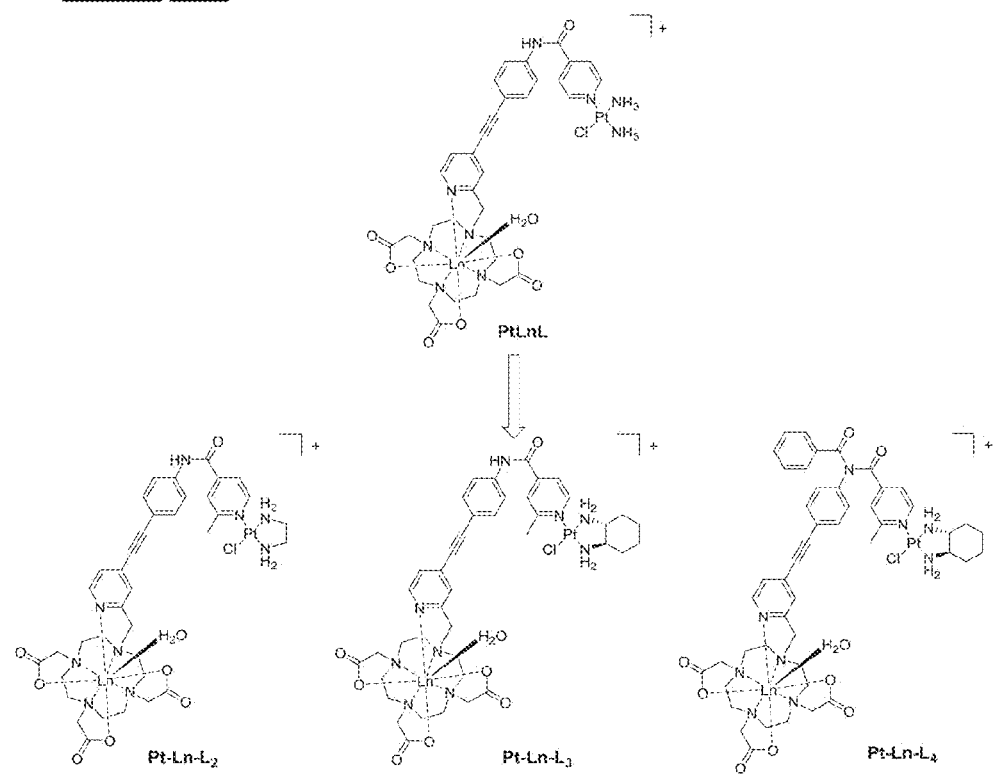
FIG. 6A shows the structures of prodrugs for improvement of the stability and to reduce the toxicity of their inactive forms.
Figure 6B:
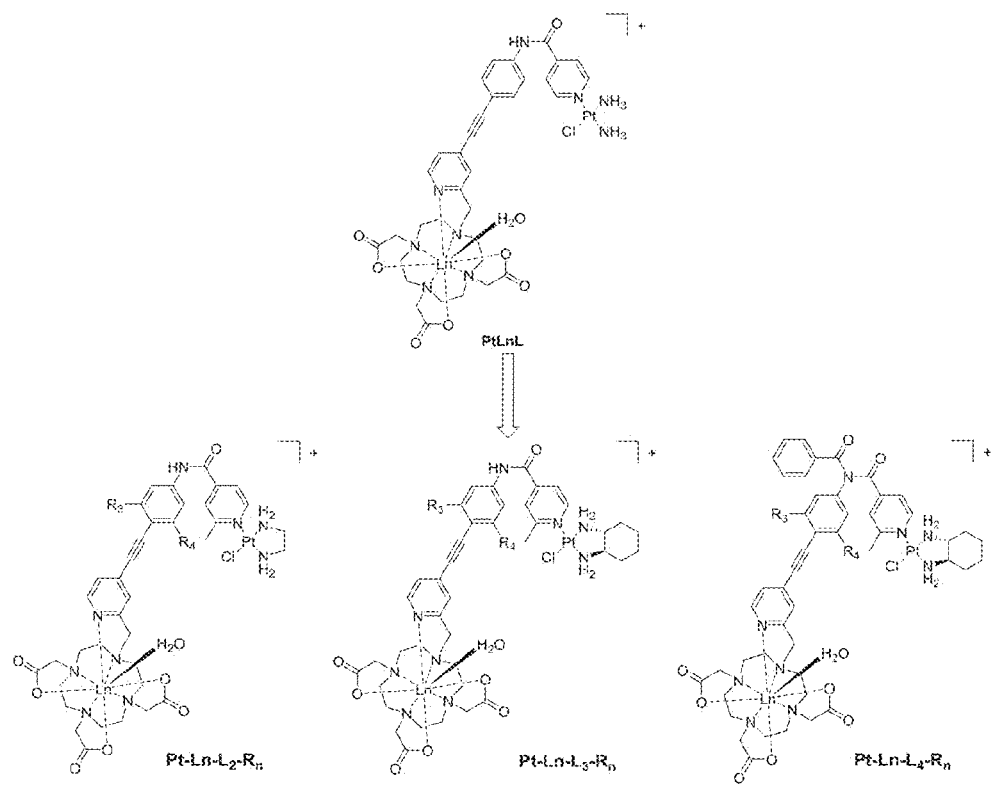
FIG. 6B shows the structures of prodrugs for improvement of their two-photon induced photo release efficiency.

Dark Cytotoxicity of Inactive Prodrug— the alkyl group (e.g., methyl) at the 2-position of the coordinated pyridine ring can protect nucleophilic attack on DNA by NH$_3$ platinum complex ligands, which disassociate. In the meantime, the 1, 2 diamine will chelate to Pt(II) with a much stronger affinity than the two NH$_3$ ligands. The concern here is to suppress direct dissociation of the bound NH$_3$ ligands that may lead to toxicity (FIGS. 6A-6B).

Stability of the Platinum (I) Anticancer Drug in its Inactive Form—

Platinum (II)-based drug are known to react with endogenous cellular thiols. In general, protein thiols are capable of reacting with cisplatin (and other Pt(II)-based drugs), which could trigger toxicity. Intracellular glutathione (GSH) tends to react with Pt complexes and promote leaving of the opposite ligand as a result of the trans-labilization effect. The newly designed complex (FIGS. 6A-6B) are able to suppress thiol attack at the Pt(II) center, which results in reduced toxicity of the compounds disclosed herein. More sterically demanding 1, 2-diamines (e.g. (SS)-trans-cyclohexyl-1,2-diamine may also mitigate unwanted reaction with thiol containing compounds.

Introduce the Third Metal-Gadolinium Ion as "Smart" Multi-Modal Theranostic Prodrug—

Figure 7A:
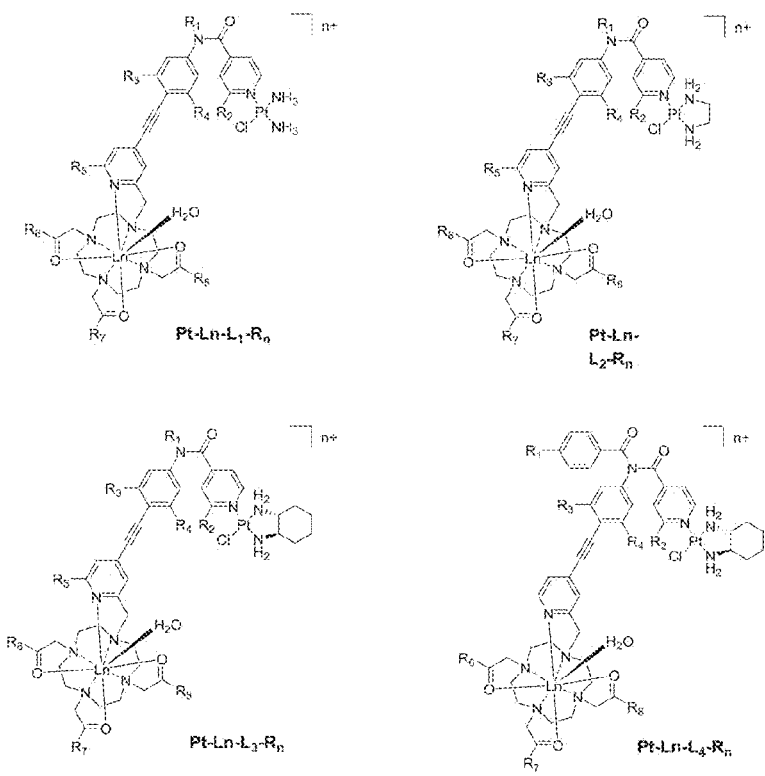
FIG. 7A shows the structures of multi-modal theranostic prodrug. (Plan A: fluorescence imaging.)
Figure 7B:
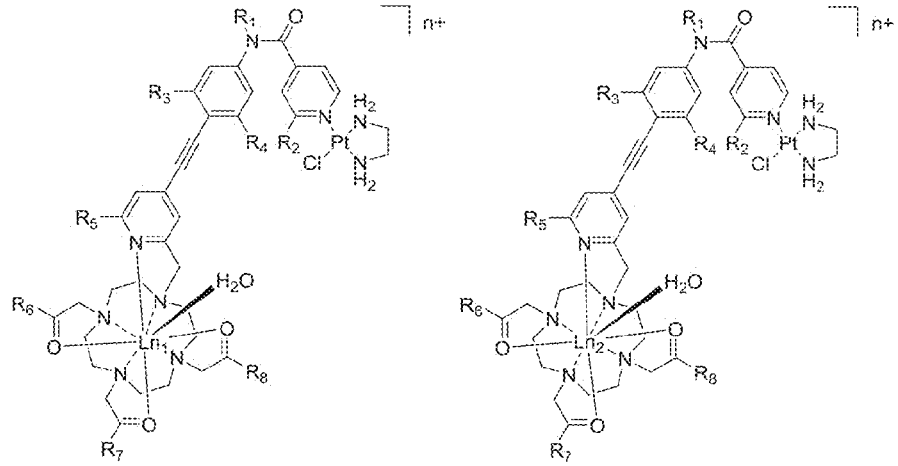
FIG. 7B shows the structures of multi-modal theranostic prodrug. (Plan B: prodrug with optical and MR imaging via hybrid and dimeric Gd—Eu or Gd—Yb complexes)
Figure 7B:
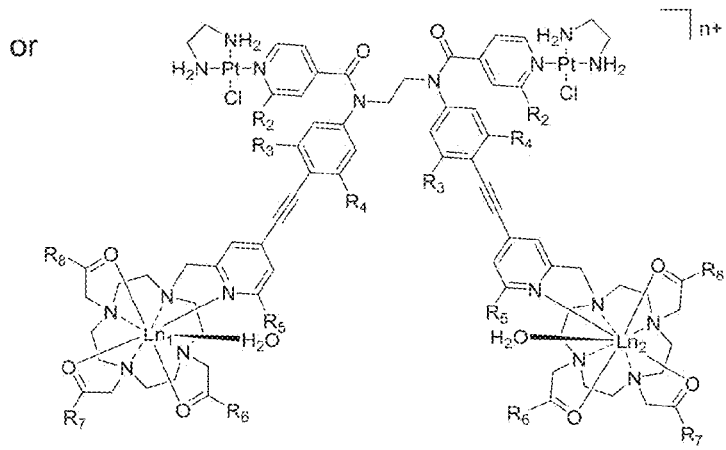

Multi-modal capability is becoming more common in the new generation of imaging agents and with MR imaging, which are capable of providing enhanced spatiotemporal resolution of the site of interest. For incorporation of gadolinium (Gd), there are two main factors to consider, the nature of incorporation and the effective concentration. The gadolinium ion can be introduced as a dinuclear europium-gadolinium (Eu—Gd) complex in the same chelating unit, or as a separate complex only to have the same/similar ligand as the europium complex. In the former case, the europium and gadolinium ions are in the same local environment (bringing two cyclen complexes together via a click reaction), so that the luminescence monitoring would be consistent with MR imaging (FIGS. 6A-6B, 7). In contrast, the latter possibility offers flexibility in metal content such that the ratio between europium and gadolinium does not necessarily have to be 50/50, and depending on factors such as quantum efficiency of the antenna and the relaxivity of the ligand chelate, an optimized metal content ratio could be obtained to maximize the performance of both luminescence and magnetic resonance imaging monitoring (FIGS. 6A-6B, 7A-7B).

1.2 Selectivity of the Complexes Toward Bladder Cancer with Strong Two Photon Induced Emission and Photodissociation Several peptides specific for integrin αvβ3 isoform (as the bladder cancer vector) have been designed and evaluated by molecular docking with "Gold" software. A series of new two-photon available antenna were synthesized. The two-photon absorption cross section can be improved by the change of donor-pi-acceptor system with similar triplet state for the energy transfer for photodissociation (FIGS. 3, 6A-6B, 7A-7B) and conjugated with the same/motif peptide sequence optimizing the structural design for our dual-function probe which aims to achieve better live cell imaging, sensing effect, selectivity and binding affinity to integrin αvβ3 isoform (FIGS. 6A-6B, 7 A-7B).

All the compounds were fully characterized in both solution and solid-state, by a range of spectroscopic techniques (IR, MS, NMR and fluorescence), and X-ray crystallography.

Comprehensive Studies of Proposed Multimodal Theranostic Prodrug

The general photophysical properties, such as emission quantum efficiency and emission lifetime, stability constant (μM value), and quantitative photo-release of the active cancer drug (e.g., platinum of ruthenium complex) were examined. The magnetic properties of these gadolinium complexes were also measured.

2.1 Photophysical, Magnetic Properties and Stability of the Newly Synthesized Prodrug The linear, multi-photon photophysical properties (i.e. emission spectra, emission lifetime, quantum yield and two-photon absorption cross section) and photo-dissociation quantum yield of the lanthanide (III) complexes were measured following literature protocols.

Dark Stability of the Complexes:

Titration experiments were conducted to investigate the stabilities of the synthesized complexes toward several common biological anions and human serum albumin; μM and pKa were also determined. Absorption and fluorescence as well as NMR spectroscopy were used to monitor the stability of the complexes in aqueous solution, following addition of various biological species i.e. serum albumin, citrate.

Photodissociation Level Estimation:

One of the key issues is the photodissociation level of the Pt moiety from the compounds described herein. The triplet states of the chromophores before and after photo-release the drug or upon binding with αvβ3 isoform were measured. Based on the synthetic protocols described herein, La (lanthanum) and Gd (gadolinium) analogs can be synthesized to measure the triplet states of the chromophores as well. The measurements of the triplet states of these chromophores phosphorescence and their phosphorescence lifetime was undertaken at low temperature (77K). The photodissociation kinetics of PtEuL were investigated by monitoring the emission spectrum with different irradiation times of UVA/NIR (light dosage=4 J cm$^{-2}$). The plot of responsive and initial emission intensity at 615 nm ($^5D_0 \rightarrow {}^7F_2$) vs time will be fitted in the exponential growth and decay equation to obtain the pseudo-first order rate constant.

Two-Photon Induced Dissociation and Responsive Emission:

The two-photon absorption (TPA) cross section of the compounds described herein was measured by the Z-scan method (before release of the Pt moiety, the compound is not emissive) and a two-photon excitation wavelength method. An ultrafast laser system using an optical parametric amplifier was used for the measurement. The emitted light was collected with a backscattering configuration into a liquid nitrogen-cooled CCD detector. For the measurement of two-photon absorption cross section, the laser beam is split in two by a beam splitter and one of arm is used as reference for the intensity of the beam, to correct for fluctuations in intensity from pulse to pulse during the course of the measurement. In Z-scan, the position of the sample cell, z, was moved along the laser-beam direction (z-axis) by a computer-controlled translatable table so that the local power density within the sample cell could be changed under the constant incident intensity laser power level.

Relaxation Properties of Proposed Gadolinium "Gd" Complexes:

The efficiency of a gadolinium "Gd" contrast agent to enhance the bulk water relaxation rate is termed its relaxivity—the increment of the water proton relaxation rate per unit concentration. It is measured at a given shield and temperature. The relaxivity of the complexes (mM$^{-1}$s$^{-1}$ at 310K and 3.0/7.0T) were calculated from the relaxation time obtained by a Bruker DPX300 NMR spectrometer in D$_2$O solutions. An inversion-recovery pulse sequence is used and a ten×t$_1$ delay was maintained between successive pulses. The relaxivity (r$_1$) was obtained by a plot of the inverse of longitudinal time (1/t$_1$) versus Gd concentration.

2.2 Binding Affinity Via Emission Titration

As the peptide can bind integrin αvβ3, so the αvβ3 protein on the cell membrane will be made using the lysis buffer. The 10 μM complex was used to be fluorescence quantified. Briefly, 10 of 200 μL Eppendorf tubes was filled 10 μM complex (200 μL), and mixed with a series of αvβ3 protein from 100 nM/L to 1 μM/L (200 μL). All the samples were examined by ABI (7500) to measure the fluorescence emission upon laser excitation (~400 nm). The relationship between the fluorescence intensity to αvβ3 concentrations was calculated. In addition, the binding affinity between the complex and protein was also obtained.

2.3 Evaluation the Binding Affinity Via Isothermal Calorimetry

The binding affinity of the complexes and αvβ3 isoform were studied by isothermal titration calorimetry (ITC), a solution state method that measures the interactions between molecules, e.g. macro-proteins and ligands. The binding affinity (KG), binding stoichiometry (N) and the enthalpy changes (ΔH) of the interaction were determined by ITC experiments directly. From these measurements, the Gibbs energy and entropy change can be determined by established equations. Advantages of ITC include a real-time observation of inter-molecule interactions without limitation on molecular weight in, most importantly, a non-destructive manner.

2.4 Quantitative Analysis of Responsive Europium Emission/Light Dosage for Cisplatin Release Non-emissive lanthanide-platinum complexes in FIGS. 6A, 6B, 7A and 7B, undergo photo-dissociation and hence the antitumor agent, such as cisplatin, can be released upon photo-irradiation. The non-emissive europium center of the inactive Pt—Eu prodrug complex will become highly emissive concurrently. Thus, a time resolved correlation study between europium emission and the level of cisplatin released was investigated, in order to monitor and understand the efficiency of the cisplatin release process. Two concentrations of Pt—Eu prodrug (1 μM and 10 μM) were irradiated at 350/700 nm, and emission of Eu was measured at six given time points (t=5, 10, 20, 30, 45 and 60 min). After injection of a series of concentrations of monohydrolyzed cisplatin (0.1 μM to 50 μM) using HPLC-MS/MS, an external calibration curve was constructed by plotting the concentrations of monohydrolyzed cisplatin against instrument response. A 3D scatter plot of photo-irradiation time (min) vs europium emission ($^5D_0 \rightarrow {}^7F_2$) intensity (a.u.)/integrated area ($^5D_0 \rightarrow {}^7F_J$) vs concentration of cisplatin (μM) was constructed.

Structure and Biological Activity (In Vitro or Vivo Imaging and Specific Anti-Cancer Effects)

The comprehensive in vitro and in vivo evaluation of the compounds disclosed herein in real time studies (e.g. optical imaging and/or MR imaging) and metabolism studies were conducted.

3.1 In Vitro Cytotoxicity Studies and the Rate of Cellular Uptake $IC_{50}$ and MTT assays were conducted in various normal and cancer (i.e. in T24 bladder tumor) cell lines, to examine the cytotoxicity of the lanthanide complexes. All these cytotoxicity assays were performed according to established protocols. The rates of cellular uptakes of complexes can be monitored by flow cytometric/fluorimetric analyses, based on their characteristic emission wavelengths.

3.2 Live Cell Imaging and Analysis of the Effectiveness of the Luminescent Complex In Vitro: A Photocytotoxicity Assay Cancer/normal cells (Cancer cells: T24, 5637, 22RV1, HeLa, SK-N-SH, A549, A2780, C666-1 and normal cells: MRC-5, WRPY-1, ($2 \times 10^4$/well) were incubated in 96-well plates overnight. For in-vitro imaging of the cells that were treated with each of the compounds (Task 1) for 6 hours in the dark. The culture medium was then be replaced by fresh medium and the cells were exposed to light (1-8 J/cm$^2$) produced from a 400 W tungsten lamp fitted with a heat-isolation filter and a 500 nm long-pass filter. For photocytotoxicity −T24 cells were treated with several concentrations of the complex incubated for 12 hours. The free complex in the medium was removed by changing the medium several times. The cells were then irradiated by laser to initiate the release of Pt from the complex and MTT assay will be performed to measure the cell viability after a number of incubation time points. Platinum concentrations were examined by ICP-MS. Therefore, the quantitative relationship between the Pt released and fluorescence intensity (or light source intensity) could be worked out.

3.3 In Vivo Biodistribution Evaluation of Proposed Lanthanide Complexes

ICPMS—

All the compounds were injected intravenously to BALB/c athymic mice bearing xenografted cancer tumors. After 24 hours of incubation, the mice were sacrificed and their main organs, including the excised tumor, removed and fixed in 10% PBS buffered formalin. Control models use athymic mice with only the buffered formalin injected. The tissue samples were frozen and lyophilized for 24 hours before being digested by $HNO_3$ at 70° C. for 4 hours. The lanthanide content, reflective of the quantity of the complexes, can be determined by ICP-MS. The lanthanide content in the urine of the mouse was also evaluated to confirm metabolism of each complex in vivo.

Two-Photon Optical and MR Imaging and Therapy Effectiveness—

The development of xenograft mice using transplanted human bladder tumor cells (T24) which were then allowed to grow to the desired volume. For control experiments, cervical cancer HeLa cells were transplanted into the p-position of the mice. With 14-days of tumor growth, both T24 and HeLa cell xenograft tumors reached a volume of ~100 mm$^3$. The complexes were then injected into the tail vein, the peritoneum/buccally delivered and after 24-48 hours, the xenograft was surgically extracted for two-photon confocal microscopy and MRI experiments, with the peri-tumor cells extract being the control (no lanthanide complex signal should be obtained). The in vivo optical imaging was carried out in the PI institute. The animal imaging box was equipped with 980 and 700 nm lasers. In vivo MRI experiments were carried out on the xenograft tumor on a Bruker Biospec 4.7 T/30 cm scanner (Bruker Inc., MA). In the experiments of tumor inhibition, tumor sizes were measured three times weekly and a growth curve obtained. The data from optical and MR imaging was then compared and evaluated.

Gadolinium and Platinum in Tandem: Real-Time Multi-Modal Monitoring of Drug Delivery by MRI and Fluorescence Imaging A dual-imaging cisplatin-carrying molecular cargo capable of performing simultaneous NIR-optical and MR imaging is reported herein. This long-lasting MRI contrast agent ($r_1$ relaxivity of 24.4 mM$^{-1}$s$^{-1}$) is a photo-activated cisplatin prodrug (PtGdL) which enables real-time monitoring of anti-cancer efficacy. PtGdL is a model for monitoring the drug delivery and anti-cancer efficacy by MRI with much longer remanence time (24 hours) in several organ(s) such as renal cortex and spleen than GdDOTA and its motif control GdL. Upon complete release of cisplatin, substantially all PtGdL is converted to GdL enabling subsequent MRI analyses of therapy efficacy within its reasonably short clearance time of four hours. There is also responsive fluorescence enhancement for monitoring by photon excitation.

Highly cytotoxic platinum (II)/(IV) coordination complexes, such as cisplatin and its derivatives, i.e. carboplatin/oxaliplatin, are well-known potent anticancer agents. Their pharmacologically inactive forms, otherwise termed as pro-drugs, have been developed for optimizing their drug delivery process, e.g. tumor selectivity, water solubility and cell permeability, before subsequent activation at the target sites. Despite the clinical success of several prodrugs, unprecedented challenges remain in achieving optimal pharmacokinetics with minimal adverse side effects since they are non-specifically distributed throughout the body. The major drawback of prodrugs lies in the difficulties of tracing their activities in vitro/in vivo. Intriguingly, theranostic nanomedicine—an emerging paradigm combining diagnostic and therapeutic entities into one—creates a new research landscape and provides a promising solution to the prodrug conundrum.

Theranostic technology affords simultaneous imaging diagnosis and targeted therapy for diseases. For instance, theranostic nanoagents of diagnostic capability and therapeutic efficacy can be utilized in pathological mechanistic studies and guided pre-/post-treatment assessments due to their responsive signaling, e.g. magnetic resonance (MR) and fluorescence in vitro/in vivo. Such agents would allow inventors to obtain biodistribution information, controlled drug release and photodynamic therapy by light. Borrowing the concept from their nano-counterparts, the inventors develop theranostic molecular prodrugs.

The platinum-europium complex (PtEuL) holds great promise as a controlled delivery vehicle of cisplatin. It shows real-time, responsive photo-triggered 'off-on' lanthanide-based long-lived fingerprint emission during the drug delivery to therapeutic process in vitro, once cisplatin is photo-dissociated. However, deep penetration in vivo imaging, such as in internal organs, with the previous methodology is impossible. The present disclosure provides a dual-imaging cisplatin-carrying molecular cargo capable of performing simultaneous NIR-optical and MR imaging, i.e. synergistic sensitive and high temporal-spatial resolution, helps scientists to study the real-time biodistribution and pharmacokinetics in situ more comprehensively and conveniently. In addition, this will assist the evaluation of the performance of the prodrug without interference from autofluorescence, not to mention the advantage of avoiding tedious control experiments.

Figure 9:
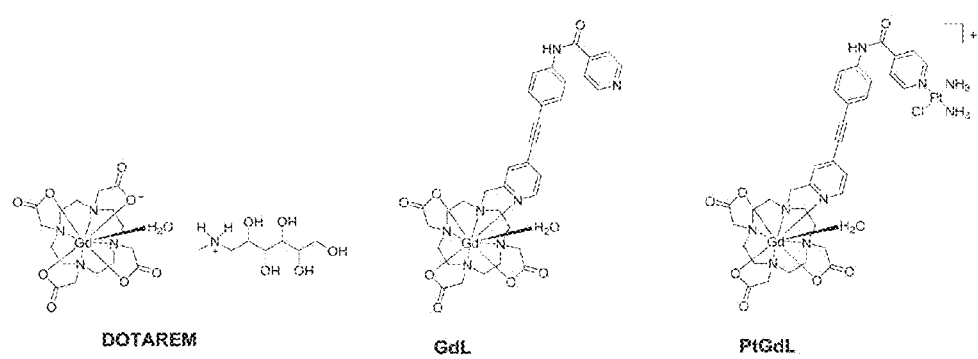
FIG. 9 shows the chemical structures of DOTAREM, GdL & PtGdL.
Figure 10:
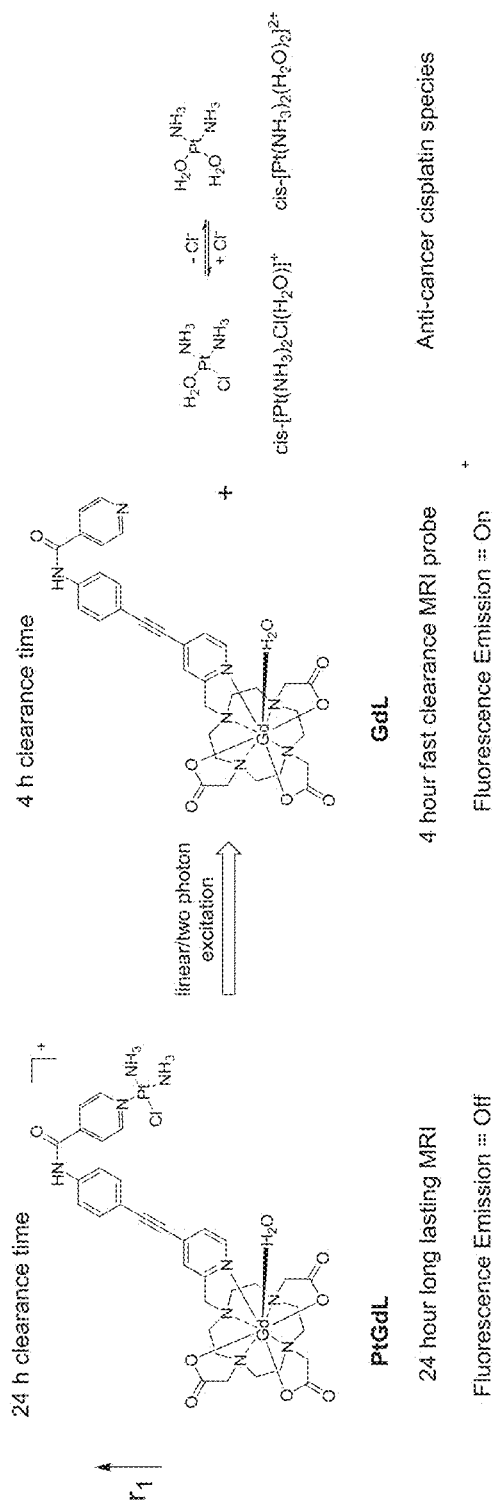
FIG. 10 shows a schematic illustration of the photo-induced cleavage of the multi-modal long-lasting MRI contrast agent (PtGdL) to generate a fast clearance MRI probe (GdL) simultaneously showing highly fluorescent off-on signals and cytotoxic effects.

Herein, is described an 'all-in-one' fluorescence imaging, MRI and photo-dissociable theranostic agents, e.g., PtGdL (FIG. 10) with much larger r1 relaxivity (24.4 mM$^{-1}$s$^{-1}$) and longer remanence (24 hours) MR imaging compared to DOTAREM and GdL (controls) (FIG. 9). The longer remanence time in renal cortex (i.e. between 4-18 hours) provides a sufficient duration for the cisplatin from PtGdL to be released enabling anti-cancer therapy (conditions) via photon clearance motif form, GdL, allowing further therapy analysis and is cleared over a short period of time.

Figure 11A:
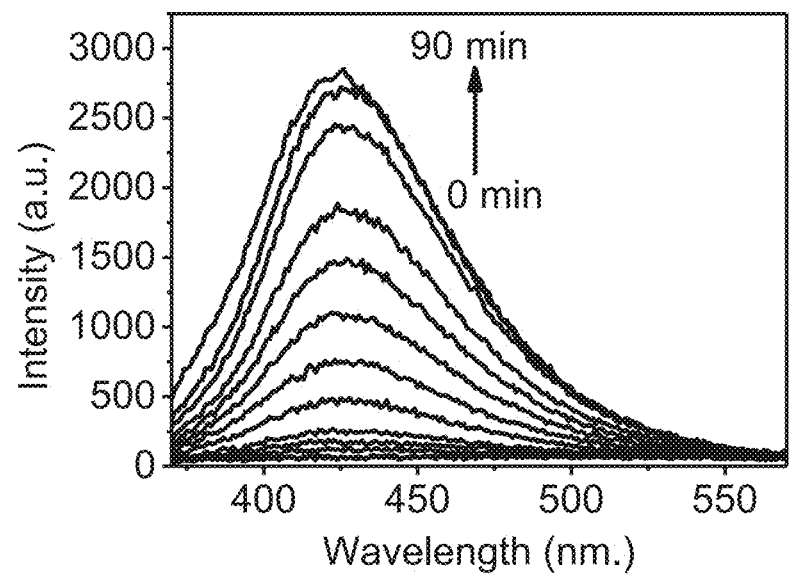
FIG. 11A shows the photoactivation of PtGdL in tris buffer (pH=7.4) solution. Emission spectral ($\lambda_{ex}$=365 nm) variation of PtGdL under UV (365 nm. 5 mW) irradiation
Figure 11B:
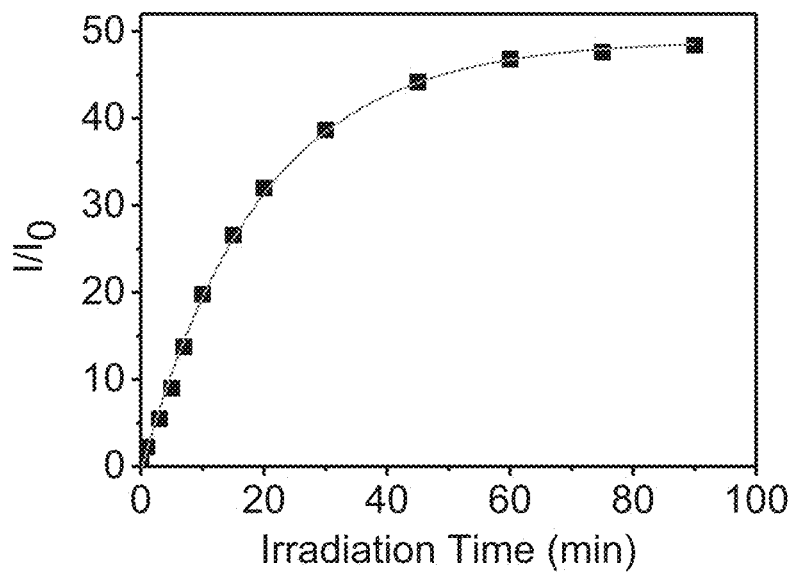
FIG. 11B shows plot of I/I$_0$ @ 426 nm vs. time. Pseudo-first order rate constant k=0.051 min$^{-1}$.
Figure 11C:
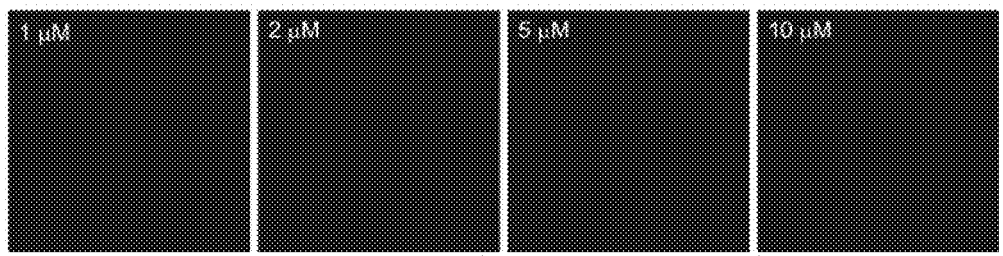
FIG. 11C shows the photoactivation of PtGdL in vitro. Two-photon ($\lambda_{ex}$=730 nm) induced images and cell death of HeLa cells incubated with PtGdL at different dose concentrations (1, 2, 5, 10 μM) for 24 hours. Without irradiation, there is no emission.
Figure 15A:
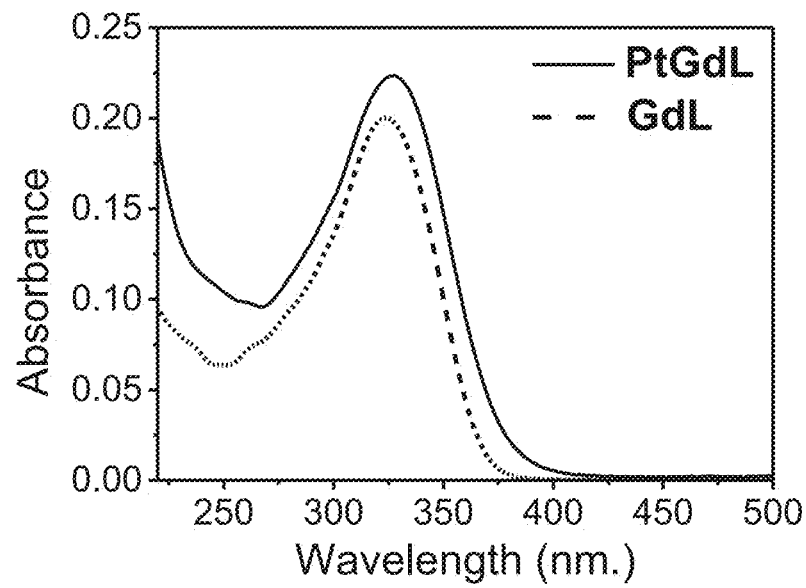
FIG. 15A shows the absorption ($\lambda_{ex}$=365 nm) spectra of PtGdL and GdL in aqueous solution (10 μM).
Figure 15B:
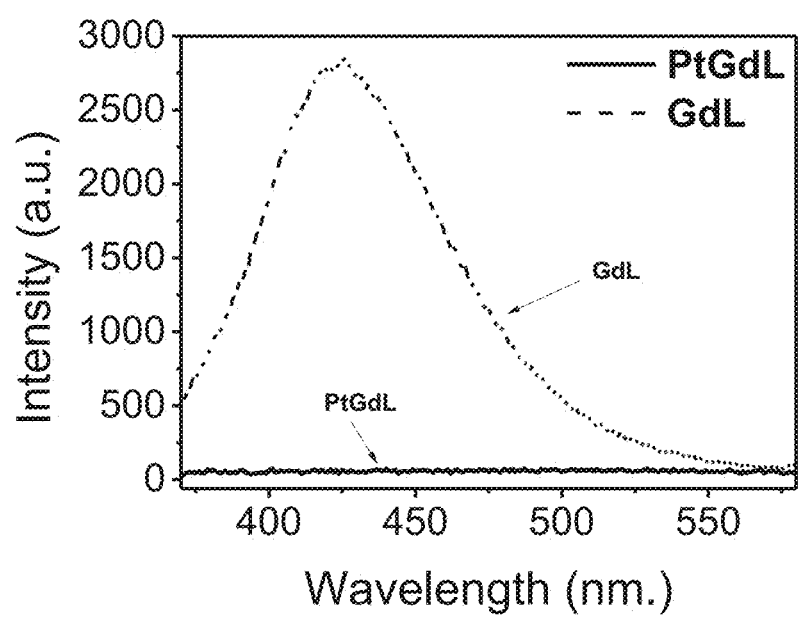
FIG. 15B shows the emission ($\lambda_{ex}$=365 nm) spectra of PtGdL and GdL in aqueous solution (10 μM).

The linear absorption and emission spectra of PtGdL and GdL in aqueous solution (10 µM, $\lambda_{ex}$=365 nm) are shown in FIGS. 15A-15B. PtGdL is non-emissive but can be converted to the emissive form GdL after photon-induced cleavage of Pt. The emission band maxima of GdL is located at 426 nm and attributed to the organic chromophore L. (Photo-activation of PtGdL in tris buffer solution and in vitro are shown in FIGS. 11A-11C. The pseudo-first order rate constant k for the dissociation of the cisplatin unit in PtGdL is 0.051 min$^{-1}$, which is similar to our reported motif complex PtEuL (k=0.053 min$^{-1}$, under same condition with PtGdL). However, the emission intensity of the organic antenna of PtGdL was enhanced 48-fold after the photo-release of the cisplatin unit from PtGdL.

Figure 11D:
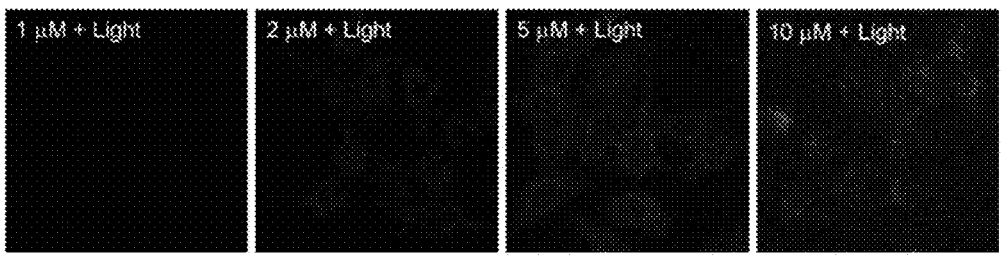
FIG. 11D shows the photoactivation of PtGdL in vitro. Two-photon ($\lambda_{ex}$=730 nm) induced images and cell death of HeLa cells incubated with PtGdL at different dose concentrations (1, 2, 5, 10 μM) for 24 hours. After 30 minutes excitation, bright emission from released GdL was observed.
Figure 11E:
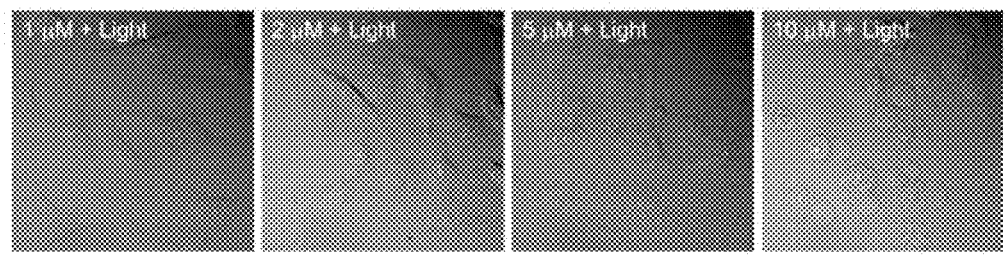
FIG. 11E shows the photoactivation of PtGdL in vitro. Two-photon ($\lambda_{ex}$=730 nm) induced images and cell death of HeLa cells incubated with PtGdL at different dose concentrations (1, 2, 5, 10 μM) for 24 hours. Merged images of FIG. 11D and bright field of FIG. 11C shows significant cell death and bright emission intensity from the cells treated with PtGdL and 730 nm laser.
Figure 16A:
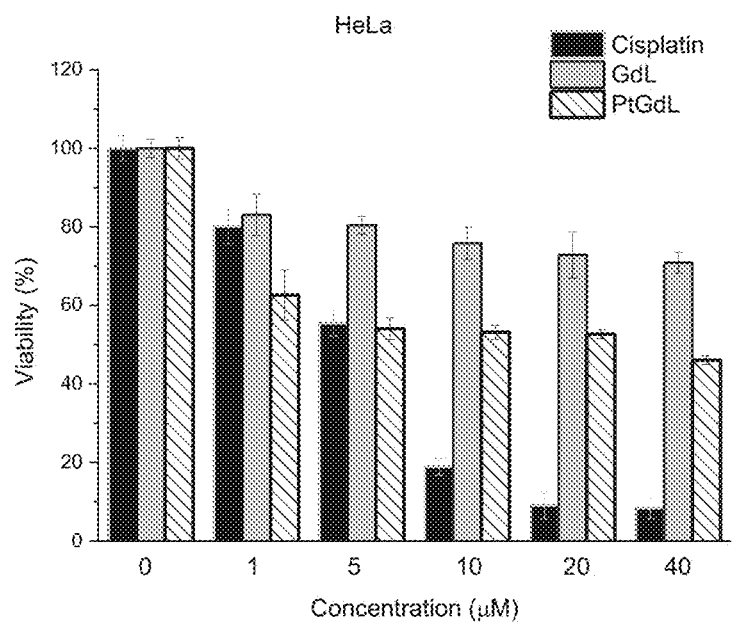
FIG. 16A shows MTT dark cytotoxicity of PtGdL, GdL and Csplatin in HeLa cells. GdL and Cisplatin are used as the controls in this experiment. (IC$_{50}$ of cisplatin in HeLa-5=~3.6±0.2 μM; GdL in HeLa>200 μM; PtGdL in HeLa=~25.0±0.8 μM).
Figure 16B:
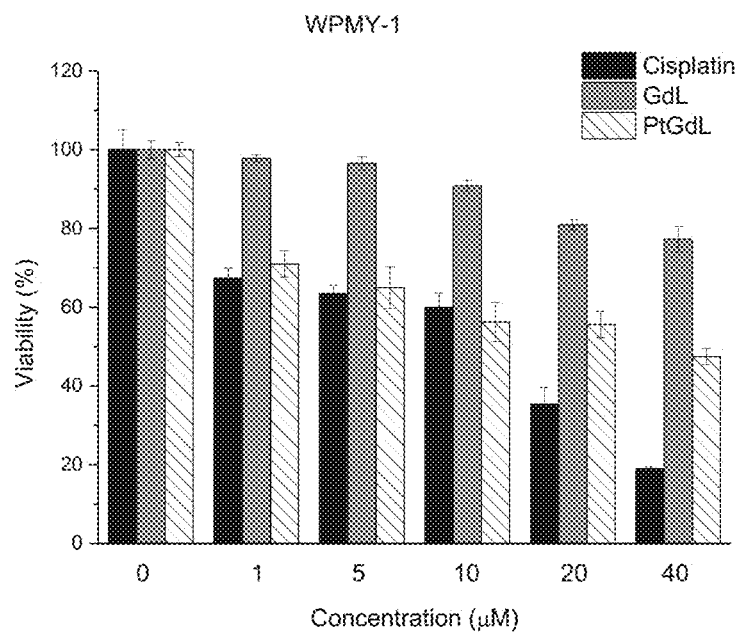
FIG. 16B shows MTT dark cytotoxicity of PtGdL, GdL and Cisplatin in WPMY-1 cells. GdL and cisplatin are used as the controls in this experiment. (IC$_{50}$ of cisplatin in WPMY-1=7.2±0.6 μM; GdL in WPMY-1>200 μM; PtGdL in WPMY-1=43.9±1.1 μM).

The dark toxicity of the PtGdL complex was evaluated in a cancer cell line (HeLa) and a normal cell line (WPMY-1) PtGdL PtGdL showed lower dark toxicity compared to pure cisplatin over 24 hours (IC$_{50}$ of cisplatin in HeLa=~3.3±0.3 µM and WPMY-1=4.2±0.6 µM; PtGdL in HeLa=~23.6±0.8 µM and WPMY-1=43.9±1.1 µM, Row data show in FIGS. 16A-16B). PtGdLres 16A-16B)). PtGdL For photo-cytotoxicity, the two-photon in vitro imaging and photo-release of cisplatin in human cervical cancer cells (HeLa) were investigated on a Leica SP8 (upright configuration) confocal microscope equipped with a femto-second laser. The bright emission from the cells treated with PtGdL was observed in the cytoplasm with significant toxicity at the excitation of 730 nm laser for 30 min (420 mW power within 30 min, 5 min duration, steady temperature=37° C.±1.5° C.). (FIGS. 11D and E) Dramatic cell death can be observed with less than 5 µM dosage concentration with PtGdL, however, the dark IC$_{50}$ of PtGdL against HeLa cells is ~23.6 µM under the same experimental conditions (FIG. 16A). There is no significant emission and/or cell death observed from the cells treated with PtGdL absent exposure to laser irradiation. (FIG. 11C) Control experiments were also performed with GdL under the same experimental conditions and no significant cell death was observed from either GdL treatment or laser irradiation.

Figure 12:
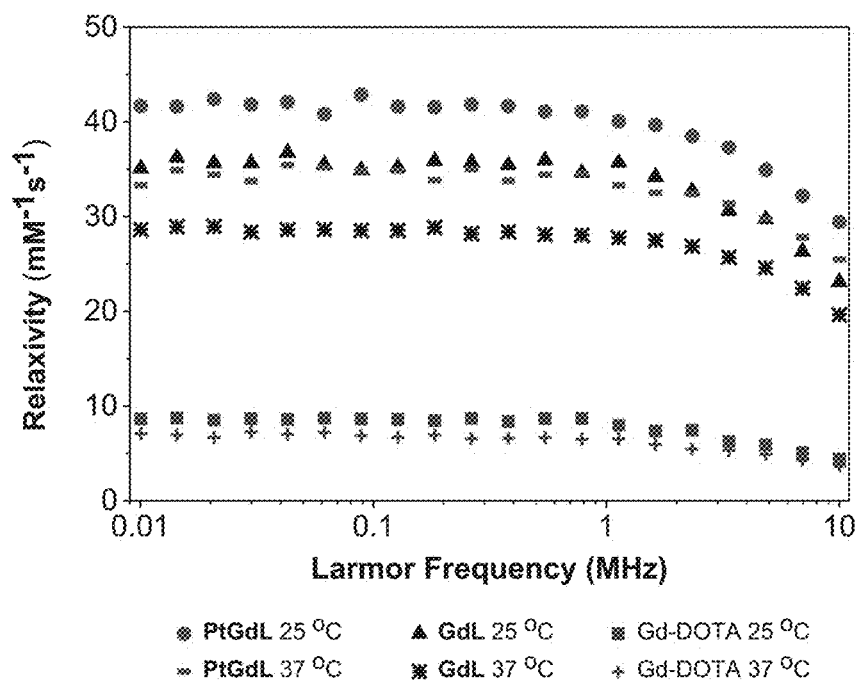
FIG. 12 shows NMRD profiles of PtGdL, GdL and Gd-DOTA (1 mM) at different magnetic field strength values at 25° C. and 37° C.
Figure 17:
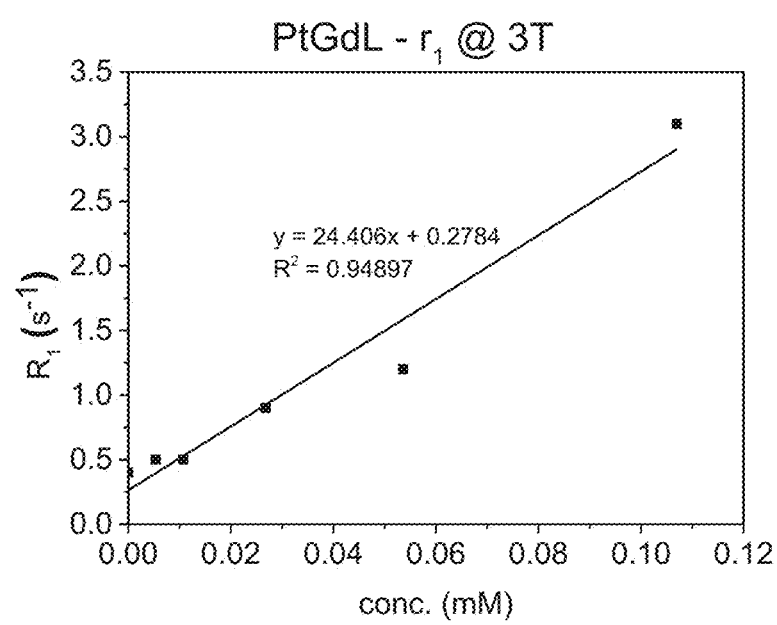
FIG. 17 shows the plot of R$_1$ versus the concentration of PtGdL in aqueous solution. Linear fitting of the data gives a relaxivity of PtGdL=24.4 mM$^{-1}$s$^{-1}$.
Figure 18:
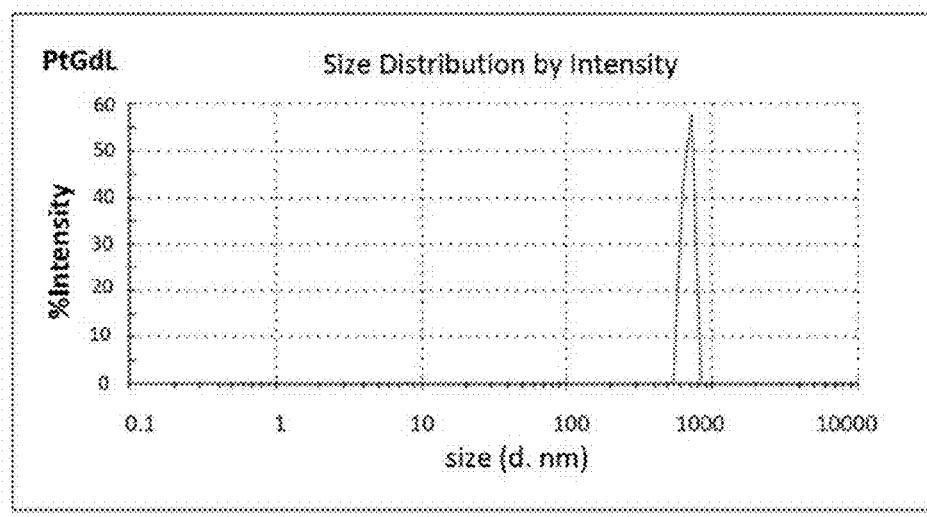
FIG. 18 shows DLS spectrum of PtGdL in aqueous solution (2.5 μM). The DLS spectrum of PtGdL proves that PtGdL could be aggregated in aqueous solution.

The key breakthrough of this work includes the magnetic properties of PtGdL. The r$_1$ relativity of the disclosed MR-available prodrug—PtGdL—has been measured and surprisingly, the relaxivity was six times greater than standard sample Gd-DOTA (FIG. 12). This very promising value encouraged further pursuit of the relaxivity and additional MRI experiments. The efficacy of PtGdL as a potential MRI contrast agent was evaluated by proton nuclear magnetic relaxation dispersion (NMRD). The proton NMRD profiles of the relaxivity—defined as the enhancement of longitudinal relaxation rate by 1 mM of a Gd(III) complex—of PtGdL, GdL and Gd-DOTA are shown in FIG. 12. The profiles were run at 25° C. and 37° C., and the concentration of the samples confirmed by ICP-MS. Moreover, a high preliminary r$_1$ relaxivity of PtGdL of 24.4 mM$^{-1}$s$^{-1}$ was also measured at 3T, demonstrating its potential to be used as a T$_1$-weighted MRI contrast agent. To develop this, the T$_1$ relaxation time of a set of 5 solutions of PtGdL of different concentrations was measured in a 3T Philips Achieva scanner. The concentration of the solutions was confirmed by ICP-MS and the relaxivity determined by the plot of the relaxation rate (R$_1$, s$^{-1}$) as function of the Gd(III) concentration in mM (FIG. 17, Table 2). The observed relaxivity for PtGdL was unexpectedly high. Without wishing to be bound by theory, it is believed that these increased relaxivities are due to an aggregation of the compounds in solution, which results from the isonicotinamide group, leading to a stacking effect of the molecules. This effect becomes even more remarkable in the presence of the cisplatin unit—leading to an additional increase in the relaxivity of PtGdL when compared to GdL: 29.4 vs 23.1 mM$^{-1}$s$^{-1}$ at 10 MHz and 25° C. (FIG. 12) The DLS measurement of a solution of PtGdL showed the presence of aggregates e.g. 672±24 nm (single peak, PDI 0.156; FIG. 18), which suggests that the increasing effect comes from high rotational correlation times due to the presence of aggregates in solution.

The related compounds Gd-DO3A-(4-morpholinopyridine) and the Gd-DTPA-(cisplatin-pyridine-2-ylmethanamine), reported in literature, show a relaxivity of 53 mM$^{-1}$s$^{-1}$ (20 MHz and 25° C.) and 6.5 mM$^{-1}$s$^{-1}$ (20 MHz, 37° C.) respectively. The coordination sphere of the Gd(III) centre in the present disclosed compounds and in the literature analogues is the same i.e. featuring one water molecule (Table 1). The presence of the cisplatin unit directly conjugated to the pyridine only leads to a small increase of the relaxivity when compared to Gd-DOTA. These facts help support the inventors' conclusion that the increased relaxivities of the invented compounds result from the additional isonicotinamide group.

TABLE 1

Photophysical properties and relaxivity of PtGdL and GdL.

| Complex | $\lambda_{max}$/nm [a] | ε/ $M^{-1} cm^{-1}$ [a] | q ± 0.2 [b] | φ/% [d] | $r_1$/ $mM^{-1}s^{-1}$ [e] |
|---|---|---|---|---|---|
| PtGdL | 327 | 22300 | 1.0 [c] | <0.1 | 29.4 |
| GdL | 324 | 20000 | 1.0 | 3 | 23.1 |

[a] Absorption coefficient in H$_2$O, 298K;
[b] Coordination number of water molecules, the q value of GdL was determined by comparison of the emission lifetime of europium(III) analogue of GdL, EuL in D$_2$O and H$_2$O, which is reported in our previous work. (*Chem. Commun.* 2015, 51, 14022-14025; *J. Chem. Soc., Perkin Trans.* 1999, 2, 493-504.)
[c] For PtGdL the q value could not be determined by using the same method with GdL because PtEuL is non-emissive, however PtGdL should have the same hydration number (q = 1.0 ± 0.2) as GdL due to the similarity of structure.
[d] Fluorescence quantum yield of the ligand emission of the complexes was determined by integrated sphere methods. (*Chem. Rev.* 2010, 110, 2729-2755)
[e] T$_1$ relativity of the Gd complexes at 10 MHz, 25° C.

TABLE 2

Raw data of the T$_1$ relativity of PtGdL in FIG. 17.

| Conc.[a] (mol/L) | T$_1$ (ms)[b] slice 1 | T$_1$ (ms)[b] slice 2 | T$_1$ (ms)[b] average | R$_1$ (s$^{-1}$) [c] |
|---|---|---|---|---|
| 1.07E−04 | 373 | 276 | 324.5 | 3.1 |
| 5.36E−05 | 917 | 812 | 864.5 | 1.2 |
| 2.68E−05 | 1231 | 1110 | 1170.5 | 0.9 |
| 1.07E−05 | 1960 | 1699 | 1829.5 | 0.5 |
| 5.36E−06 | 2092 | 1933 | 2012.5 | 0.5 |
| PBS | 2300 | 2200 | 2250 | 0.4 |

[a] The concentration of Gd(III) were corrected with ICP-MS.
[b] The longitudinal relaxation time were measured twice of each sample and taken average.
[c] The longitudinal relaxivity, R$_1$ = 1/T$_1$.

Figure 13A:
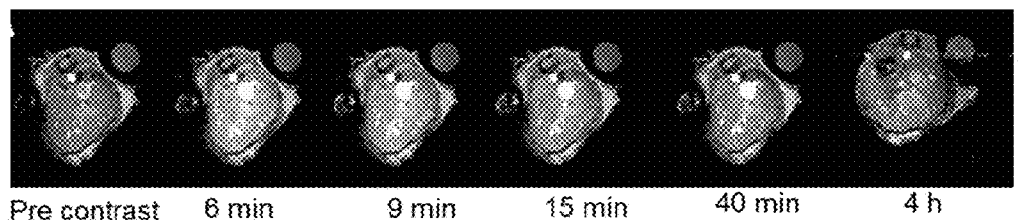
FIG. 13A shows in vivo T$_1$-weighted MR images of mouse liver obtained between 6 minutes and 4 hours post injection for GdL.

In vivo 7T MRI measurements of the disclosed compounds in normal mice were conducted. The images were acquired at various time points after solutions of commercial GdDOTA complex (DOTAREM), GdL and PtGdL were injected. After injection in the caudal vein of the wild type mice tail, an immediate signal enhancement was observed in the liver and rental cortex, indicating the presence of the contrast agent inside the tissue of interest. GdL was immediately captured by the liver, spleen and the kidneys (FIGS. 13A and 14A). No specific remanence was observed in the tissues of interest. Full clearance was observed at a temporal window of about 4 hours post-injection (FIGS. 13C and 14C). In comparison to GdDOTA, GdL presents a similar pattern of biodistribution in the kidneys but a slower clearance rate in the liver (0.002 vs 0.016 enh/min). However, PtGdL presents a delayed capture, longer remanence and clearance compared to GdL. GdL is immediately captured by the liver, spleen and the kidneys compared to PtGdL which displays a delay in capture of 6-9 minutes depending on the tissue of interest (FIGS. 13B and 14B).

Figure 13B:
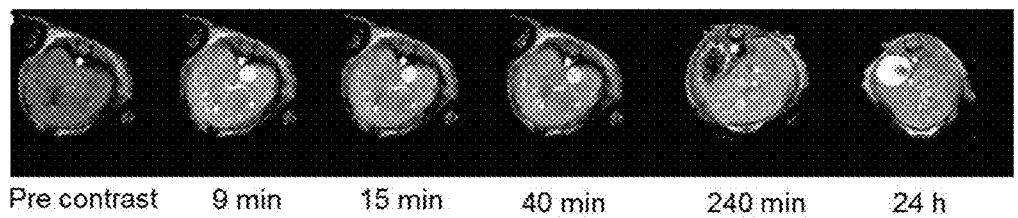
FIG. 13B shows in vivo T$_1$-weighted MR images of mouse liver obtained between 6 minutes and 24 hours post injection for PtGdL.
Figure 13C:
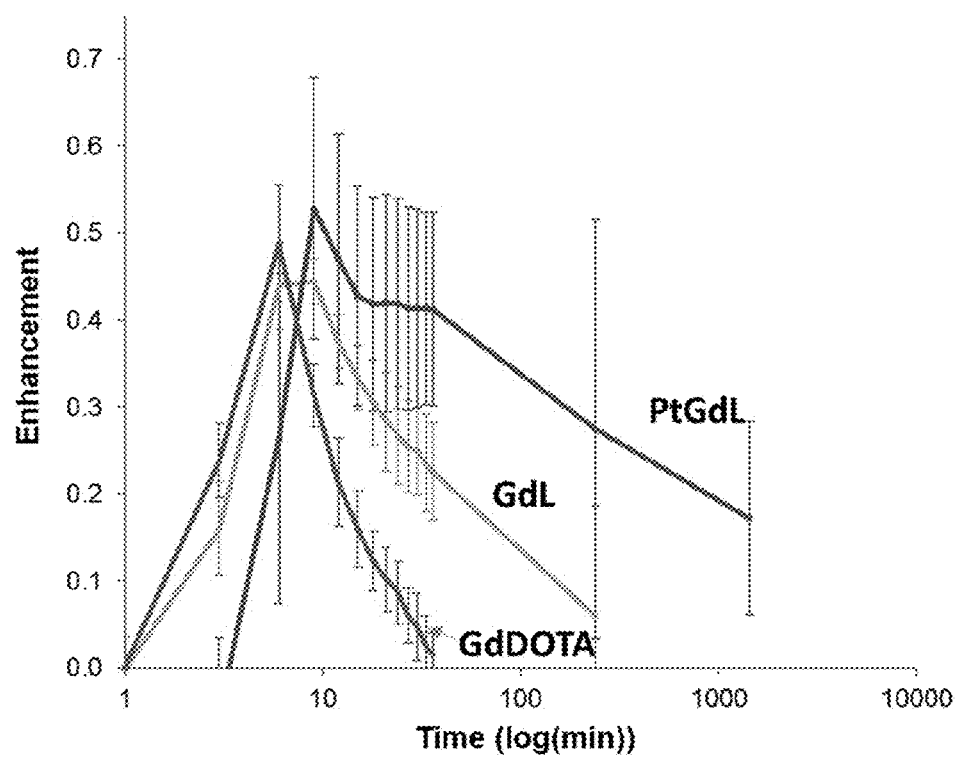
FIG. 13C shows the signal-decay curves (PtGdL, GdL and DOTAREM).
Figure 14A:
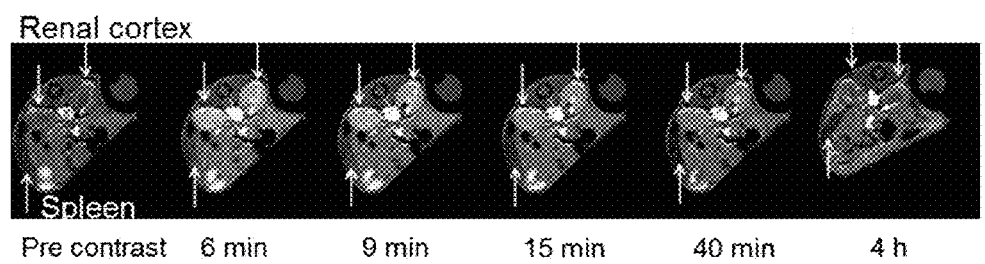
FIG. 14A shows in vivo T$_1$-weighted MR images of mouse renal cortex between 6 minutes and 4 hours for GdL.
Figure 14B:
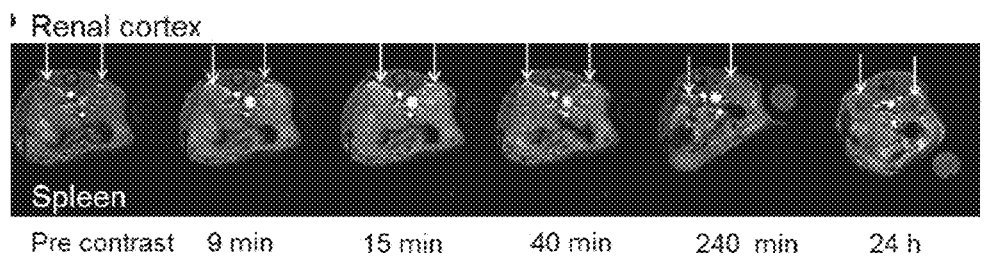
FIG. 14B shows in vivo T$_1$-weighted MR images of mouse renal cortex between 6 minutes and 24 hours for PtGdL.
Figure 14C:
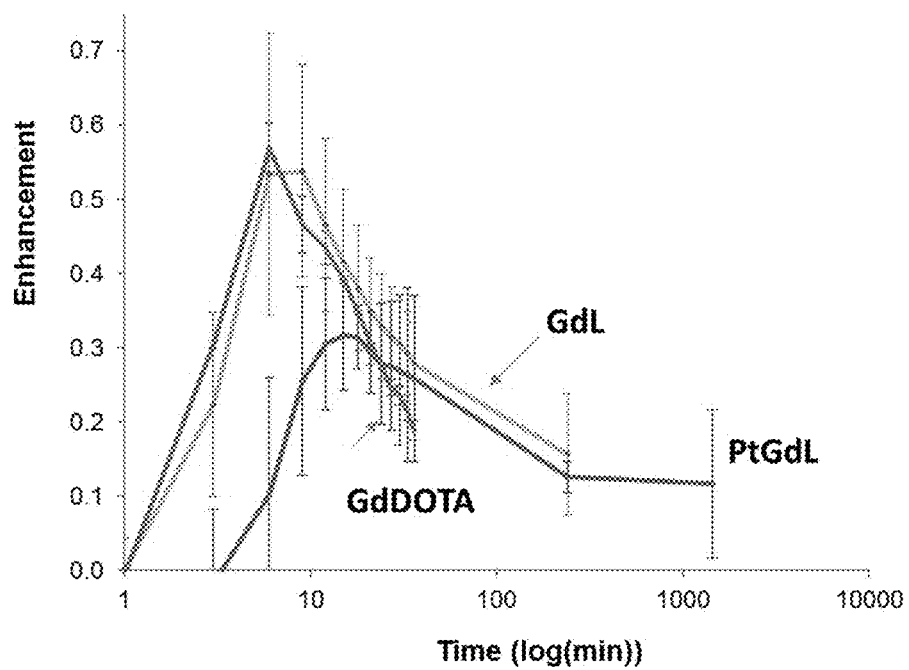
FIG. 14C shows signal-decay curves (PtGdL, GdL and DOTAREM).

No specific remanence (up to 4 hours) was observed in the tissues of interest for GdL (FIG. 13A) whereas a hepatic and renal remanence of about 24 hours was observed for PtGdL (FIG. 13B). This long-lasting clearance may be due to interaction of the cisplatin moiety in PtGdL with certain proteins in the tissues of interest. In terms of clearance of the MR agent, the signal enhancement of GdL decreased by 90% at 4 hours after injection, indicating full clearance (FIG. 13C). The enhancement of PtGdL, however, did not change greatly after 24 hours, indicating that full clearance is in the order of about a day (FIG. 14C). Thus PtGdL, with the above advantages over cisplatin-free GdL, has the potential to be a new generation MRI-available prodrug.

Controlled photo-triggered release of cisplatin from PtGdL serves as an anti-cancer drug delivery vehicle while the efficacy of the anti-cancer effects can be monitored at the same time from the untransformed PtGdL. Upon substantially complete cleavage of the platinum containing complex, e.g., substantially complete generation of GdL from PtGdL, the remaining GdL is cleared in the next 4 hours, and the fate of cisplatin is well-studied in literature.

The inventors have advanced photo-activated theranostic anti-cancer prodrug by incorporating excellent MRI capabilities ($r_1$=24.4 mM$^{-1}$s$^{-1}$) as a tool for monitoring real-time anti-cancer efficacy. The inventors are able to control the release of drug in vitro by manipulating the power and exposure time of triggering light via the present invented agent, PtGdL, which also exhibits longer remanence time (24 hours) in target organ(s) than the cisplatin-free GdL and GdDOTA controls, thus allowing a wider timeframe for the released cisplatin to perform anti-cancer function and monitoring. Upon substantially complete release of cisplatin, all PtGdL is converted to GdL for subsequent and responsive MR and fluorescence imaging analysis of therapy efficacy and biodistribution within its reasonably short clearance time of 4 hours.

Materials and Methods

Photophysical Measurements

UV-Visible absorption spectra in the spectral range 200 to 1100 nm were recorded by an HP Agilent UV-8453 spectrophotometer. Emission spectra were recorded by using a Horiba Fluorolog-3 spectrophotometer. (Available for fluorescence lifetime and steady state emission measurement—equipped with a visible to near-infrared-sensitive photomultiplier in nitrogen flow cooled housing). The spectra were corrected for detector response and stray background light phosphorescence. The absolute emission quantum yields of the metal complexes were measured by integrated sphere.

The linear light induced dissociation of PtGdL in tris buffer (20 mM Tris base, 50 mM NaCl, pH 7.4) was monitored by determination of the emission intensity of solution of PtGdL in tris buffer with different light dosage of 365 nm UV light. In general, 3 mL of the solution of PtGdL (3 µM in tris buffer) in a 3.5 mL quartz cuvette was irradiated with a 365 nm UV lamp (5 mW) with stirring. The emission spectra of the solution were recorded at different time points (0, 1, 3, 5, 7, 10, 15, 20, 30, 45, 60, 75 and 90 min).

Relaxtvity Measurements

The 1/T$_1$ nuclear magnetic relaxation dispersion (NMRD) profiles of GdDOTA, GdL and PtGdL (1 mM) were recorded on a Stelar SMARtracer FFC fast-field-cycling relaxometer covering magnetic fields from 2.35×10$^{-4}$ T to 0.25 T, which corresponds to a proton Larmor frequency range of 0.01-10 MHz. The temperature was controlled by a VTC91 temperature control unit and maintained by a gas flow. The temperature was determined according to previous calibration with a Pt resistance temperature probe. The accurate concentration of the solutions was determined by Inductively Coupled Plasma Mass Spectrometer (ICP-MS).

A set of 5 solutions with concentrations 5.4 µM to 0.1 mM were prepared and their Gd(II) concentration confirmed by ICP-MS, measured in a PerkinElmer NexION 350D spectrometer. The T$_1$ values of these solutions were measured in a 3T Philips Achieva scanner, using a MOLLY sequence.

Dynamic Light Scattering (DLS) to investigate the presence of aggregates in a PtGdL solution was performed in Mavernm Zetasizer Nano-S equipment, at 25.0° C.

In Vitro Experiments
Cell Culture

Human cervical cancer HeLa cells were grown in Dulbecco's Modified Eagle Medium (DMEM). Human lung diploid fibroblasts—MRC-5 and prostate stromal—WPMY-1 cells were obtained from the cell resource center of Shanghai Institute of Biological Sciences, Chinese Academy of Sciences. MRC-5 and WPMY-1 are growth in MEM (GIBCO 41500034) and supplemented with 10% (v/v) fetal bovine serum, 1% penicillin and streptomycin at 37° C. and 5% $CO_2$.

MTT Cell Cytotoxicity Assays

MRC-5 or WPMY-1 cells were treated with testing complexes for 24 hours at 6 concentrations (0, 1, 5, 10, 20 and 40 µM). The cell monolayers were rinsed with phosphate buffer saline (PBS) once and incubated with 0.5 mg/mL MTT (3-(4, 5-dimethylthiazol-2-yl)-2 and 5-diphenyltetrazolium bromide) solution. The cellular inhibitory potency of the complexes was examined by the formation of formazan after addition of MTT for 3 hours to allow formazan production during cell metabolism. After that, formazan was fully dissolved in DMSO through oscillation. Finally, the absorbance of solution was measured with Biotek Power wave xsMicroplate Reader at the wavelength of 570 nm and 690 nm.

Two-Photon Induced Activation and Florescence In Vitro Imaging

The cells were incubated with PtGdL (1, 2, 5, 10 µM) for 12 hours. The complexes (cell impermeable and dissolved in the medium) were washed out with PBS buffer. The cells with complexes were placed in the tissue culture chamber (5% $CO_2$, 37° C.) inside the two-photon confocal microscope. In vitro images were captured by using the Leica SP8 (upright configuration) confocal microscope which equipped with femto-second laser (wavelength: 700 to 1000 nm) and 40×/60× oil immersion objective. The in vitro images were taken after 30 min laser excitation ($\lambda_{ex}$=700 nm, Power=420 mW, each 5 min with 1 min laser excitation, steady temperature=37° C.±1.5° C.).

$T_1$ Weighted In Vivo Imaging and Bio-Distribution

Biodistribution studies were conducted on a 7T micro MRI system (Bruker, Wissembourg, France) equipped with a $^1H$ radiofrequency linear coil birdcage probe of 4 cm inner diameter in order to assess the uptake and clearance of MRI contrast agents (CA) from kidney, muscle, spleen, liver. All animal experiments were performed in accordance with the institutional animal protocol guidelines in place at Paris Descartes University, (saisine CEEA34.JS.142.1) and approved by the Institute's Animal Research Committee.

Wild-type female 8 weeks BALB/c mice (Elevage Janvier, Le Genest-St-Isle, France) were anaesthetized with isoflurane (1.5%, with air/$O_2$ 0.5/0.25 L·min$^{-1}$) inhalation and placed in a dedicated contention cradle. 300 µL of Gadolinium complexes in 0.9% physiological serum were intravenously injected via the tail vein while the mouse was in the scanner. For reproducibility studies, 3 mice per group were injected (n=3).

The scanning protocol was developed using Bruker Paravision 5.1 software. DCE Dynamic contrast Enhanced sequence was recorded using Intragate Flash multislices for motion free artifacts T1 weighted sequence (TR=100 ms, TE=4 ms, alpha=80°). The final images have a spatial resolution of 236 m×236 m in plane. The total scan time was in the order of 3 min 14 s per images. The dynamic follow-up is measured during in a scan time of 40 minutes.

To study the biodistribution of each complex, several regions of interest (ROI) were monitored: the liver, muscle, spleen, kidney, and vessels. The corresponding MRI intensity related to the amount of the Gd complex contrast agents was plotted versus time to visualize the uptake and clearance of each complex into the organs. Comparison with commercial GdDOTA (DOTAREM, Guerbet, France) was also performed at the corresponding concentration of Gd (10 mM).

Biodistribution Imaging of Gd-Based Complexes: GdL & PtGdL

Figure 8:
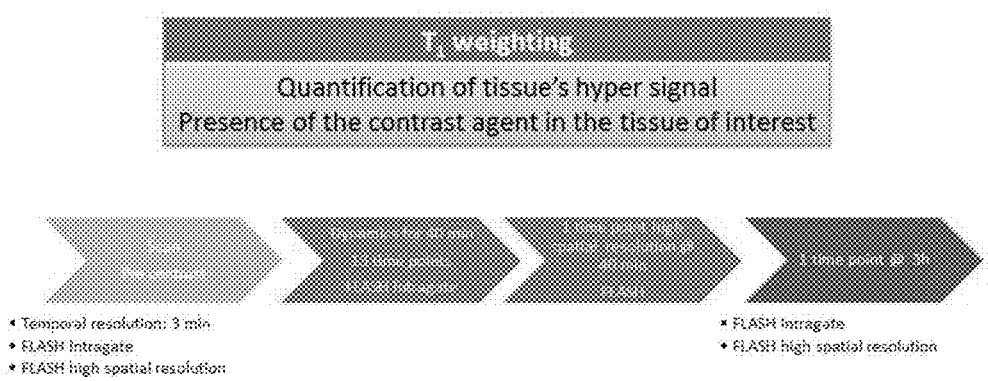
FIG. 8 shows MRI Protocols, 7T, ENSCP.

FIG. 8 presented MRI protocols process from pre-scan to 1-time point at 3 hours. In the following Table 3, the in vivo MRI protocol at 7 T is presented:

TABLE 3

In vivo MRI protocol @ 7T

| Sequence types | Sequence details | | Acquisition times |
|---|---|---|---|
| High spatial resolution $T_{1w}$ | FLASH, multi slice Respiratory gating TR = 500 msec, TE = 3.5 msec α = 80° 18 slice, 1 mm | NA = 4 NR = 1 FOV = 3 × 3 cm Matrix = 256 × 256 Pixel resolution = 117 µm/pixel | 4-6 min |
| Pre contrast $T_{1w}$ | IG FLASH, multi slice Respiratory navigator TR = 100 msec, TE = 4 msec α = 80° 5 slices, 1 mm | NR = 15 Time Frame = 1 FOV = 3 × 3 cm Matrix = 128 × 128 Pixel resolution = 236 µm/pixel | 3 min |
| Dynamic $T_{1w}$ | IG FLASH, multi slice Respiratory navigator TR = 100 msec, TE = 4 msec α = 80° 5 slices, 1 mm | MR = 190 Time Frame = 13FOV = 3 × 3 cm Matrix = 128 × 128 Pixel resolution = 236 µm/pixel | 40 min |

It is observed that in one embodiment of the present disclosure the Pt-GdL presents a delayed captured, longer remanence and clearance compared to the GdL and GdDOTA.

Extended Studies-Ruthenium (Ru) (II) Based Prodrugs

Figure 19A:
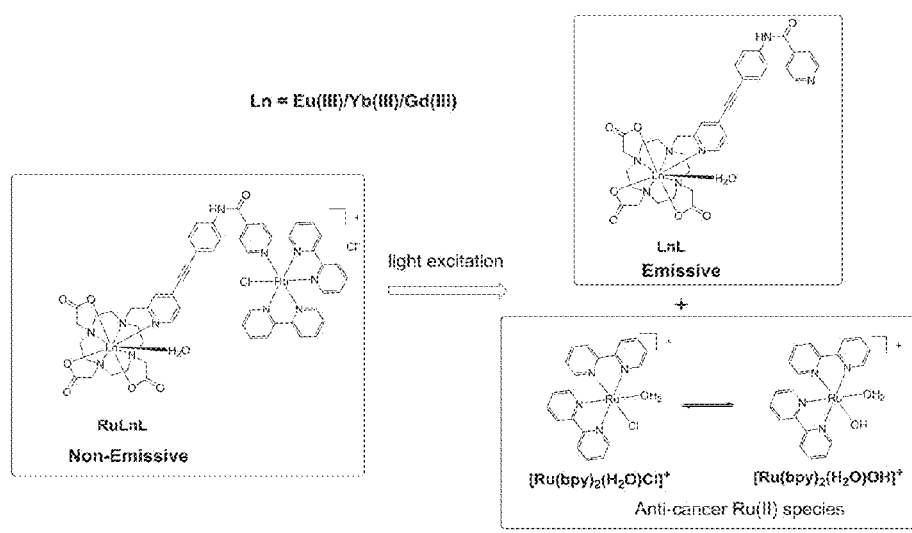
FIG. 19A shows the schematic illustration of the photo-induced cleavage of our photo-responsive anticancer agent RaLaL (Ln=Eu, Gd, Yb or other lanthanide element) to generate highly luminescent off-on signals and cytotoxic effect.
Figure 19B:
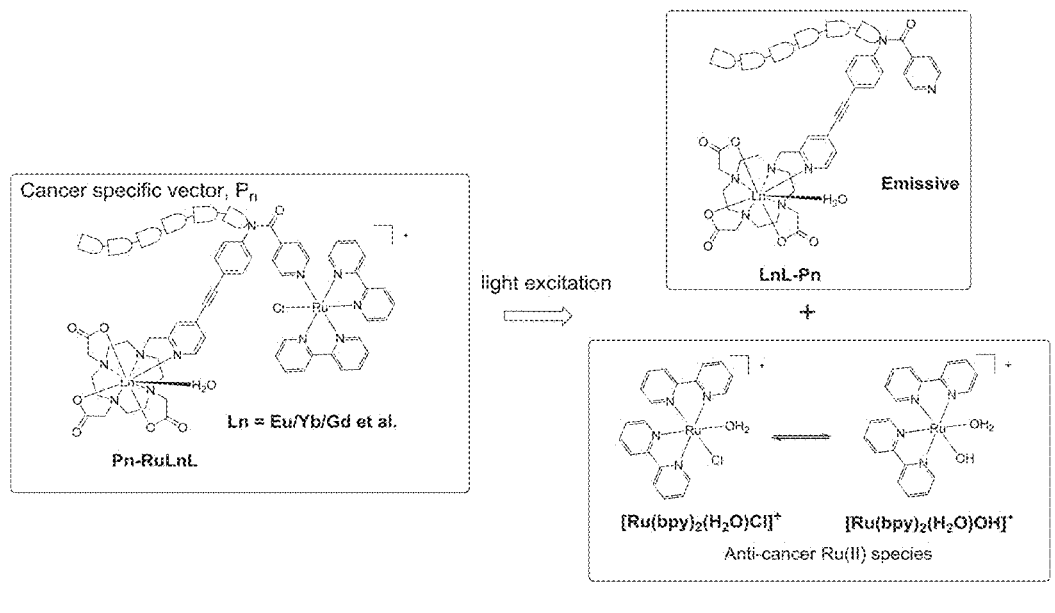
FIG. 19B shows the designed cancer targeted specific ruthenium lanthanide prodrugs.

The findings of the platinum complexes were extend to ruthenium (II) based prodrugs as well. Since ruthenium (II) complexes have similar DNA binding ability as compared with platinum (Pt) (II) complexes. FIGS. 19A-19B shows the general design of ruthenium-lanthanide (europium/ytterbium/gadolinium) prodrugs as a photo-controlled delivery vehicle of a toxic ruthenium (II) compound, [Ru(bpy)$_2$Cl]$^+$. FIG. 19 A shows similar design of PtEuL. FIG. 19B is the design of bladder cancer specific ruthenium europium/ytterbium/gadolinium complexes as photo-triggered luminescent responsive or luminescent/MRI dual model prodrugs capable of performing optical or optical and MRI dual model monitoring delivery of the toxic complex-[Ru(bpy)$_2$Cl]$^+$. Five proof of concept studies have been done.

Figure 20A:
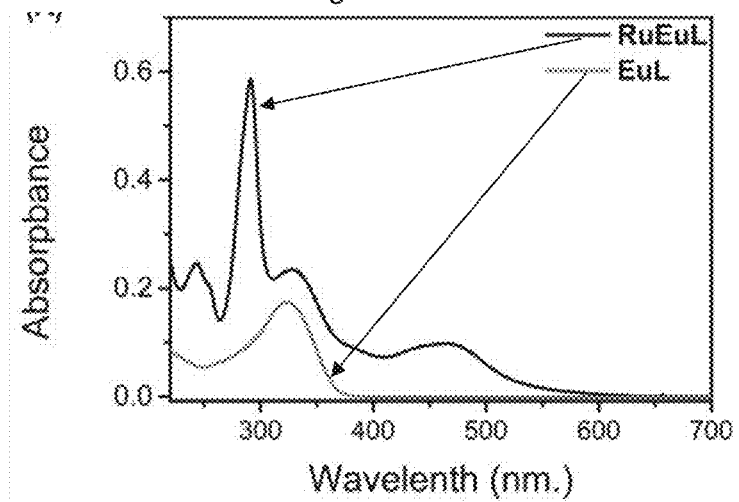
FIG. 20A shows the absorption spectra of RuEuL and EuL in aqueous solution.
Figure 20B:
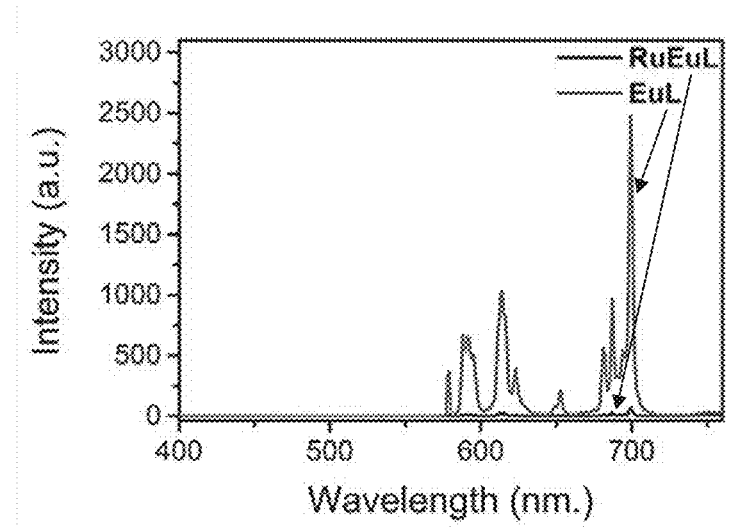
FIG. 20B shows the emission spectra of RuEuL and EuL in aqueous solution (10 μM $\lambda_{ex}$=330 nm).

The absorption and emission spectra of RuEuL and its dissociation product EuL were recorded at room temperature in aqueous solution (FIGS. 20A and 20B); they both have one similar absorption band located at ca. 330 nm resulting from the π→π*transition of their pyridine-based ligand with molar absorption coefficients of 26,970 M-1 cm-1 for RuEuL and 18,860 M-1 cm-1 for EuL (FIG. 20A). In addition, RuEuL has four other absorption bands assigned to the ruthenium moiety and located at 243 nm (π→π*transition of bpy ligand, ε=28,340 M-1 cm-1) 290 nm (π→π*transition of bpy ligand, ε=67,380 M-1 cm-1), 400 nm (shoulder, MLCT), and 464 nm (MLCT), ε=11, 200M-1 cm-1. As for the emission spectra, EuL exhibits strong red emission (corresponding to the $^5D_0 \rightarrow {}^7F_{0-4}$ transitions of Eu(III)), while RuEuL features only very weak Eu(III) emission under identical experimental conditions (FIG. 20B). The intensely sensitized Eu(III) emission of EuL arises from efficient energy transfer from the antenna chromophore to the excited states of the metal ion.

Figure 21:
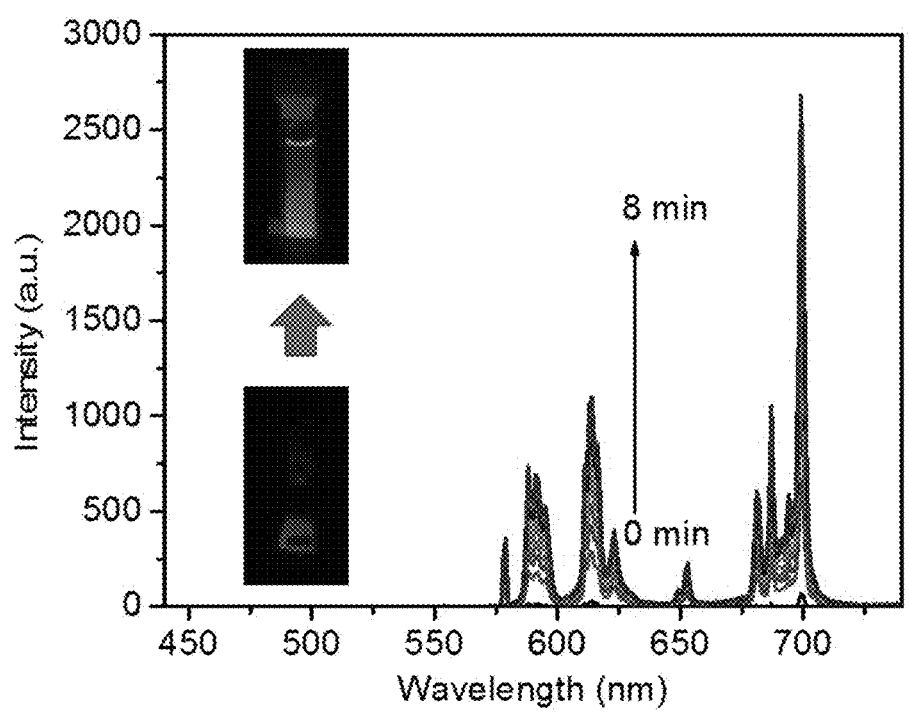
FIG. 21 shows emission spectral variation of 5 μM of RuEuL in aqueous solution under laser (455 nm, P=1 W) irradiation. The inserted figure shows photographic image of europium emission enhancement of RuEuL under 455 nm laser irradiation for 8 minutes.
Figure 22:
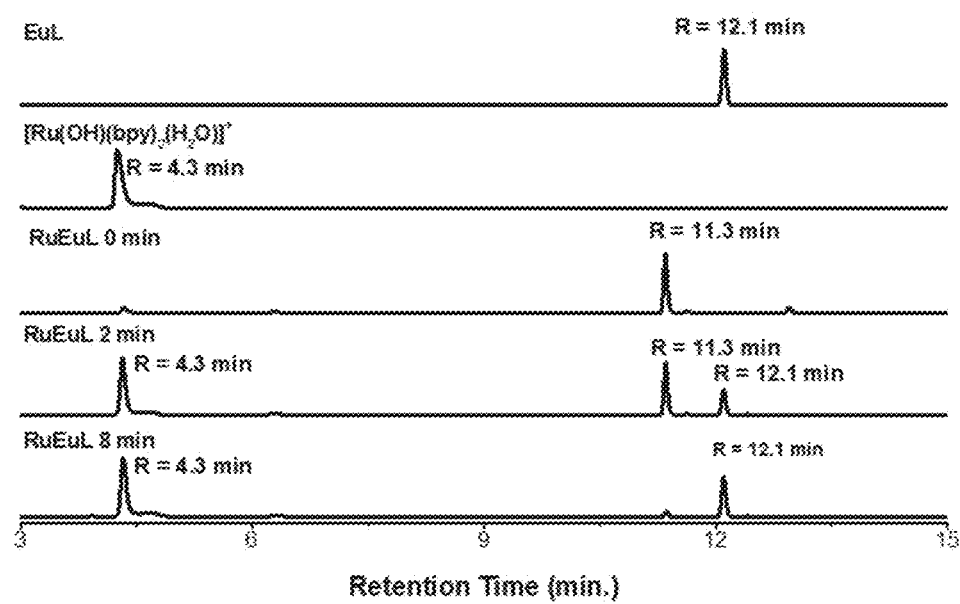
FIG. 22 shows HPLC qualitative analysis of the photodissociation of RuEuL in aqueous solution and of reference samples: EuL, [Ru(OH)(bpy)$_2$(H$_2$O)]$^+$, RuEuL, and RuEuL after 2 min and 8 min of 488 nm laser irradiation (P=1 W). The concentration for each sample is 5 μM in aqueous solution.

The photo-induced dissociation of RuEuL was simultaneously studied by emission (FIG. 21) spectroscopy, and by HPLC (FIG. 22) of the RuEuL solution (5 μM in $H_2O$) after continuous irradiation with visible light ($\lambda_{irr.}$=488 nm, 1 W) during various times (1-8 min). After irradiation, turned-on europium emission is observed. This observation can be explained by the existence of dissociative states on Ru(II), which were proposed by Saddler et al. The photo-dissociation products, EuL and $[Ru(OH)(bpy)_2(H_2O)]^+$, have been further qualitatively identified by HPLC (FIG. 22). Before light irradiation, only one HPLC peak corresponding to RuEuL (retention time, R=11.3 min) is observed. After irradiation, this peak disappears, and two peaks of dissociated photoproducts appear. Comparing the HPLC trace of the photoproducts with that of the pure complex EuL (R=12.1 min) and prepared $[Ru(OH)(bpy)_2(H_2O)]^+$ (R=4.3 min) prove that the photoproducts are similar to these compounds. These results consistently demonstrate that RuEuL can be photo-activated with visible light to generate EuL and $[Ru(OH)(bpy)_2(H_2O)]^+$ complexes.

In order to obtain the exact amount of the photo-released ruthenium(II) moiety for biomedical purpose and to evaluate drug release in real time, quantitative analysis is required. It can be achieved by LC/ESI-MS for simultaneous detection of the photo-products EuL and $[Ru(OH)(bpy)_2(H_2O)]^+$. Moreover, the switchable europium(III) emission can be considered as a real-time signaling technique for the released anticancer Ru(II) complexes and can also be exploited quantitatively. To demonstrate the feasibility of quantitative analysis of the photoproducts, standard solutions of $[Ru(OH)(bpy)_2(H_2O)]NO_3$ and EuL with concentrations 0.1, 0.2, 0.5, 1, 2 and 5 μM were prepared for establishing calibration curves.

Figure 23A:
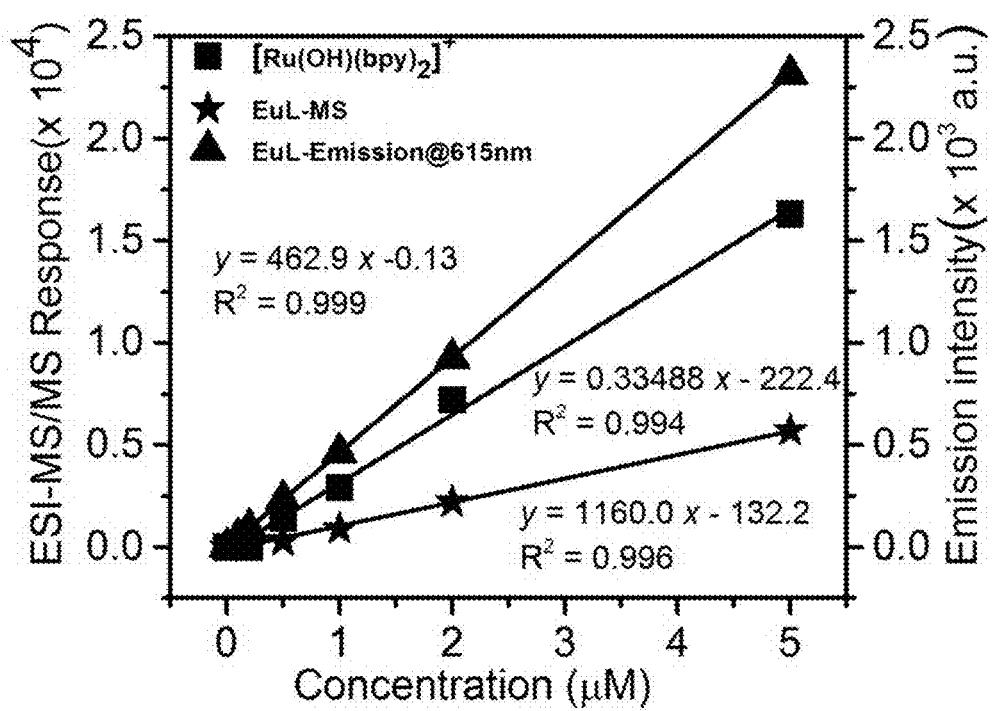
FIG. 23A shows the calibration curves of the ESI-MS response vs concentration of [Ru(OH)(bpy)$_2$]$^+$ or EuL and emission intensity vs concentration of EuL.
Figure 23B:
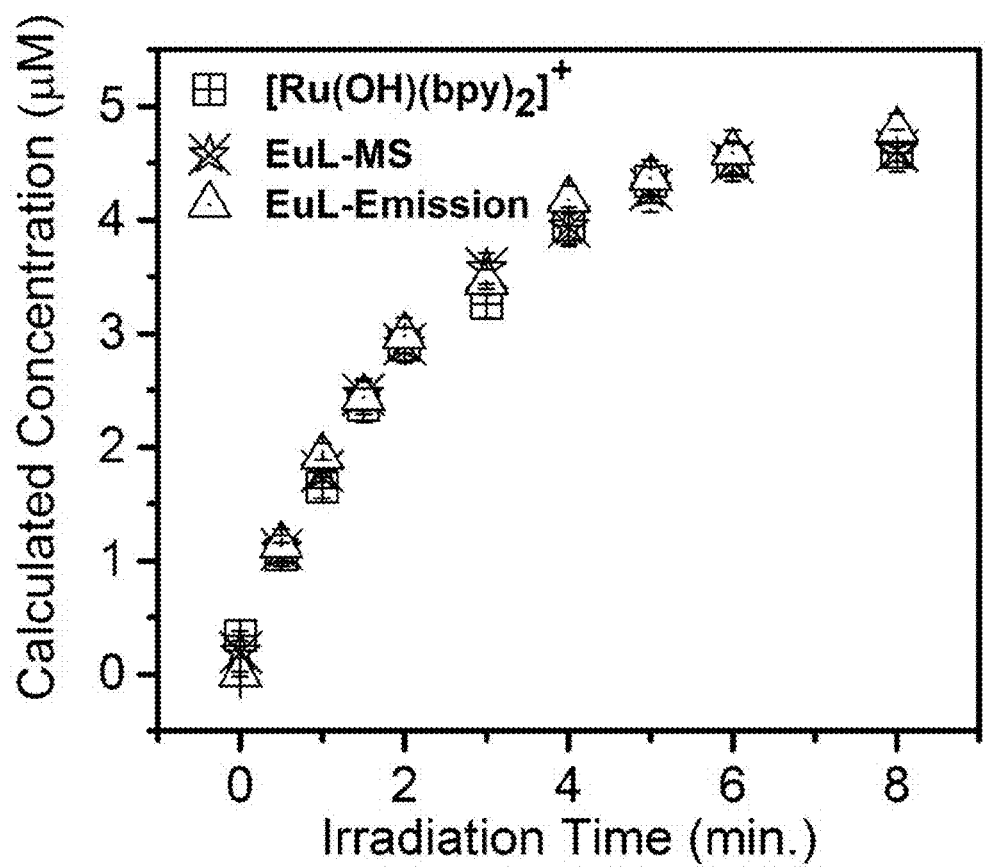
FIG. 23B shows the quantitative analysis of the photo-dissociation products [Ru(OH)(bpy)$_2$]$^+$ and EuL after irradiation of RuEuL 5 μM with 450 nm laser light (P=1 W).

A time-resolved correlation relationship was therefore established between Eu(III) emission, MS response, and the level of ruthenium compounds released (FIGS. 23A and 23B). There is a high correlation between Eu(III) emission and the amounts of dissociation products (FIG. 23A), meaning that the concentration of the released drug can be simply calculated from the Eu(III) emission intensity. A pseudo-first order rate constant k was determined from these data to be 0.43 $min^{-1}$ under the same experimental conditions as for the photophysical studies. (FIG. 23B) In the control experiment, RuEuL is stable under dark at 37° C. for 24 hours and $[Ru(OH)(bpy)_2(OH)_2]^+$ is photostable under the same experimental condition as for RuEuL photo-release.

Figure 24:
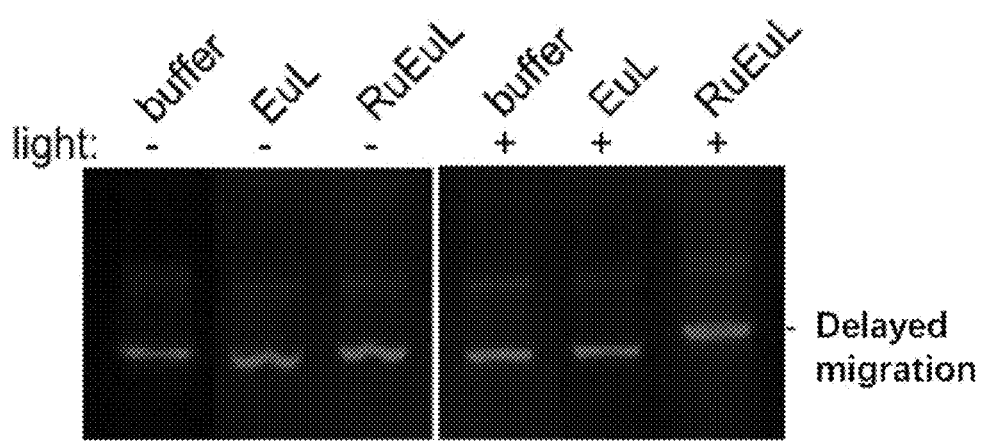
FIG. 24 shows DNA binding profile of RuEuL and EuL without light irradiation or light irradiation 455 nm, light dosage=1 J.

Furthermore, the interaction of photo-activated RuEuL with DNA was examined by agarose gel electrophoresis (FIG. 24). Plasmid DNA (22.5 μg/mL in Tris/EDTA (TE) buffer) was incubated with the compounds (20 μM), irradiated by 488 nm light (dose 50 J $m^{-2}$) or not (control) and then subjected to 1% agarose gel electrophoresis. The separated DNA was stained with GelRed Nucleic Acid Stain (BIOTIUM) and imaged using Tanon 1600 Gel Imaging System (Tanon Science & Technology Co., Ltd). In the experimental lane (with light excitation), the migration of DNA is delayed for RuEuL compared to EuL and TE buffer, whereas in the control lanes (without irradiation), RuEuL left the DNA intact and showed normal migration. EuL does not interact with DNA and shows normal migration. The delayed shift suggests the released Ru moiety from RuEuL incorporating into DNA and obviously affecting gel migration.

Figure 25A:
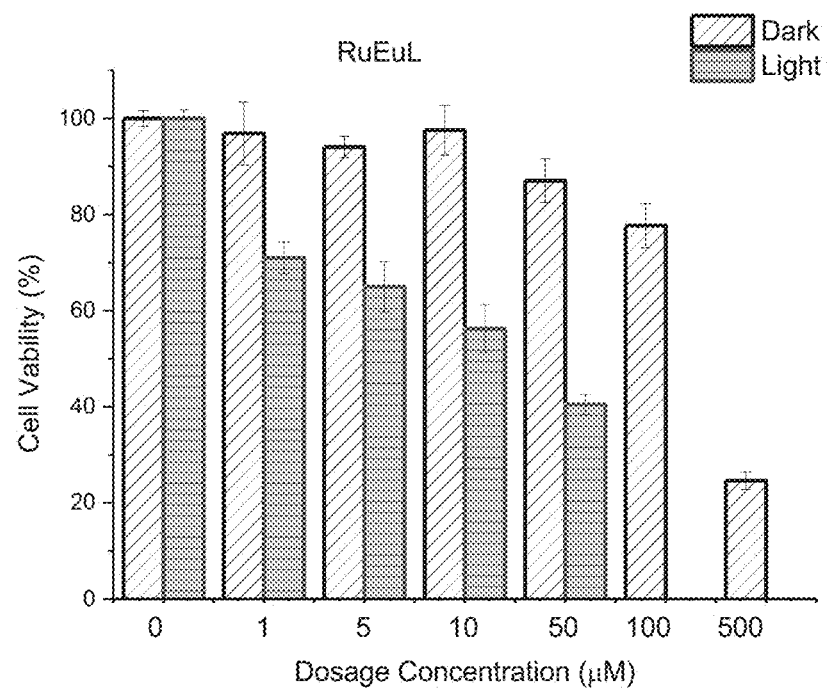
FIG. 25A shows the dark and photo-(450 nm irradiation 1 J) cytotoxicity of RuEuL against HeLa cells.
Figure 25B:
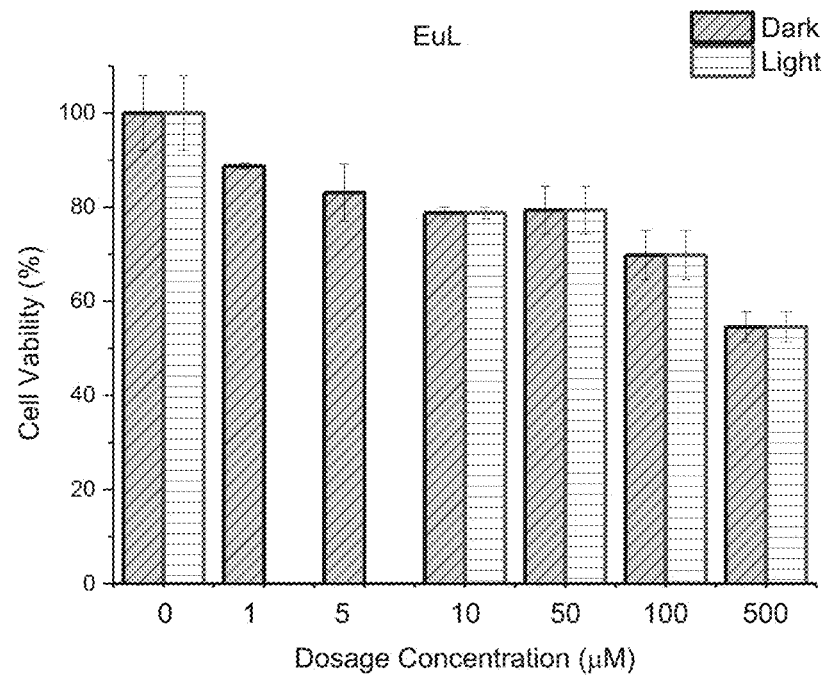
FIG. 25B shows dark and photo-(450 nm irradiation 1 J) cytotoxicity of EuL against HeLa cells.

To determine the potential of RuEuL as a photo-controlled prodrug cell cytotoxicity studies were performed on human cervical cancer (HeLa) cells, and EuL as control (FIGS. 25A and 25B). Cells were incubated 6 hours in the dark before irradiation (488 nm, 1 J); dark controls were run in parallel. As expected, EuL exhibited almost no toxicity towards HeLa cells. In contrast, photo-dissociative RuEuL showed significant light-induced cytotoxicity. After irradiation in HeLa, RuEuL was comparably more toxic (light $IC_{50}$ 32.5 μM) as PtEuL (light $IC_{50}$ 22.9 μM), but was nontoxic in the dark, with an $IC_{50}$ value over 200 μM. The approximate 10-fold difference between light and dark $IC_{50}$ values is highly suitable for a photo activated prodrug.

Figure 26A:
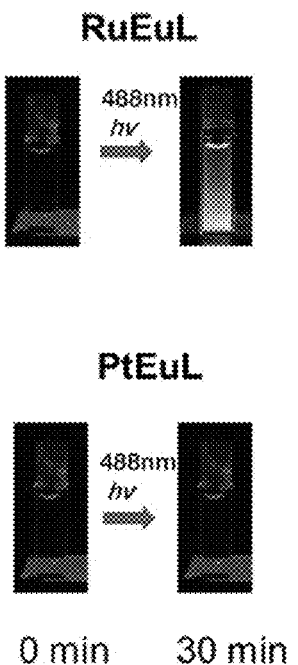
FIG. 26A shows two-photon excited monitoring of photo-induced dissociation of RuEuL and PtEuL ($\lambda_{ex.}$=700 nm) in aqueous solution.
Figure 26B:
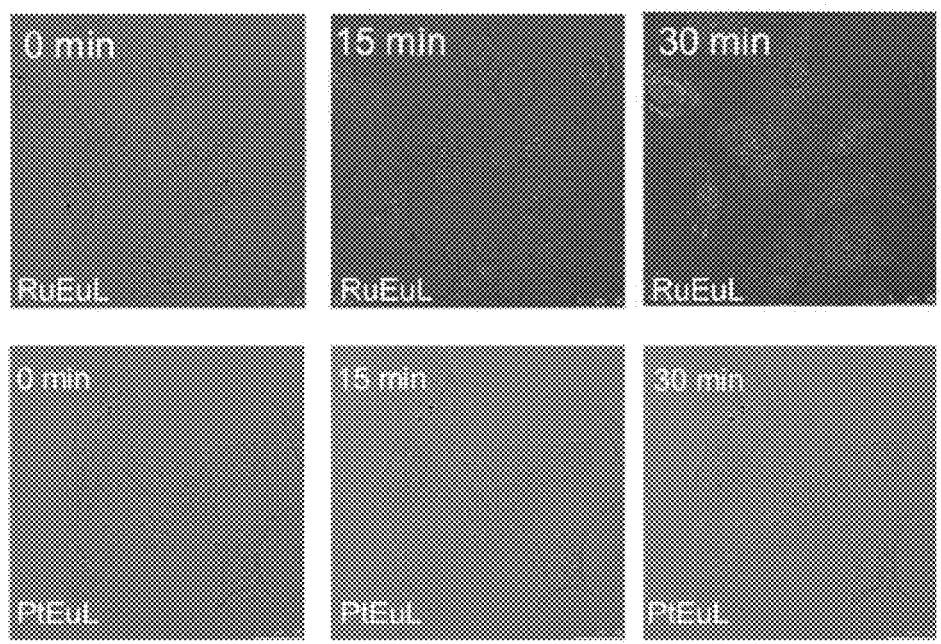
FIG. 26B shows in vitro imaging of the photo-induced drug release of RuEuL and PtEuL (control). The HeLa cells were incubated with 50 iμM of RuEuL or 10 μM of PtEuL for 6 hours and then irradiated with 488-nm laser (P=7 mW); the images were acquired under two-photon 700-nm excitation.

The light-induced cytotoxicity of RuEuL towards HeLa cells was also investigated by confocal microscopy (FIG. 26B) with the PtEuL complex tested under identical conditions for comparison. Preliminary studies were performed in pure water; with laser irradiation at 488 nm (7 mW) for 30-min, no obvious europium emission was observed, which suggested little dissociation happened in PtEuL, while the strong emission from the RuEuL solution indicated structural changes in the complex. In cell culture studies, red Eu(III) emission from RuEuL was observed after 15-min irradiation. (FIG. 26A) The emission intensity increased with longer irradiation time because more excitation energy induced the dissociation of more Ru(II) moieties from the parent molecules, and the resulting EuL units generated stronger light emission. In addition, the released Ru(II) moiety caused severe cell damage as cell lysis was detected after 15-min irradiation. In contrast, no red emission or cell death was noticed from the HeLa cells incubated with PtEuL (10 μM). This means there was no obvious cell damage induced by light irradiation because 488 nm cannot trigger the release of cisplatin from PtEuL. PtEuL is photo-activated upon ultraviolet A irradiation ($\lambda$=365 nm). However, UVA irradiation could cause severe adverse effects on human cells.

The inventors have demonstrated that one simple ruthenium-europium-based prodrug (RuEuL) with low dark cytotoxicity ($IC_{50}$>200 μM) can achieve two important tasks, photo-activated drug delivery and quantitative monitoring via two different excitation wavelengths (488 nm for drug release and 350 nm/700 nm for imaging). The light cytotoxicity in cells and the amount of drug released can be monitored by real-time europium emission of EuL under two-photon excitation in the NIR. This imaging capability could be easily extended to in vivo experiments with appropriate equipment, femtosecond laser and animal imaging box. Therefore, the multi-functional RuEuL prodrug described here can be considered as a promising model for quantitative theranostics in anti-cancer therapy.

In summary the present invention is not only limited in platinum based multi-modal prodrugs but also cover the ruthenium based prodrugs.

Further Embodiments

Real-Time In Situ Monitoring Via Europium Emission of the Photo-Release of Antitumor Cisplatin from a Eu—Pt Complex A water-soluble light-responsive antitumor agent, PtEuL, based on a cisplatin-linked europium-cyclen complex has been synthesized and evaluated for controlled cisplatin release by linear/two-photon excitation in vitro with concomitant turn-on and long-lived europium emission as a responsive traceable signal.

Figure 27:
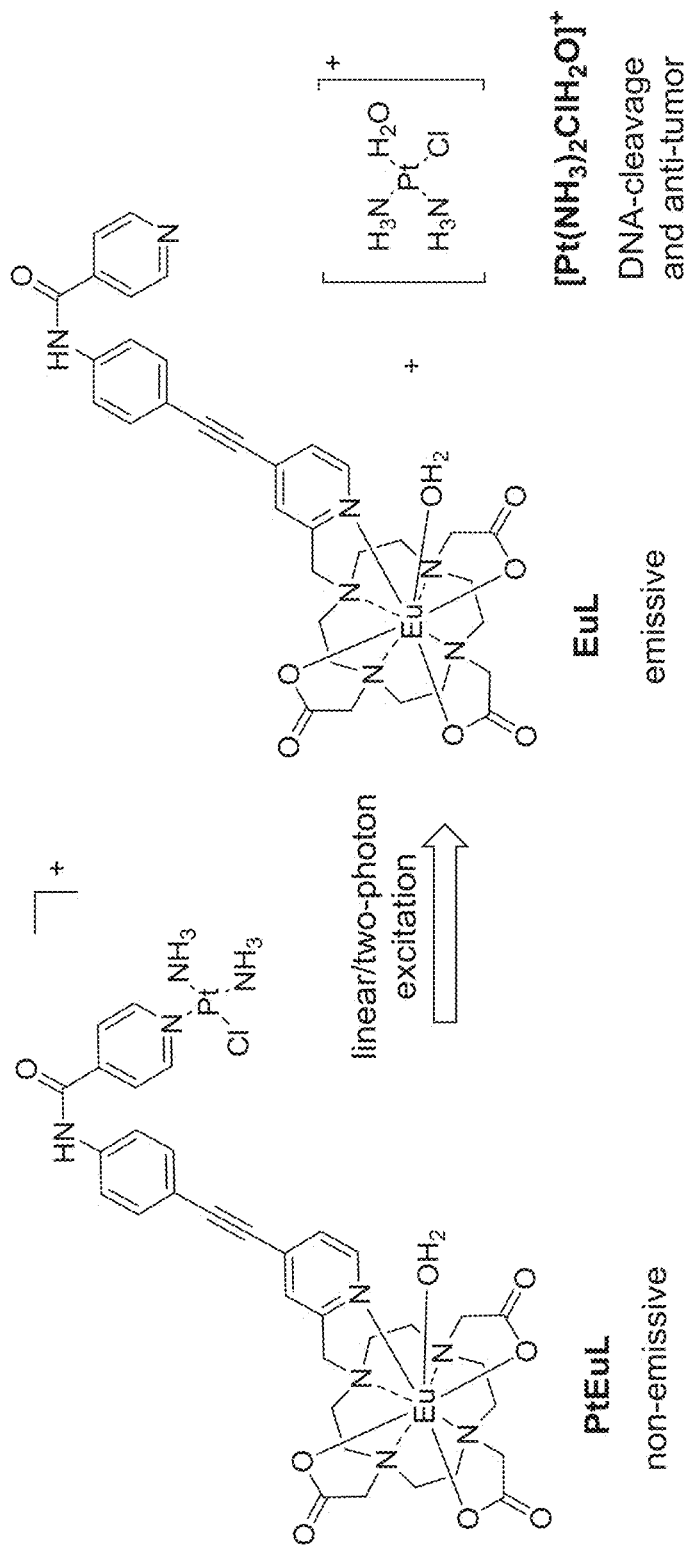
FIG. 27 shows the schematic illustration of the photo-induced cleavage of our photo-responsive anticancer bioprobe PtEuL to generate highly luminescent europium off-on signals and cytotoxic effects.

Cisplatin is a highly effective chemotherapeutic drug against a variety of solid tumors, such as testicular and non-small cell lung cancers. It exerts its anti-cancer activity mainly via extensive DNA-adduct formation which triggers apoptotic cell death. However, its vulnerability to attack by various proteins in blood, notably serum albumin and glutathione, hampers its delivery to the disease targets, resulting in many severe side effects (e.g., leucopenia, nephrotoxicity) that have limited its further application. To overcome this problem, many cisplatin analogues which slow down its reaction with protein thiols have been developed. Other strategies such as its controlled release via encapsulation by micelles, nanomaterials as well as photo-activated Pt(IV) prodrugs (i.e., systemic transport of cisplatin in a relatively inactive form and then re-activation by light at the target sites) have also been developed. In present embodiment, the inventors propose to develop a water-soluble lanthanide-cisplatin complex, PtEuL (Pt: platinum(II); Eu: europium (III); L: 2,2',2''-(10-((4-((4-(isonicotinamido)phenyl)-ethynyl) pyridin-2-yl)methyl)-1,4,7,10-tetraazacyclododecane-1,4,7-triyl)tri-acetic acid (FIG. 27)) containing the cisplatin which can be released only upon photo-irradiation. Concomitant to this photo-dissociation, the originally non-emissive Eu center of the Pt—Eu-L complex now became highly emissive, thus allowing a direct monitoring of the photo release of the cytotoxic cisplatin. Such off-on responsive europium emission can confirm the on-target delivery and release of cisplatin in vitro. The design of the PtEuL complex is based on the unique photophysical properties of the lanthanide ions. Owing to their forbidden f-f radiative transitions, appropriate organic antenna chromo-phores are required to absorb and transfer the photo-excitation energy to the lanthanide ions, thus amplifying their inherently weak but hypersensitive fingerprint emissions. The water-soluble and cell-permeable PtEuL complex is constructed from a Eu(III)-cyclen complex containing a rigid π-conjugated antenna chromophore with an isonicotinamide ligand which is coordinated to the cisplatin (FIG. 27). Due to the close proximity to the Pt center, the excitation energy absorbed by the antenna chromophore is channeled mostly via intersystem charge transfer to the dissociative states of Pt and no Eu emission is detected. Upon photo-dissociation of the cisplatin from PtEuL, energy transfer from the antenna's triplet excited state to the first excited state of Eu(II) takes place with significantly enhanced Eu emission in an off-on manner. This design complex provides a real-time trace-able delivery vehicle for cisplatin to its in vitro target. Comprehensive photophysical and in vitro studies of this complex, such as measurements of its quantum yield, sensitization efficiency, emission lifetime, DNA binding and cleavage properties, dark cytotoxicity and photocytotoxicity, have been conducted. The results obtained support the application of PtEuL as a traceable and photo-activatable prodrug for the real-time optical monitoring of the controlled and targeted delivery of cisplatin.

In this disclosure, cisplatin-free Eu complex EuL was prepared as the control for comparison. In addition, two gadolinium analogues, GdL and PtGdL, were synthesized for probing the triplet state of the cyclen-based ligand L. All the complexes, PtLnL and LnL (Ln=Eu and Gd) were obtained using synthetic Scheme 1 and characterized by HRMS and HPLC.

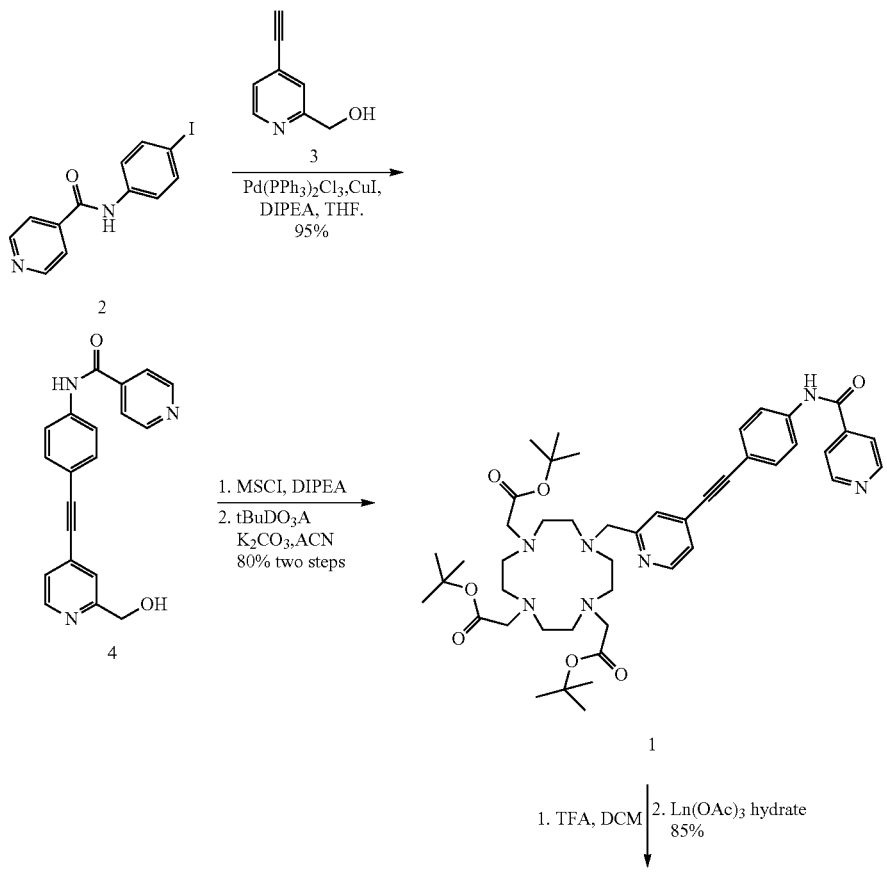

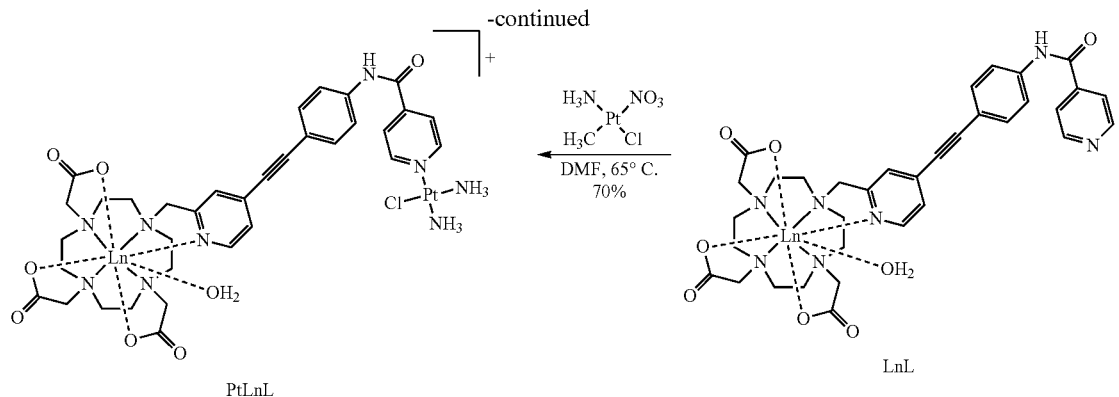

Scheme 1 shows the synthetic route for PtLnL. (Ln=Eu or Gd).

Figure 28A:
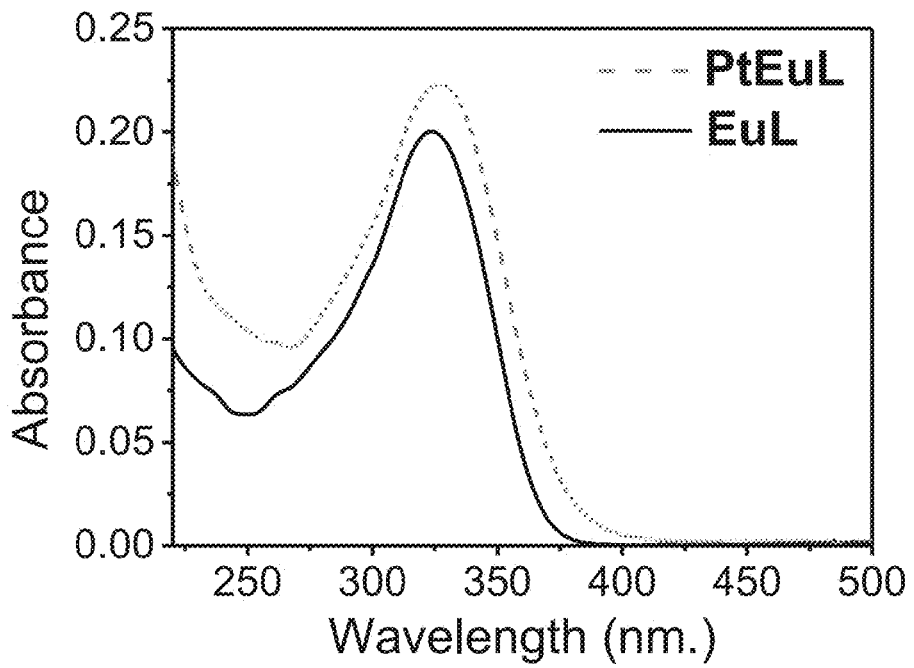
FIG. 28A shows the absorption spectrum of PtEuL and EuL (3 μM, $\lambda_{ex}$=325 nm) in aqueous solution.
Figure 28B:
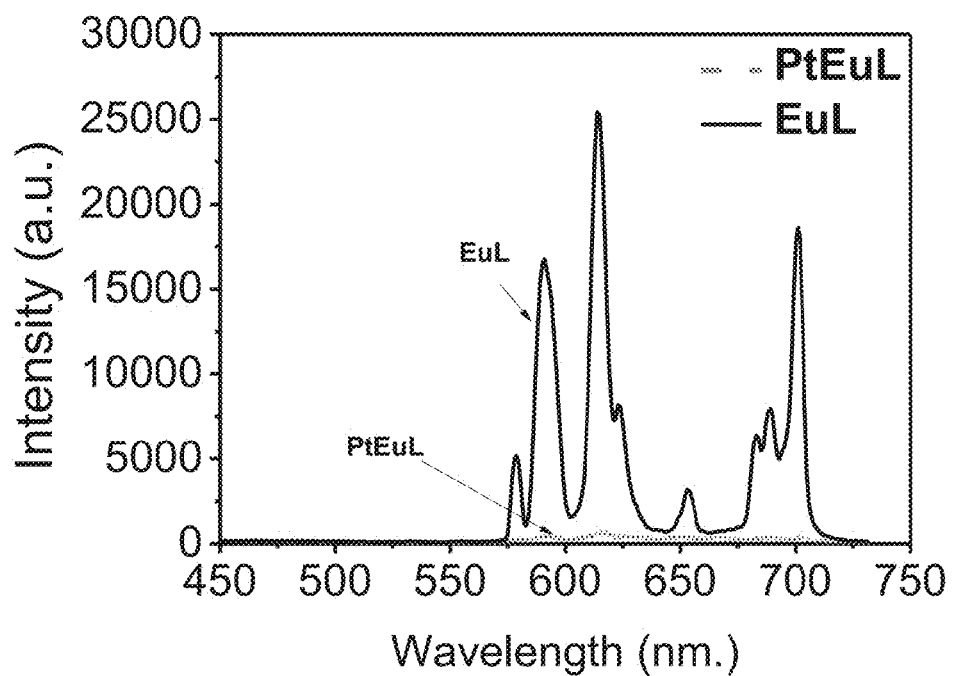
FIG. 28B shows the emission spectrum of PtEuL and EuL (3 μM, $\lambda_{ex}$=325 nm) in aqueous solution.
Figure 28C:
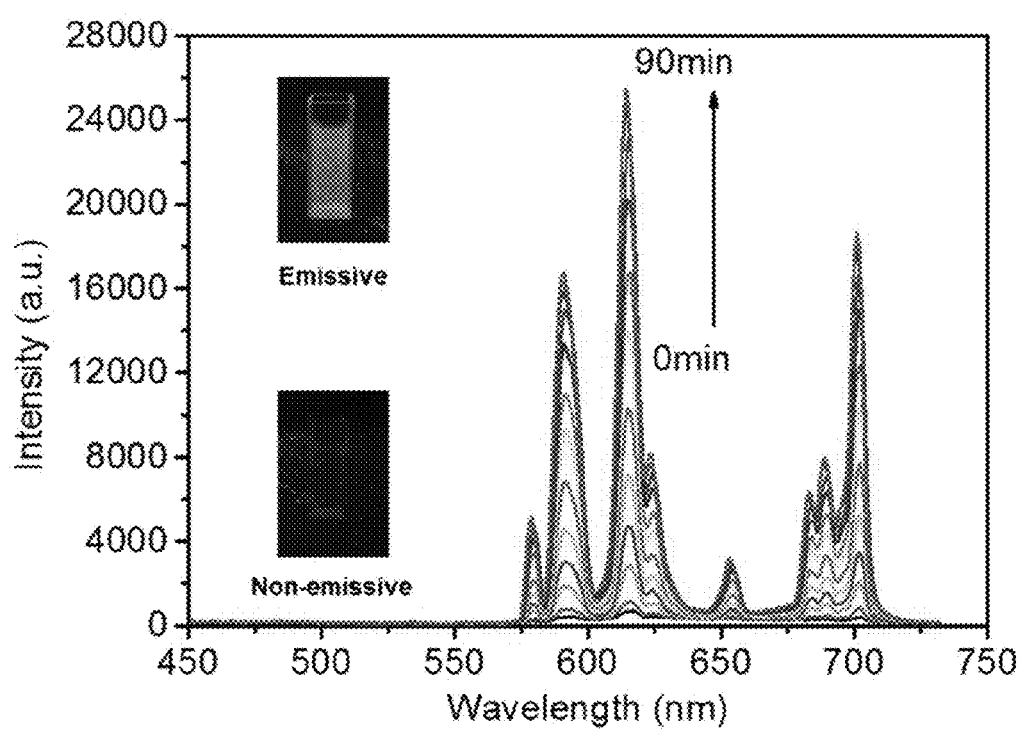
FIG. 28C shows the emission spectral variation of PtEuL under UVA (365 nm) irradiation, light dosage=4 J cm$^{-2}$ for 90 minutes. (c inset) Photographic image of europium emission enhancement of PtEuL under UVA irradiation for 20 minutes.
Figure 28D:
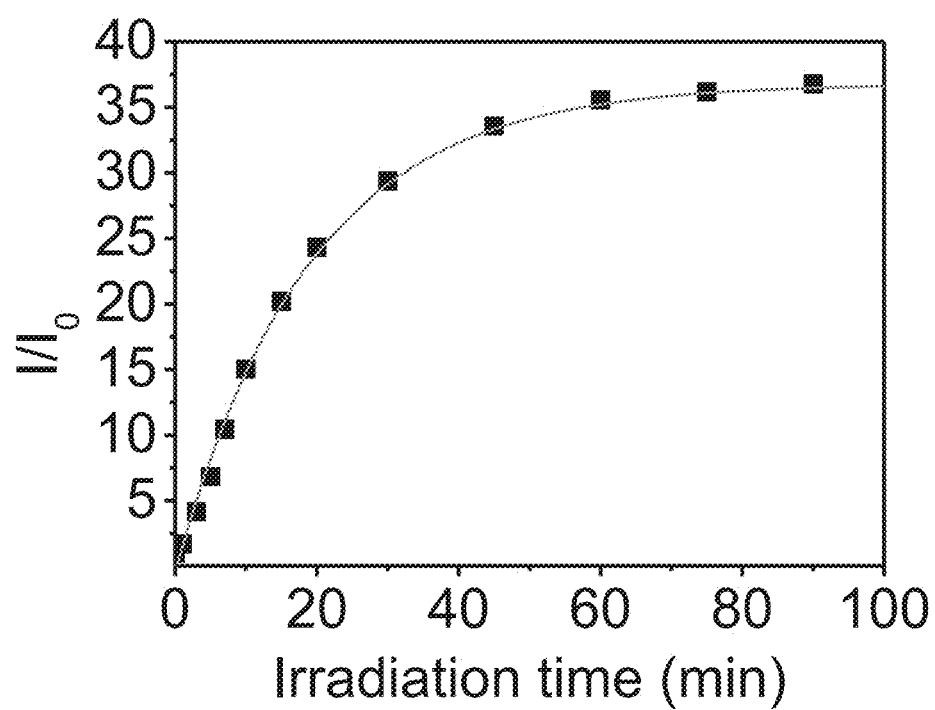
FIG. 28D shows the plot of I/I$_0$ @ 615 nm vs. time. Pseudo-first order rate constant of PtEuL k=0.53 min$^{-1}$.
Figure 30A:
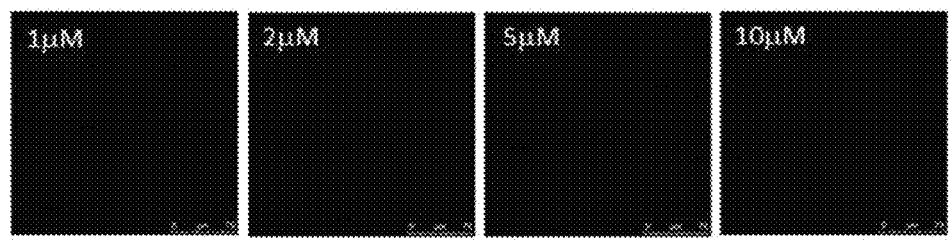
FIG. 30A shows two-photon ($\lambda_{ex}$=730 nm) induced images of HeLa cells incubated with PtEuL at different dose concentrations (0, 1, 2, 5, 10 μM) for 24 hours. Without irradiation.
Figure 30B:
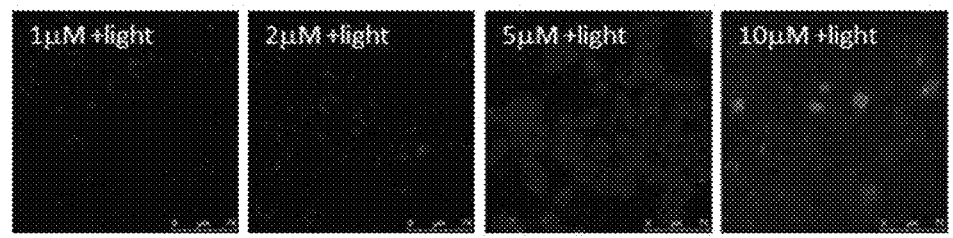
FIG. 30B shows two-photon ($\lambda_{ex}$=730 nm) induced images of HeLa cells incubated with PtEuL at different dose concentrations (0, 1, 2, 5, 10 μM) for 24 hours. After 30 minutes excitation.
Figure 30C:
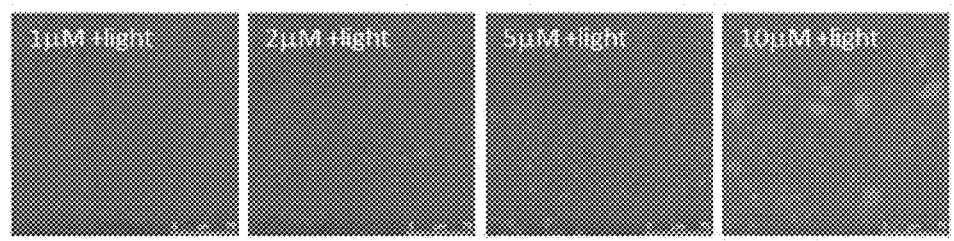
FIG. 30C shows two-photon ($\lambda_{ex}$=730 nm) induced images of HeLa cells incubated with PtEuL at different dose concentrations (0, 1, 2, 5, 10 μM) for 24 hours. Merged images of FIGS. 30A and 30B.
Figure 31:
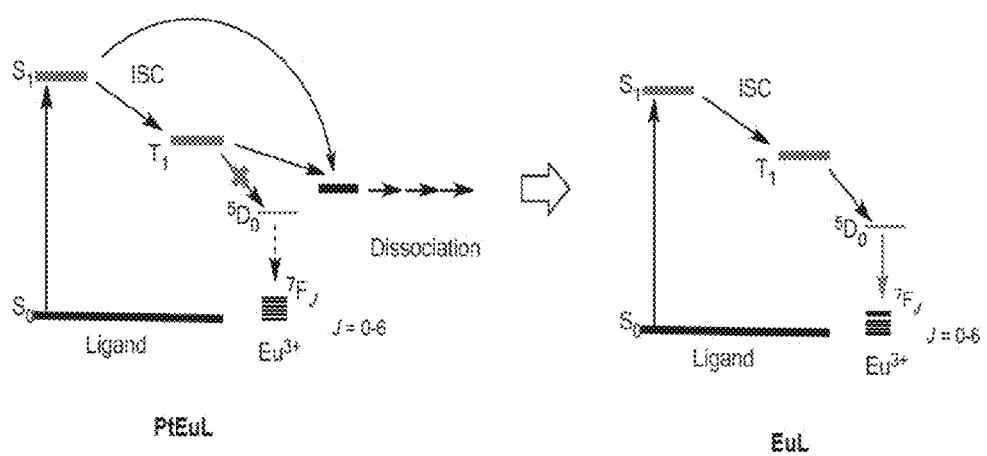
FIG. 31 shows proposed energy transfer mechanisms of sensitized europium emission of EuL and photo-induced dissociation of PtEuL.
Figure 32:
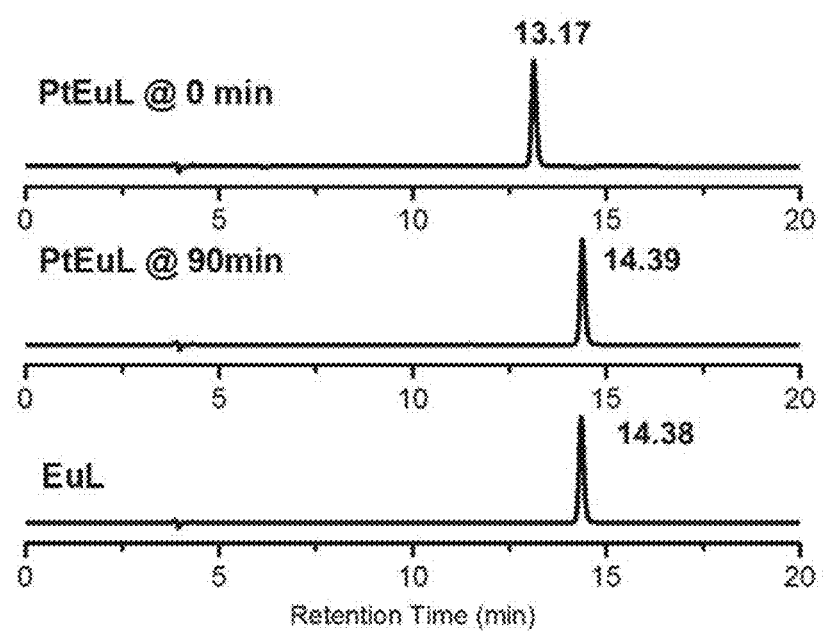
FIG. 32 shows HPLC analysis of PtEuL subjected to 0 min and 90 min of UVA irradiation and the HPLC spectrum of EuL.
Figure 33:
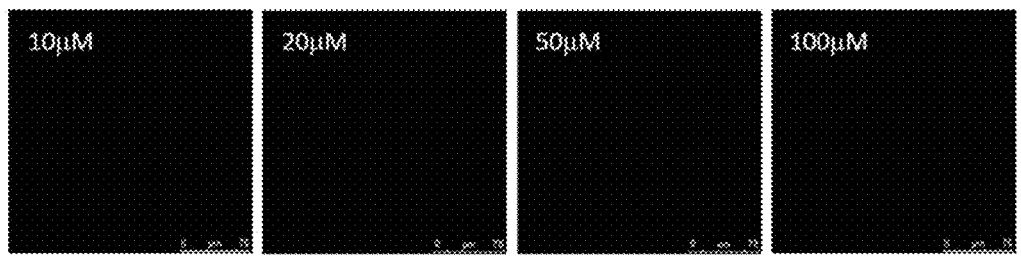
FIG. 33A shows the in vitro luminescent imaging of the HeLa cells after 24 hours of incubation with EuL (10, 20, 50 and 100 μM) after 20 min of 730 nm laser excitation (power=500 mW).
FIG. 33B shows the in vitro bright field imaging of the HeLa cells after 24 hours of incubation with EuL (10, 20, 50 and 100 μM) after 20 min of 730 nm laser excitation (power=500 mW).
Figure 33B:
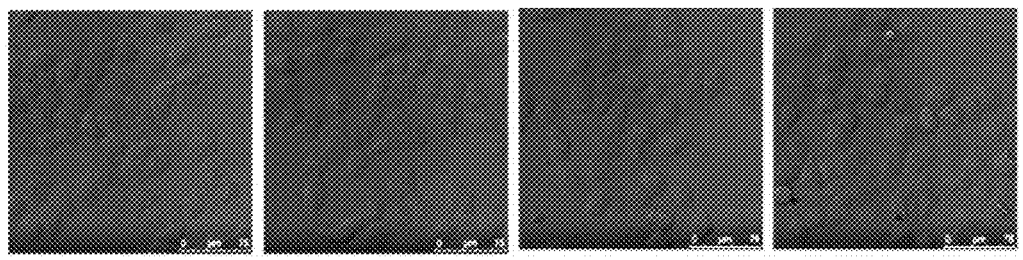

The solution-state electronic adsorption and emission spectra of all the complexes and the ligand were recorded at 298 K (FIGS. 28A-28D). The EuL complex is the product of PtEuL after photo-dissociation and was used to monitor the photo-dissociation of $[Pt-(NH_3)_2Cl]^+$ from PtEuL. The absorption bands of PtEuL and EuL are similarly located at ca. 327 and 324 nm, respectively, but the absorption coefficient of PtEuL is 22 600 $M^{-1}$ $cm^{-1}$, which is 4000 $M^{-1}$ $cm^{-1}$ higher than that of EuL (FIG. 28A). However, the emission quantum yields of PtEuL and EuL showed an opposite trend to their absorption coefficients. EuL exhibited strong red emission, with 11% quantum yield, in aqueous solution, while PtEuL gave only very weak Eu emission under identical experimental conditions (FIG. 28B). The room temperature emission spectra of PtEuL and EuL, obtained under UV excitation ($\lambda_{ex}$=325 nm) of the antenna ligand are given in FIG. 28B, which show the characteristic $^5D_0 \rightarrow ^7F_J$, where J=0-4 transitions of $Eu^{3+}$. The ratio of the $^5D_0 \rightarrow ^7F_J$ emissions, where J=0-4, from PtEuL and EuL indicated that both complexes have similar coordination geometry (FIG. 28B). The water soluble complex EuL showed intensive sensitized Eu emission because the energy level of the $T_1$ excited state of the antenna chromophore is around 20 202 $cm^{-1}$, which falls in the optimum energy transfer gap to the first excited state of Eu(III), $^5D_0$ (17 300 $cm^{-1}$) (6.17 μs,). But the phosphorescence spectra of PtGdL obtained at 77 K shows the phosphorescence band of the antenna ligand at 445 nm (22 222 $cm^{-1}$, 6.51 μs). This observation indicates that it is also possible to transfer energy to the $^5D_1$ excited state of Eu(III), populating it first and then undergoes fast nonradiative energy transfer to the $^5D_0$ state, which is then emitted. However, in the Pt—Eu complex, PtEuL, only limited energy transfer from the triplet excited state of the antenna ligand to the Eu excited states occurs, resulting in insignificant Eu emission. The proposed energy transfer mechanism of PtEuL is summarized in FIG. 31. In PtEuL; the energy absorbed by the antenna ligand is transferred to the dissociative states of the cis-Pt(II) moiety and therefore very limited energy can be transferred to the Eu(III) excited state for emission. This unusual photophysical property offers a responsive signal change upon UVA or two-photon excitation of the PtEuL complex, resulting in the dissociation of $[Pt(NH_3)Cl]^+$ from the complex for covalent attack of DNA bases in the conventional cisplatin anti-cancer chemotherapy. The sensitized charge transfer first weakens the Py-Pt bond, which subsequently results in the dissociation of the cisplatin moiety. The Eu emission can now be observed in aqueous solution (FIG. 28C) for two-photon induced in vitro imaging (FIGS. 30A-30C, UV excitation is phototoxic). The photo-dissociation of PtEuL (3 μM in Tris-buffer, pH=7.4, 50 mM NaCl) was monitored by the variation of the Eu emission ($\lambda_{em}$=615 nm, $^5D_0 \rightarrow ^7F_2$) with the irradiation time. The Eu emission intensity was enhanced by more than 35-fold (emission quantum yield increased by >100-fold) after continuous excitation of PtEuL with UVA ($\lambda$=365 nm) (FIG. 28C). The pseudo-first order rate constant k was determined to be 0.53 $min^{-1}$ under these experimental conditions (FIG. 28D). The photo-dissociation product of PtEuL after 90 min of UVA irradiation, was identified by HPLC analysis where the retention time and spectrum of the separated photoproduct was found to be in good agreement with those of the EuL synthesized (FIG. 32). As the major toxic effect of cisplatin and its analogs is mediated through its interaction with the free thiols present on proteins, its controlled release from the prodrug can enhance the interaction of the active cisplatin with its intended target at the delivered site.

Figure 29A:
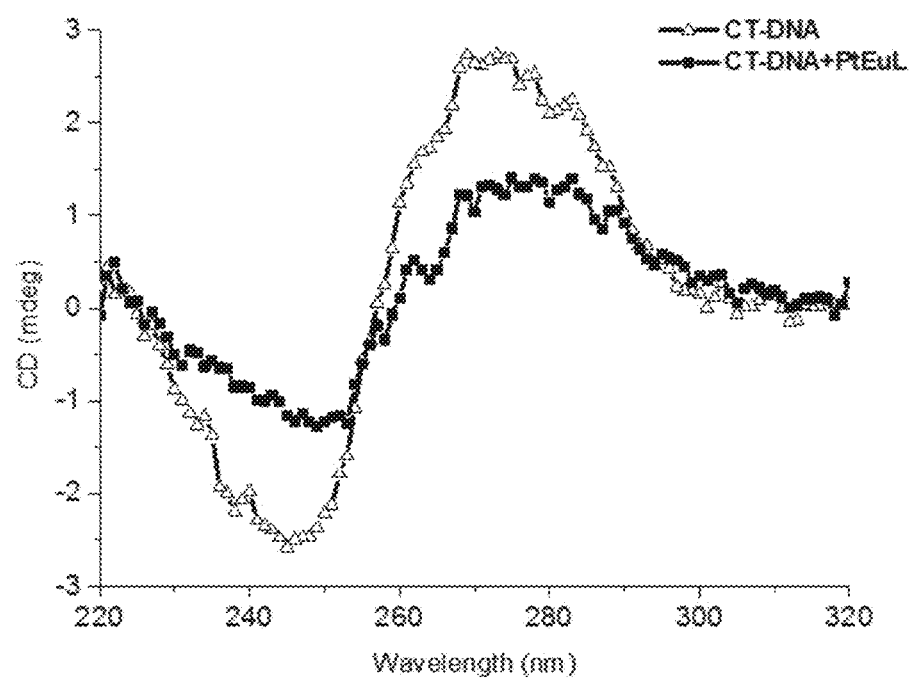
FIG. 29A shows the CD spectra of plasmid DNA (20 nM in Tris-HCl buffer, pH=7.4) treated with or without PtEuL (50 μM) in dark at 37° C. for 12 hours.
Figure 29B:
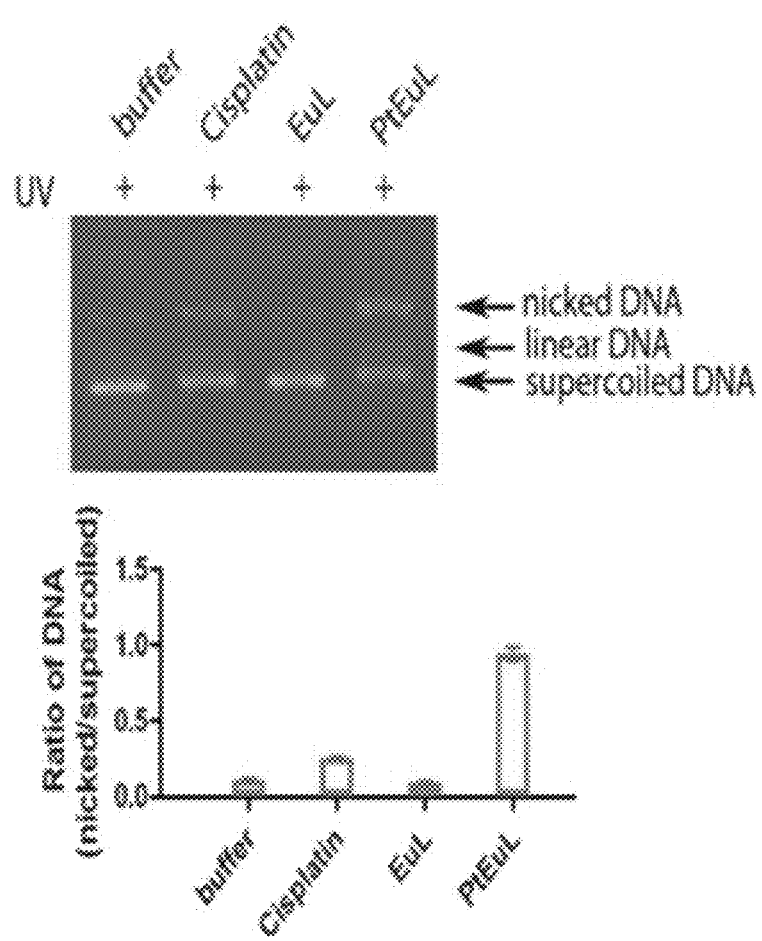
FIG. 29B shows the plasmid DNA was incubated with the test compounds (20 μM) as indicated, irradiated by UVA (light dose 50 J m$^{-2}$), and then subjected to agarose gel electrophoresis. The DNA gel images were obtained using GelRed Nucleic Acid Stain (BIOTIUM).

Direct binding of PtEuL with DNA in dark were studied by circular dichroism (CD). The CD spectra of DNA in the presence (incubation time=12 h) and absence of PtEuL are shown in FIG. 29A. The dramatic decrease in ellipticity for both the positive and negative bands of DNA in the presence of PtEuL indicates that PtEuL can directly bind to DNA and unwind its helix, leading to the loss of helicity (FIG. 29A). The interaction of photo-activated PtEuL with DNA was examined by agarose gel electrophoresis (FIG. 29B). After UVA irradiation with PtEuL, conversion of the supercoiled conformer of the plasmid DNA to its open-circular conformer, which indicates DNA nicking (single strand break) and linear conformer, which indicates double strand break, is clearly seen. Interestingly, strong DNA photocleavage activity is only seen with PtEuL, but less significantly with cisplatin and not at all with EuL, suggesting that a DNA damage mechanism distinct from that of cisplatin is operating in PtEuL. The dark cytotoxicity of PtEuL was evaluated in two cancer cell lines (HeLa and A549), together with cisplatin (Table 4). PtEuL is seen to exhibit a lower dark cytotoxicity, compared to cisplatin, towards the HeLa and A549 cells, with the respective $IC_{50}$ of 22.5±0.5 μM and 49.5±0.1 μM (Table 4). However, EuL showed no toxicity towards these two cancer cell lines under identical conditions.

Near infrared (NIR) excitation has increasingly been used in live cell imaging and photodynamic or photoactivated chemo-therapy because NIR photon ($\lambda$=650-900 nm) can penetrate deeper into tissues with pinpoint accuracy and little collateral photodamage. The two-photon photophysical properties of some antenna ligands of lanthanide complexes have been studied previously. The two-photon induced cytotoxicity of the EuL and PtEuL complexes towards HeLa cells after incubation at different dose concentrations (PtEuL: 0, 1, 2, 5, 10 μM; EuL: 0, 10, 20, 50, 100 μM) for 24 hours was studied using two-photon ($\lambda_{ex}$=730 nm) confocal microscopy (FIGS. 30A-30C and FIGS. 33A and 33B). Red emission from PtEuL was observed in this cell at >2 μM after 30 min of intermittent two-photon excitation (10 s of laser excitation per min). This emission, which increased with PtEuL dose, is closely associated with the cell nuclei and nuclear membrane, which are the known intracellular targets of cisplatin, is presumably derived from the dissociated PtEuL. In contrast, no red emission was detected from the cells treated with EuL under identical conditions. This is probably due to the lower cellular uptake rate of EuL because we no Eu emission was observed from the HeLa cells even after incubation in 100 μM of EuL, ceteris paribus. The apparent slow dissociation rate of cisplatin from PtEuL without photo-activation is crucial in maintaining the stability of the prodrug before reaching its intended target.

A series of platinum-lanthanide (e.g., platinum-europium complex (PtEuL)) or rhenium-lantanide which holds great promise as a controlled delivery vehicle of cytotoxic platinum and rhenium complexes. In addition, the lanthanide (e.g., Eu) emission produced upon the photo-dissociation of the platinum or rhenium complex (e.g., cisplatin) from the complex (e.g., PtEuL) allows real-time monitoring of e.g., the cisplatin release in vitro, thus making it a luminescence imaging as well as antitumor chemotherapeutic agent.

TABLE 4

Photophysical parameters and dark cytotoxicities of the Eu(III) complexes EuL and PtEuL

| Complex | $\lambda_{max}^{a}$/ nm | $\varepsilon^{a}$/mol L$^{-1}$cm$^{-1}$ | $E_{T1}^{b}$/ cm$^{-1}$ | τ (H$_2$O)$^c$/ms | τ (D$_2$O)$^C$/ms | q ± 0.2$^d$ | $\Phi_L^{Eu e}$/% | IC$_{50}^{f}$/μM HeLa | IC$_{50}^{f}$/ μM A549 |
|---|---|---|---|---|---|---|---|---|---|
| EuL | 324 | 18 600 | 20 202 | 0.62 | 1.99 | 1.0 | 11.0 | >500$^f$ | >500$^f$ |
| PtEuL | 327 | 22 600 | 22 222 | — | — | — | <0.1 | 22.5 ± 0.5 | 49.5 ± 2.0 |

$^a$Absorption coefficient in H$_2$O, 298K.
$^b$Triplet energy level of the chromophore obtained from the phosphorescence of the PtGdL complex (in H$_2$O/glycerol v:v = 1:1, 77K).
$^c$eu emission decay ($\lambda_{em}$ = 615 nm, $^5$D0 -> $^7$F2, $\lambda_{ex}$ = 325 nm).
$^d$Hydration number of Eu(III) complexes, q = 1.2 × [k(H$_2$O) – k(D$_2$O) – 0.25], k = t$^{-1.8}$
$^e$Overall Eu emission quantum yield in H$_2$O, determined by integrated sphere.
$^f$Dark cytotoxicity of the complex on HeLa and A549 cells. Cisplatin is used as the control in this experiment and its IC$_{50}$ on HeLa and A549 is 3.30 ± 0.1 μM and 8.70 ± 0.5 μM, respectively. IC$_{50}$ > 500 μM is from the curve of the toxicity via sample concentration. IC$_{50}$ is presented as the mean (μM) ± standard deviation of three independent experiments.

INDUSTRIAL APPLICABILITY

The present invention discloses theranostic prodrugs with responsive signals in-vitro/in-vivo. It also relates to synthesized lanthanide complexes for evaluating the binding with integrin αvβ3.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What we claim:

1. A compound comprising a chemical structure of formula (I):

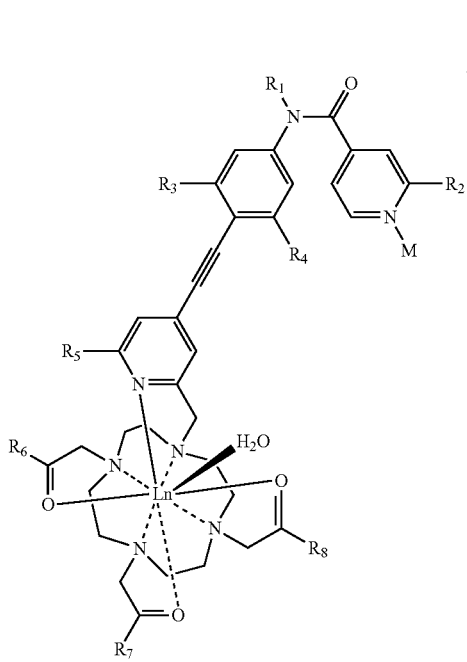

wherein Ln is a lanthanide metal;
R$_1$ is independently hydrogen, P$_n$,

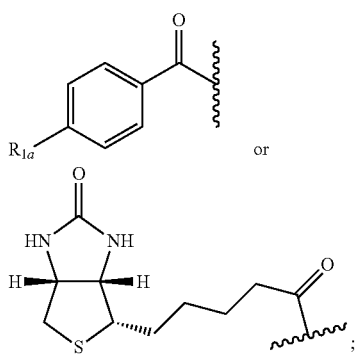

R$_{1a}$ is hydrogen or P$_n$;
R$_2$ is hydrogen or alkyl;
each of R$_3$, R$_4$ and R$_5$ is independently hydrogen, OMe, NMe$_2$, or CF$_3$;
each of R$_6$, R$_7$ and R$_8$ is independently O$^-$, P$_n$, or

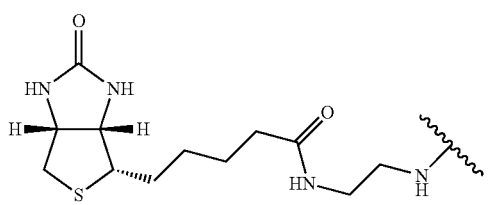 [SMILES: *NCCNC(=O)CCCC[C@@H]1SC[C@@H]2NC(=O)N[C@@H]21]

P$_n$ is a polypeptide represented by SEQ ID NO: 1, 2, 3, 4, or 5;

M represents a moiety selected from the group consisting of:

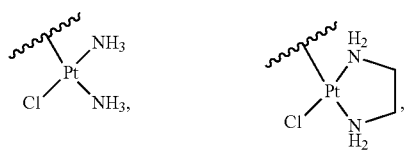

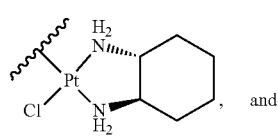

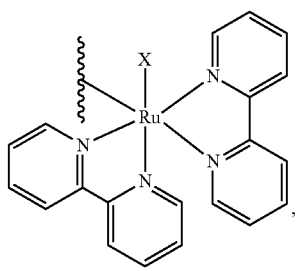

wherein X is Cl or OH; and n+ represents the net charge of the compound and is +1, +2, +3, or +4; with the proviso that if M is

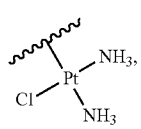

then R$_2$ is alkyl or at least one of R$_1$, R$_{1a}$, R$_6$, R$_7$, and R$_8$ is P$_n$.

2. The compound of claim 1, wherein R$_1$ is P$_n$ and R$_6$, R$_7$ and R$_8$ are O$^-$; R$_1$ is H, R$_6$ and R$_7$ are O$^-$, and R$_8$ is P$_n$; or R$_1$ is H, R$_6$ and R$_8$ are O$^-$, and R$_7$ is P$_n$; or R$_1$ is H and R$_6$, R$_7$ and R$_8$ are O$^-$.

3. The compound of claim 2, wherein R$_2$ is methyl or at least one of R$_1$, R$_6$, R$_7$, or R$_8$ is P$_n$.

4. The compound of claim 1, wherein the lanthanide metal is Eu, Gd, or Yb.

5. The compound of claim 2, wherein R$_3$, R$_4$, and R$_5$ are hydrogen.

6. The compound of claim 1, wherein the compound comprises a formula selected from the group consisting of:

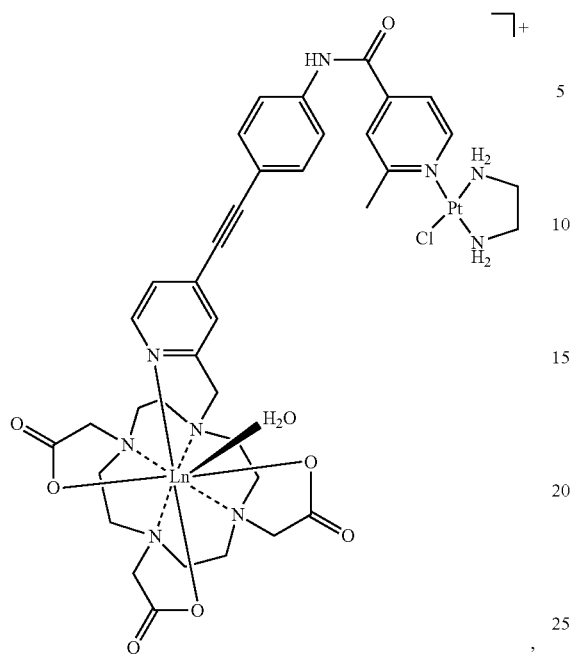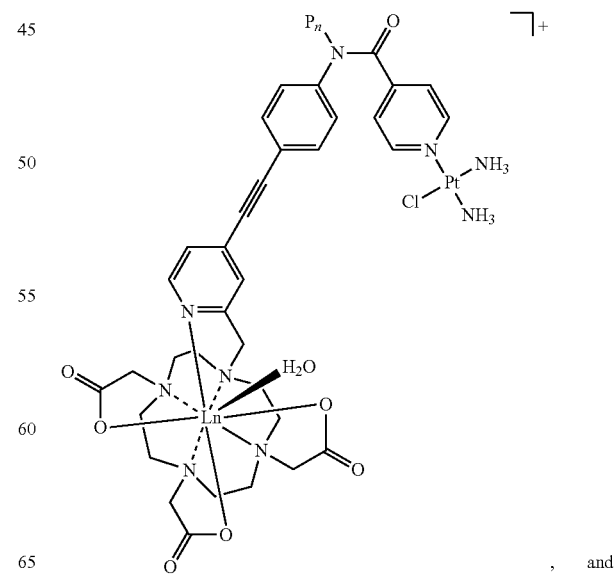

-continued

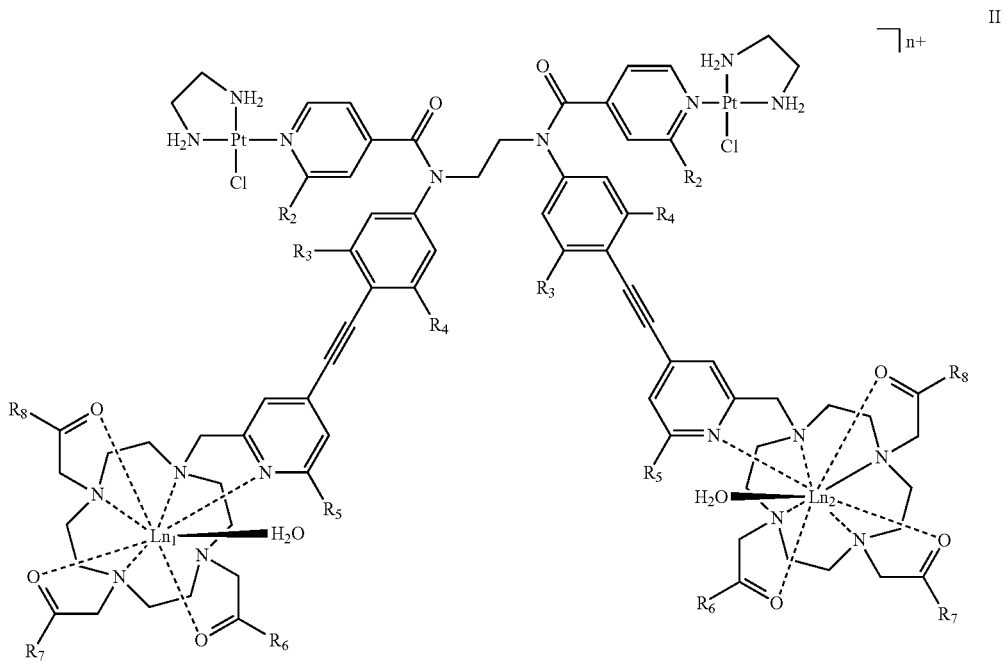

wherein $P_n$ a polypeptide represented by SEQ ID NO: 1.

7. A compound comprising a chemical structure of formula (II):

wherein, $Ln_1$ is Eu or Yb;
$Ln_2$ is Gd;
each instance of $R_2$ is independently hydrogen or alkyl;
each instance of $R_3$, $R_4$, and $R_5$ is independently H, OMe, $NMe_2$ or $CF_3$;
each instance of $R_6$, $R_7$, and $R_8$ is independently $O^-$ or $P_n$;
each instance of $P_n$ is a polypeptide is independently represented by SEQ ID NO: 1, 2, 3, 4, or 5; and n+ represents the net charge of the compound and is +2, +3, +4, or +5.

8. The compound of claim 7, wherein $R_2$ is methyl, $R_3$, $R_4$, and $R_5$ are hydrogen; $R_6$, $R_7$, and $R_8$ are $O^-$; $R_2$ is methyl, $R_3$, $R_4$, and $R_5$ are hydrogen, $R_6$ and $R_7$ are $O^-$, and $R_8$ is $P_n$; or $R_2$ is methyl, $R_3$, $R_4$, and $R_5$ are hydrogen, $R_6$ and $R_8$ are $O^-$, and $R_7$ is $P_n$.

9. A pharmaceutical composition comprising a compound of claim 1 and at least one pharmaceutically acceptable excipient.

10. The pharmaceutical composition of claim 9, comprising a mixture of

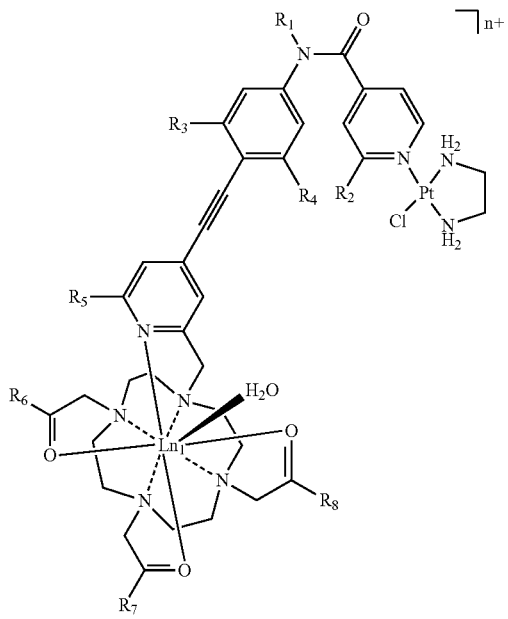

and

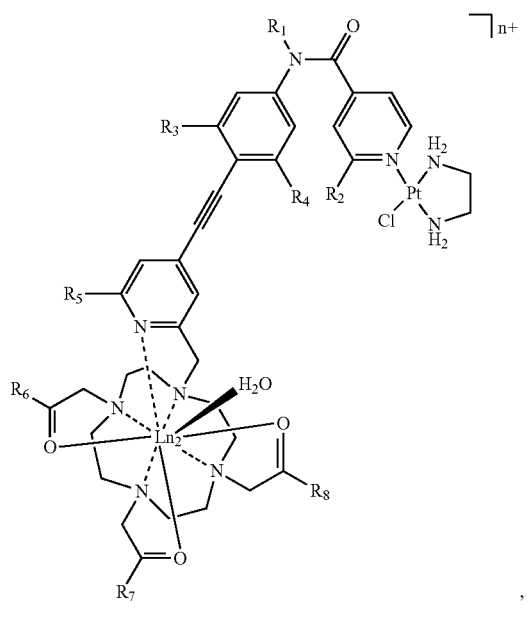

wherein $Ln_1$ is Eu or Yb; and $Ln_2$ is Gd.

11. A method of treating, imaging, or imaging and treating cancer in a patient in need thereof, comprising the step of administering an effective amount of a compound of claim 1 to the patient.

12. The method of claim 11, wherein the cancer is bladder cancer, cervical cancer skin cancer, oral cancer, or prostate cancer.

13. The method of claim 11, wherein the compound is selected from the group consisting of:

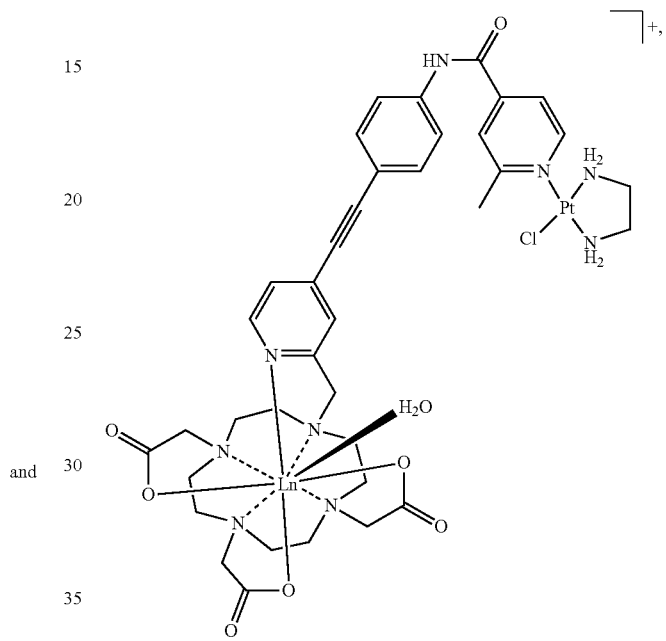

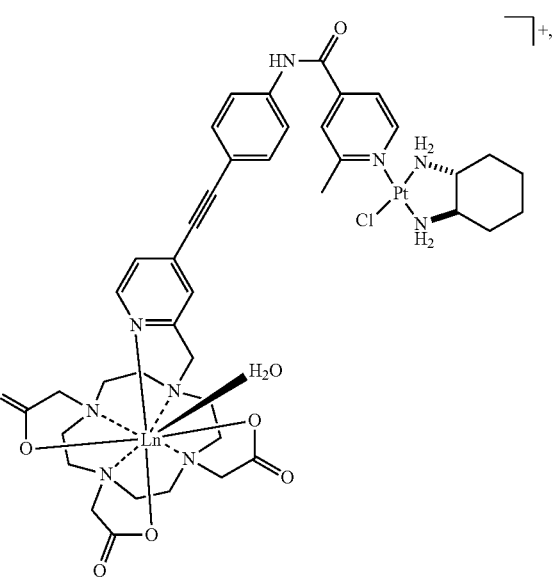

75
-continued
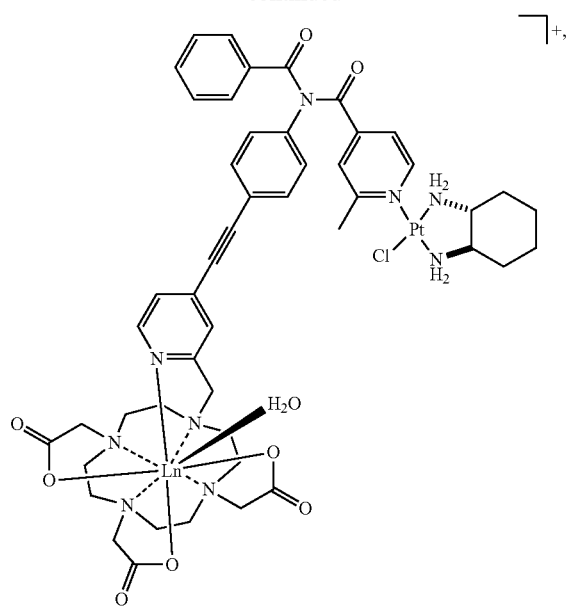
76
-continued
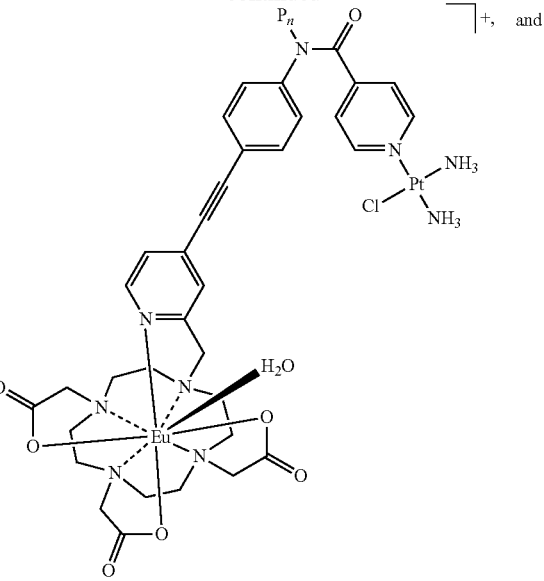
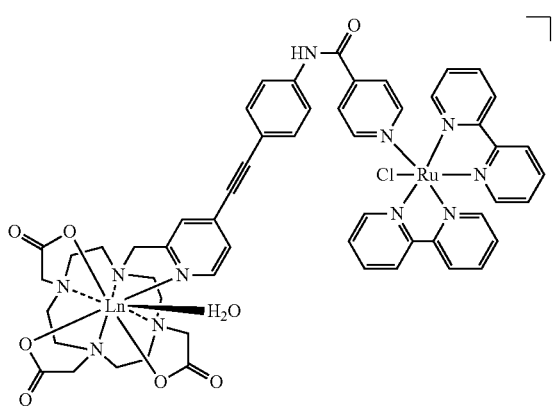
wherein $P_n$ a polypeptide represented by SEQ ID NO: 1.
* * * * *